United States Patent
Gray et al.

(10) Patent No.: US 11,371,053 B2
(45) Date of Patent: Jun. 28, 2022

(54) INCREASING PLANT GROWTH AND YIELD BY EXPRESSION OF AN M-TYPE THIOREDOXIN

(71) Applicant: Benson Hill Biosystems, Inc., Research Triangle Park, NC (US)

(72) Inventors: Benjamin Neil Gray, Chapel Hill, NC (US); Henry D. Priest, Hazelwood, MO (US)

(73) Assignee: Benson Hill, Inc., St. Louis, MO (US)

( * ) Notice: Subject to any disclaimer, the term of this patent is extended or adjusted under 35 U.S.C. 154(b) by 254 days.

(21) Appl. No.: 16/311,905

(22) PCT Filed: Jun. 28, 2017

(86) PCT No.: PCT/IB2017/053883
§ 371 (c)(1),
(2) Date: Dec. 20, 2018

(87) PCT Pub. No.: WO2018/002851
PCT Pub. Date: Jan. 4, 2018

(65) Prior Publication Data
US 2020/0165622 A1    May 28, 2020

Related U.S. Application Data

(60) Provisional application No. 62/356,120, filed on Jun. 29, 2016.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8222* (2013.01); *C12Y 108/01008* (2013.01)

(58) Field of Classification Search
None
See application file for complete search history.

(56) References Cited

U.S. PATENT DOCUMENTS

2003/0135878 A1    7/2003  Cho et al.
2011/0252501 A1*  10/2011  Abad ................ C12N 15/8251
                                                800/275

FOREIGN PATENT DOCUMENTS

WO    WO 01/98509 A2    12/2001
WO    WO 2004/018687 A2    3/2004

OTHER PUBLICATIONS

Shi et al. Influence of an m-type thioredoxin in maize on potyviral infection. (2011) Eur. J. Plant Pathol.; vol. 131; pp. 317-326 (Year : 2011).*
Peach et al. Transgene expression variability (position effect) of CAT and GUS reporter genes driven by linked divergent T-DNA promoters. (1991) Plant Molecular Biology; vol. 17; pp. 49-60 (Year: 1991).*
Schnable et al. The B73 maize genome: complexity, diversity, and dynamics. (2009) Science; vol. 326; pp. 1112-1115 plus three appended pages (Year: 2009).*
Aranjuelo, I., et al., "Alteration by tghioredoxin f over-expression of primary carbon metabolismandits response to elevated $CO_2$ in tobacco (*Nicotiana tabacum* L.)," *Environmental and Experimental Botany,* 2015, vol. 118, pp. 40-48.
Sanz-Barrio, R., et al., "Overexpression of plastidial thioredoxin f leads to enhanced starch accumulation in tobacco leaves," *Plant Biotechnology Journal,* 2013, vol. 11, pp. 618-627.
Database Geneseq, GSP:AZO46991, "Agronomic traint enhancing protein homolog SEQ:26898," 2011, 1 page.

* cited by examiner

*Primary Examiner* — Cathy Kingdon Worley
(74) *Attorney, Agent, or Firm* — Womble Bond Dickinson (US) LLP

(57) ABSTRACT

Compositions and methods for improving plant growth are provided herein. Disclosed herein are polypeptides encompassing m-type thioredoxin proteins, and polynucleotides encoding m-type thioredoxin proteins, wherein the thioredoxin protein-encoding sequence is expressed from mesophyll-preferred promoters. Also provided herein are expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants.

11 Claims, No Drawings
Specification includes a Sequence Listing.

SEQUENCE LISTING

```
<160> NUMBER OF SEQ ID NOS: 114

<210> SEQ ID NO 1
<211> LENGTH: 525
<212> TYPE: DNA
<213> ORGANISM: Zea mays
<220> FEATURE:
<221> NAME/KEY: misc_feature
<222> LOCATION: (1)..(525)
<223> OTHER INFORMATION: Thioredoxin

<400> SEQUENCE: 1
atggccctcg agacatgctt tagggcctgg gccctccacg ccgcgccagc cgggtccaag      60
gaccgcctcc tcgtgtgttc ctccgggggg aacctcgtcc tgccgtccaa gagggtcgcg     120
gccgcgccac tctccgtcgg cagggtcgcg acccgccgcg cccgccatgt gtgccagtcc     180
aaaaatgcgg tcgatgaagt gctcgtcgcg gatgaaaaaa actgggatgg catggtcatg     240
gcgtgtgaga ccccagtgct ggtcgaattc tgggccccat ggtgtgggcc gtgccgcatg     300
attgcgccgt catcgacga gctggcgaag gactatgcgg gcaaaattat gtgttgcaaa      360
gtcaatacag acgacagccc gaatgtcgcg tccacctacg gcattaggtc catcccaaca     420
gtgctcatct ttaaaggcgg cgagaagaaa gagagcgtca ttggcgcggt gccaaaaagc     480
acactcacaa ccctcatcga caaatatatc gggtccagct cctga                    525

<210> SEQ ID NO 2
<211> LENGTH: 174
<212> TYPE: PRT
<213> ORGANISM: Zea mays
<220> FEATURE:
<221> NAME/KEY: MISC_FEATURE
<222> LOCATION: (1)..(174)
<223> OTHER INFORMATION: Thioredoxin

<400> SEQUENCE: 2

Met Ala Leu Glu Thr Cys Phe Arg Ala Trp Ala Leu His Ala Ala Pro
1               5                   10                  15

Ala Gly Ser Lys Asp Arg Leu Leu Val Cys Ser Ser Gly Gly Asn Leu
            20                  25                  30

Val Leu Pro Ser Lys Arg Val Ala Ala Pro Leu Ser Val Gly Arg
        35                  40                  45

Val Ala Thr Arg Arg Ala Arg His Val Cys Gln Ser Lys Asn Ala Val
    50                  55                  60

Asp Glu Val Leu Val Ala Asp Glu Lys Asn Trp Asp Gly Met Val Met
65                  70                  75                  80

Ala Cys Glu Thr Pro Val Leu Val Glu Phe Trp Ala Pro Trp Cys Gly
                85                  90                  95

Pro Cys Arg Met Ile Ala Pro Val Ile Asp Glu Leu Ala Lys Asp Tyr
            100                 105                 110

Ala Gly Lys Ile Met Cys Cys Lys Val Asn Thr Asp Asp Ser Pro Asn
```

```
                   115                 120                 125
Val Ala Ser Thr Tyr Gly Ile Arg Ser Ile Pro Thr Val Leu Ile Phe
        130                 135                 140

Lys Gly Gly Glu Lys Lys Glu Ser Val Ile Gly Ala Val Pro Lys Ser
145                 150                 155                 160

Thr Leu Thr Thr Leu Ile Asp Lys Tyr Ile Gly Ser Ser Ser
                165                 170
```

```
<210> SEQ ID NO 3
<211> LENGTH: 780
<212> TYPE: DNA
<213> ORGANISM: Cauliflower Mosaic Virus
<220> FEATURE:
<221> NAME/KEY: promoter
<222> LOCATION: (1)..(780)
<223> OTHER INFORMATION: 2X_35S_Promoter

<400> SEQUENCE: 3
atggtggagc acgacactct cgtctactcc aagaatatca agatacagt  ctcagaagac    60
caaagggcta ttgagacttt tcaacaaagg gtaatatcgg gaaacctcct cggattccat   120
tgcccagcta tctgtcactt catcaaaagg acagtagaaa aggaaggtgg cacctacaaa   180
tgccatcatt gcgataaagg aaaggctatc gttcaagatg cctctgccga cagtggtccc   240
aaagatggac ccccacccac gaggagcatc gtggaaaaag aagacgttcc aaccacgtct   300
tcaaagcaag tggattgatg tgaacatggt ggagcacgac actctcgtct actccaagaa   360
tatcaaagat acagtctcag aagaccaaag ggctattgag acttttcaac aaagggtaat   420
atcgggaaac ctcctcggat tccattgccc agctatctgt cacttcatca aaaggacagt   480
agaaaaggaa ggtggcacct acaaatgcca tcattgcgat aaaggaaagg ctatcgttca   540
agatgcctct gccgacagtg gtcccaaaga tggaccccca cccacgagga gcatcgtgga   600
aaaagaagac gttccaacca cgtcttcaaa gcaagtggat tgatgtgata tctccactga   660
cgtaagggat gacgcacaat cccactatcc ttcgcaagac ccttcctcta taaggaag    720
ttcatttcat ttggagagga cacgctgaaa tcaccagtct ctctctacaa atctatctct   780
```

```
<210> SEQ ID NO 4
<211> LENGTH: 209
<212> TYPE: DNA
<213> ORGANISM: Cauliflower Mosaic Virus
<220> FEATURE:
<221> NAME/KEY: misc_feature
<222> LOCATION: (1)..(209)
<223> OTHER INFORMATION: 35S_PolyA

<400> SEQUENCE: 4
gatctgtcga tcgacaagct cgagtttctc cataataatg tgtgagtagt tcccagataa    60
gggaattagg gttcctatag ggtttcgctc atgtgttgag catataagaa acccttagta   120
tgtatttgta tttgtaaaat acttctatca ataaaatttc taattcctaa aaccaaaatc   180
cagtactaaa atccagatcc cccgaatta                                     209
```

```
<210> SEQ ID NO 5
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: RbcS_Promoter_and_5'UTR
```

```
<400> SEQUENCE: 5
gagctccctt taatctggcg ctagatctgc atccgcggct tgcaaagata aatggcacat      60
ttagtgtgtt attttgcaat acctttcata gtagatatcc ttaaatgcag ttttaggcat     120
gtttgggtaa ttaaataaca ttttaggag gagtttaga tttacctttc tttcgtgatg      180
actgatgaca gacgtgggga attcaaatgc aactctagcg aaagttcata tattttttcat     240 aaatagctga ggctggggta attattttt ttgtagaaaa atagaatagg tggaatggtt     300
ggggaaggcg taggcgctcg tggacgacgc ccgataaaag acaagaggcg gaattgccat     360
gaattcgagg tagctaagta aggcgcatat atatgccaaa aaattctact gtcactttcc     420
aatttcaatg cgctgccaaa caagccatcc tggaaactga cttgaattca gcccaattct     480
gtagatccaa acagggccgg cgtcagtgcc tcaggtgaga gagcagcaga cgatgcaaag     540
agccaaaact gcaagcagac gcagccgaag ccgaagccga agcccaagcc caaaactgtt     600
ttgtctttgc ccagaaccgc gacgagccta aactgcgctt cctcctatct acaagtccct     660
ggcacatcac gcatagtcca accatggcgc gcaggcgata aggcgcgcca cggggacgcg     720
acatgtggtg gcggacgcga tcaggatagg gccaggctgg ccgggcgcgg ccacgggaga     780
acggtggcca ctcgtcccac atccgcttcg tcctgtcctg tactgcgtcc tgcccccaac     840
gagagccgga gccggccatc ccgtcgcaca ctctcccccct ctatatatgc cgtcggtgtg     900
ggggagccta ctacaggacg acccaagcaa gcaagcaagc agcgagtaca tacatactag     960
gcagccaggc agcc                                                       974

<210> SEQ ID NO 6
<211> LENGTH: 439
<212> TYPE: DNA
<213> ORGANISM: Zea mays
<220> FEATURE:
<221> NAME/KEY: 3'UTR
<222> LOCATION: (1)..(439)
<223> OTHER INFORMATION: RbcS_3'UTR

<400> SEQUENCE: 6
accgcgcccg ccggccgccc cccgccggct agctagctag ctagctcctg cgtgagctag      60
tagctagtgc catgcgtcgt ctctgtcgtt cggttttgct tcgggtcacc gtgtacccctt    120 tgcttgcttg gtttcttctt tccttttttc ctttttttt cttcttttcc ccggccatgg     180
ttcctttgct ttccagcagt tctctgctgg atgtgatgta tccattgttg caatcatggc     240
cttgcattgg ctacctctat acctgctaca aaactactgc aacgcctata tacttgggg     300 gtgaggaaca tgtgaatgca agctccggct atcatataca tgtaatatgg atacaaacta     360
tatatataaa tccgccgagg cgccgacaat actatacgac accgtgttaa gttaatatat     420
aactggtgct ttttatttta                                                 439

<210> SEQ ID NO 7
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4xRGCGR_Promoter
<220> FEATURE:
<221> NAME/KEY: misc_feature
<222> LOCATION: (1)..(252)
<223> OTHER INFORMATION: RGCGR_Repeats
<220> FEATURE:
<221> NAME/KEY: 5'UTR
```

```
<222> LOCATION: (253)..(741)
<223> OTHER INFORMATION: SbCA_5'UTR

<400> SEQUENCE: 7
gaagcgagtg gcgcgctggc ggatgaggcg gcgagtggcc cggatgcacc ggcgcaggcg      60
agcgaagcga gtggcgcgct ggcggatgag gcggcgagtg gcccggatgc accggcgcag     120
gcgagcgaag cgagtggcgc gctggcggat gaggcggcga gtggcccgga tgcaccggcg     180
caggcgagcg aagcgagtgg cgcgctggcg gatgaggcgg cgagtggccc ggatgcaccg     240
gcgcaggcga gccgcacgcc gccgcccgcc gcggcgctcg cgcgcgcacc gctgccgcct     300
gccgccacac aatgcgagcg cgcgcgcaca cacacacaca ccacccgggc gggggggctg     360
tagtagtaac ggccttgtct tgtcggcacg cgcgcgtccg tgtgtataag gaggcaggcc     420
cgcgacaacg ataagcggca ctcgcacgat caatgtacac attgcccgtc cgcgccacca     480
catccagcat cgtcgccagc ctcgccaccc ccgcgccgtc ctcctcctcc ggctccggct     540
ccggccgccc caggcccagg ctcatccgga acgcccccgt cttcgccgcc ccgccaccg     600 tcgtgtaaac gggacggcgg gcagctgagg agtcaaacga gagagatcga gagaaagaaa     660
gggagggcat ccaccagccg ccggcgataa gagggagga gagagaggcc agagaagagg      720
aggagaagaa gaagaaatcg a                                               741

<210> SEQ ID NO 8
<211> LENGTH: 287
<212> TYPE: DNA
<213> ORGANISM: Zea mays
<220> FEATURE:
<221> NAME/KEY: 3'UTR
<222> LOCATION: (1)..(287)
<223> OTHER INFORMATION: CA_3'UTR

<400> SEQUENCE: 8
gttcaaaact agggctacgg caattctacc ggcccgccga ctcctgcatc atcataaata      60
tatatactat actatactac tacgtaccta ccgatatgca cccgagcaat gtgaatgcgt     120
cgagtactat atatctgttt tctgcatcta catatatata ccggatcaat cgcccaatgt     180
gaatgtaata agcaatatca ttttctacca cttttcattc ctaacgctga gcttttatg      240 tactatatct tatatgatga ataataatat gaccgccttg tgatcta                   287

<210> SEQ ID NO 9
<211> LENGTH: 1571
<212> TYPE: DNA
<213> ORGANISM: Flaveria bidentis
<220> FEATURE:
<221> NAME/KEY: promoter
<222> LOCATION: (1)..(1571)
<223> OTHER INFORMATION: GLDC_Promoter_and_5'UTR

<400> SEQUENCE: 9
aagctttact cctctcaact ttcaaatcat aacataaaag ttcgtaggtt tgtgttcttc      60
ccaaaaaaaa agtgattttt tttcatcggt taattcatga ttaacatttc gacattcatt     120
ccactatttc acatcatgtt ttgatgggag attgaaatag cgataaggcg aatgtgaaag     180
tgtgaaacag gatgagccac accatcacca catcacaatt tacccaaata atatcccaaa     240
gattcatacg cattttgatc cactgaaacc ccatccaatt ctatccaatg cccaccacat     300
gttcgacgat tgcctcagt gaatcaagac caacacatgc cactgctttc tgcttttag      360 tccctgataa caaacgattg ctttcattg ctcactgtag aaagtggaga cacccaacaa      420
```

```
ctatcatctc cacgtggttc cgtgccgcct ttttgccttt catactgctg gtgcgtcatt      480
tgtcgtcatc aaagcactca cccactatca ttgatctcga aatcttgaat ctttaggttt      540
ttatgctttg atacttgaac tctacacaca gtctcgtatc tgactttttg ttatctgtgt      600
tttgctttac taaagatctc acctttaatc aagttttgaa cttttgatgg atttgtcatg      660
ataatgaaga acacatagtt attattgatt atattttgac gaatcttttt tcatgatcgt      720
taaacataat ttgagttctt tttaccttgt ctttctttga ggtttaactg tacatgaaga      780
ctgtattttg agtttattgc ataaatggtc tatatagttt gggttaaaac aactggtttt      840
aatatcaagt ttgatactag acaaaccaac tttttgatta acttttaaaa aaattaataa      900
gtctatttgg aaaaaaattg aaaatttgat tttaagggt taaaagttct ttttgaaaag       960
ttaataagag taacttttga aatgtaactt ttaaaaaaat actgttgata aaaaaagaaa     1020
tcctaatcat gggcttagta ttgtaagtag cttggatatt gaagctaatt tttcacttta     1080
tatttataga aaagttaatg gaagtaagag gtttggatac ttttttttctt aatttagacg    1140 aatgttacac atgaaaaata agcgttgttt tgtaagattt ttttaattcg caagcactaa     1200
actcctaatc aacttttggg gttaaggagt aggcagtaaa ccaaaagcgt ttttgcacga     1260
tacgatgttc aaacatttga tctataacga taagtccaag tgcgttacaa aatgaaactt     1320
tggtatccaa tatgaaactg ggtgtgtagt tcagtaccaa aagcataact ttcagcctcc     1380
ttagtgactt atgactaggc aagagaacat gtgagcccaa tgtactaact ttttacccct     1440
tttattacca ccaccccagc cccccaccat gaaccgatca gaaaagaag caagaaaaac      1500 agagcattct tgctccttct tcttcatcaa ttcaataaca ttcttcatac cattagaccc     1560
catcttacac t                                                          1571

<210> SEQ ID NO 10
<211> LENGTH: 1814
<212> TYPE: DNA
<213> ORGANISM: Zea mays
<220> FEATURE:
<221> NAME/KEY: promoter
<222> LOCATION: (1)..(1814)
<223> OTHER INFORMATION: CA_Promoter_and_5'UTR

<400> SEQUENCE: 10
ccccgcccat gtcagcaggc ctccgaggct tttggttgcc caaccagccc atgggctgaa       60
ttcataacag tgttggcaca cagtttcctc ttcactcgga agcttattat tatcgatcct      120
gaaccagaga ctagcagagc tagcatttcg acgacgcgtc tcaactctca acctccaagt      180
ccacctcgtg tacgtgctgc cttgccagtt gccactgggc actgctggcc cagtgaccaa      240
ccatgcgtta gatctgacag caccaccgaa ccatcctccc cggtgatcaa caaacgacgg      300
cagccacatc ttgcacccaa cgtgatgatg aatgatgcct agaacttttg acaacaaaac      360
gcagcacagg tagcaggttt aattcaacaa gactttctac tatatagagc cacaccatag      420
agataactaa tctgtgcgca aagccaaagt gctgacggca actgtggtgc agccttttca      480
tctccgtttt taagtttttt gccctccctt ttgttttctg ttttctggg aactcttta       540 accgccgtgg cgccgtgtaa actttgctgt agccttttcg cgtgcaatgg cagagcgccc      600
tgttcttttc ctgctaaaga aaaaaaaaa ggagcacctg atcgctggca ggcccacggc       660
ccacccaact gtgtctgtaa cgctcggcgt ccctgcattg catgccaagt gccaaccacc      720
agtccatagc agggtcaggg agaccgcaga tgaggccggg gcaacggtga tgccgcaaag      780
aggattcaga atccttttttc ttttcttttc ttttaccacc gggctggcat cacagattac      840
```

```
acgcgcagta gagtaagcac gtctctctcg tagccaagaa caacagtcta cacagctcgc    900
tttctccgcc cttgtctggg cgttacggca ggcaagcccc ctcgttttct tctgctcgcg    960
ttctccttcc atgtccacat ctcctgtgcc accgcacgca aggtgccaac gctccctcgc   1020
cgcagtagca tcgcgtccac acaaactgca cctccactag atacggcggt gatccggcga   1080
gagagcgcga cacgcacagg ccagctagcg tttctccgac gccgcgcgtt tcatcatttc   1140
ccgcttcccc tgcccccggc cgcgcgcgcg cgcccgtgtg gtccagacca ggacgcgcgc   1200
ggatgtgcat ccggcgcgcg cccgtcggcc acacggtgcc gccgcgcgtt atcccgagcc   1260
ctgtcctgtc ctgtcctgtt ccatctcgcg cgcgaggggg ggaggggagg gcagcgagtg   1320
gcgcgctggc ggatgaggcg ccgagtggcc cgcatccacc ggcgcaggcg agccgcacga   1380
cgccgccgcg ctcgcggaac gccgccgcca cacatgcgca cccccggccc gcggggctgt   1440
aacggccttg tcgccacgcg tgcgccccgt gtgtataagg aggcagcgcg tacaggggc    1500 gacaacgata agcggcactc gcacgatcaa tctacacatt gcccgtccgc gccaccacat   1560
ccagcatcgt cgccagcctc gccacccccg cgccgtcctc ctcctccggc tccggctccg   1620
gccgccccag gcccaggctc atccggaacg ccccgtctt cgccgccccc gccaccgtcg   1680
tgtaaacggg acggcgggca gctgaggagt caaacgagag agatcgagag aaagaaaggg   1740
agggcatcca ccagccgccg gcgataagag gggaggagag agaggccaga gaagaggagg   1800
agaagaagaa gaaa                                                    1814

<210> SEQ ID NO 11
<211> LENGTH: 1412
<212> TYPE: DNA
<213> ORGANISM: Oryza sativa
<220> FEATURE:
<221> NAME/KEY: promoter
<222> LOCATION: (1)..(1412)
<223> OTHER INFORMATION: Os01g45274_promoter_and_5'UTR
<220> FEATURE:
<221> NAME/KEY: promoter
<222> LOCATION: (1)..(1301)
<223> OTHER INFORMATION: Promoter
<220> FEATURE:
<221> NAME/KEY: 5'UTR
<222> LOCATION: (1302)..(1412)
<223> OTHER INFORMATION: 5'UTR

<400> SEQUENCE: 11
atcttggcta tttcccatgg cttctccgct ctactcttgt ccctgtttgg atgacgccgt     60
ccagaccaag acatcaaaac ggggcgacac tgtgaggtta cggtgtcgcc attcgccaca    120
atgagctcac catgtcacct tgtcgacatt tcgccgcata caagtcgctg tgcgaccgcc    180
aggtgggccc cactgtgagc agcacgagtg tggcgcgtat ataaatttgt cggatggaga    240
ggcagctgaa ggttttttcgc catggcaact gcgtccttcg acatctgcgc gaaggttggg    300
ctcggaattt cgacaggata ctcacagcga aatcaatact ctgctatggc aaatggtacg    360
cactcgtttc gattgttctg ccttcttctg tttatttttt tttcccgtat gtagctgtag    420
ctgctgataa acgtgccatg tattccatct cgttcttgca agcagtttct tagatgagtt    480
aaaatatgta ttccatgtca actgttcact ttagttaggt agaactttct tacattatga    540
ttagttatct acttactctc tctgtccgat aataattatc gcattgattt ttttttataat   600 gtttgatcat tcgtcttatt aaaaaaaatt atagaattat ttttttttatt ttgtttgtga   660 cttgctttat tatcaaaaaa ataatttaaa tatggcatat cttttttttat atttacaata   720
```

```
attttttcaaa aaagatgaat ggtcaaacgt tacacgaaaa aatcaaagcg accactattt      780
tggaatggaa gtagtacctg tagagaaaaa ttaaatatta gttcttaagt gagtgtggac      840
cgaaaaaatt ccttatttat cataaacacg ttttccaaac ttttaaatga tatgtttttt      900
taaatatata aatgaacatg ttctttcaaa aatcaaataa atcactttt caagtttgta      960 ctgattaata ctagactaat catttgctaa ttgtttatat tgttttactt gccatcataa     1020
ctcatgccaa attgcttttc caacccacc attagccgct gtggcaagct cagttgctag      1080
cttgaggagg actatacaaa gttgcacaca cgccatggta ctaacgagaa ctggaaaata     1140
tgttgactgg aaaaattgta tcagttcata ttagaaacaa attactgtca gaatgaggaa     1200
aaactcagtc catgccacta aaggcatcag atgcgaattg gcgctccttt ctcctttcaa     1260
ggagtaggca taaacatagg ctctgcagta gtttcatctg agacagtcgg cacgcggggg     1320
cgcgggcgtc tatttgttgc gcgcgcgggc gcggcggcga gacgcgtgtg tagctactgc     1380
tataaggagc gcgccgtgca ccgcctctca ca                                    1412
```

```
<210> SEQ ID NO 12
<211> LENGTH: 310
<212> TYPE: DNA
<213> ORGANISM: Oryza sativa
<220> FEATURE:
<221> NAME/KEY: 3'UTR
<222> LOCATION: (1)..(310)
<223> OTHER INFORMATION: Os01g45274_3'UTR

<400> SEQUENCE: 12
```

```
atccgaccgt ccgtccgttc agttcgtcag tttacgccaa cgcttttgca taagtactac       60
ctgaggatat cgtccccgat catcgatgtg aacgcgtgga gtactactac gtacgtaccg      120
gatggttcga tatatgtgaa tgctgtatta agtaataaca agaaatatat ctcctctact      180
ttttcctgac gcggagttgt actgcctatg atgcataatt tgatcgcagt gtgatcaaaa     240
gacatcagct ataatgtctt aataatatta ttatgaagag tttacctttt tactacctt      300 tactctggta                                                            310
```

```
<210> SEQ ID NO 13
<211> LENGTH: 1176
<212> TYPE: DNA
<213> ORGANISM: Brachypodium distachyon
<220> FEATURE:
<221> NAME/KEY: misc_feature
<222> LOCATION: (1)..(1176)
<223> OTHER INFORMATION: SBPase

<400> SEQUENCE: 13
```

```
atggagaccg tggccgcctc cggctacgcc agggcgccg ccaccaggtc cccggcctgc        60
tgcgccgcca tgtccttctc ccagtcctac aggccgaagg ccgccaggcc gccgaccacc      120
ttctacggcg agtccgtgag ggccaacacc gccaggaccc tcccgggcag gcagtccaag     180
gccgcctcca gggccgccct caccaccagg tgcgccatcg gcgactccct cgaggagttc     240
ctcaccaagg ccacccccgga caagaacctc atcaggctcc tcatctgcat gggcgaggcc     300
atgaggacca tcgccttcaa ggtgaggacc gcctcctgcg gcggcaccgc tgcgtgaac      360 tccttcggcg acgagcagct cgccgtggac atgctcgccg acaagctcct cttcgaggcc     420
ctcgagtact cccacgtgtg caagtacgcc tgctccgagg aggtgccgga gctccaggac     480
atgggcggcc cggtggacgg cggcttcctc gtggccttcg acccgctcga cggctcctcc     540
atcgtggaca ccaacttcac cgtgggcacc atcttcggcg tgtggccggg cgacaagctc     600
```

```
accggcgtga ccggcggcga ccaggtggcc gccgccatgg gcatctacgg cccgaggacc    660
accttcgtgg tggccctcaa ggactgcccg ggcacccacg agttcctcct cctcgacgag    720
ggcaagtggc agcacgtgaa ggacaccacc accatcggcg agggcaagat gttctccccg    780
ggcaacctca gggccacctt cgacaacccg gactacgaca gctcgtgaa ctactacgtg     840 aaggagaagt acaccctcag gtacaccggc ggcatggtgc cggacgtgaa ccagatcatc    900
gtgaaggaga agggcatctt caccaacgtg acctccccga ccgccaaggc caagctcagg    960
ctcctcttcg aggtggcccc gctcggcttc ctcatcgaga aggccggcgg ccactcctcc   1020
gacggcaagc agtccgtgct cgacaaggtg atcaccgtgc tcgacgagag gacccaggtg   1080
gcctacggct ccaagaacga gatcatcagg ttcgaggaga ccctctacgg ctcctccagg   1140
ctcgccgccg cgccaccgt gggcgccacc gtgtga                              1176
```

<210> SEQ ID NO 14
<211> LENGTH: 391
<212> TYPE: PRT
<213> ORGANISM: Brachypodium distachyon
<220> FEATURE:
<221> NAME/KEY: MISC_FEATURE
<222> LOCATION: (1)..(391)
<223> OTHER INFORMATION: SBPase

<400> SEQUENCE: 14

```
Met Glu Thr Val Ala Ala Ser Gly Tyr Ala Arg Gly Ala Ala Thr Arg
1               5                   10                  15

Ser Pro Ala Cys Cys Ala Ala Met Ser Phe Ser Gln Ser Tyr Arg Pro
            20                  25                  30

Lys Ala Ala Arg Pro Pro Thr Thr Phe Tyr Gly Glu Ser Val Arg Ala
        35                  40                  45

Asn Thr Ala Arg Thr Leu Pro Gly Arg Gln Ser Lys Ala Ala Ser Arg
    50                  55                  60

Ala Ala Leu Thr Thr Arg Cys Ala Ile Gly Asp Ser Leu Glu Glu Phe
65                  70                  75                  80

Leu Thr Lys Ala Thr Pro Asp Lys Asn Leu Ile Arg Leu Leu Ile Cys
                85                  90                  95

Met Gly Glu Ala Met Arg Thr Ile Ala Phe Lys Val Arg Thr Ala Ser
            100                 105                 110

Cys Gly Gly Thr Ala Cys Val Asn Ser Phe Gly Asp Glu Gln Leu Ala
        115                 120                 125

Val Asp Met Leu Ala Asp Lys Leu Leu Phe Glu Ala Leu Glu Tyr Ser
    130                 135                 140

His Val Cys Lys Tyr Ala Cys Ser Glu Glu Val Pro Glu Leu Gln Asp
145                 150                 155                 160

Met Gly Gly Pro Val Asp Gly Phe Ser Val Ala Phe Asp Pro Leu
            165                 170                 175

Asp Gly Ser Ser Ile Val Asp Thr Asn Phe Thr Val Gly Thr Ile Phe
        180                 185                 190

Gly Val Trp Pro Gly Asp Lys Leu Thr Gly Val Thr Gly Gly Asp Gln
    195                 200                 205

Val Ala Ala Ala Met Gly Ile Tyr Gly Pro Arg Thr Thr Phe Val Val
        210                 215                 220

Ala Leu Lys Asp Cys Pro Gly Thr His Glu Phe Leu Leu Leu Asp Glu
225                 230                 235                 240

Gly Lys Trp Gln His Val Lys Asp Thr Thr Thr Ile Gly Glu Gly Lys
```

|     |     |     |     |     |     |     | 245 |     |     |     | 250 |     |     |     | 255 |     |
| --- | --- | --- | --- | --- | --- | --- | --- | --- | --- | --- | --- | --- | --- | --- | --- | --- |

Met Phe Ser Pro Gly Asn Leu Arg Ala Thr Phe Asp Asn Pro Asp Tyr
                                260                 265                 270

Asp Lys Leu Val Asn Tyr Tyr Val Lys Glu Lys Tyr Thr Leu Arg Tyr
            275                 280                 285

Thr Gly Gly Met Val Pro Asp Val Asn Gln Ile Ile Val Lys Glu Lys
        290                 295                 300

Gly Ile Phe Thr Asn Val Thr Ser Pro Thr Ala Lys Ala Lys Leu Arg
305                 310                 315                 320

Leu Leu Phe Glu Val Ala Pro Leu Gly Phe Leu Ile Glu Lys Ala Gly
                325                 330                 335

Gly His Ser Ser Asp Gly Lys Gln Ser Val Leu Asp Lys Val Ile Thr
                340                 345                 350

Val Leu Asp Glu Arg Thr Gln Val Ala Tyr Gly Ser Lys Asn Glu Ile
            355                 360                 365

Ile Arg Phe Glu Glu Thr Leu Tyr Gly Ser Ser Arg Leu Ala Ala Gly
        370                 375                 380

Ala Thr Val Gly Ala Thr Val
385                 390

<210> SEQ ID NO 15
<211> LENGTH: 1647
<212> TYPE: DNA
<213> ORGANISM: Synechococcus sp. PCC 7942
<220> FEATURE:
<221> NAME/KEY: misc_feature
<222> LOCATION: (1)..(1647)
<223> OTHER INFORMATION: RbcS_signal_peptide-ictB
<220> FEATURE:
<221> NAME/KEY: sig_peptide
<222> LOCATION: (1)..(243)
<223> OTHER INFORMATION: P.sativum_RbcS_signal_peptide
<220> FEATURE:
<221> NAME/KEY: misc_feature
<222> LOCATION: (244)..(1647)
<223> OTHER INFORMATION: ictB

<400> SEQUENCE: 15

| | | |
|---|---|---|
| atggcttcta tgatttcttc ttctgctgtg acaacagtgt ctagggcttc taggggccag | | 60 |
| tctgctgctg tggctccttt cggcggcctc aagtctatga caggcttccc tgtgaagaag | | 120 |
| gtgaatacag atattacatc tattacatct aatggcggca gggtgaagtg catgcaggtg | | 180 |
| tggcctccta ttggcaagaa gaagttcgag acactctctt acctccctcc tctcacaagg | | 240 |
| gatatgacag tgtggcagac actcacattc gctcattacc agcctcagca gtggggccat | | 300 |
| tcttctttcc tccataggct cttcggctct ctcagggctt ggagggcttc ttctcagctc | | 360 |
| ctcgtgtggt ctgaggctct cggcggcttc tccctcgctg tggtgtacgg ctctgctcct | | 420 |
| ttcgtgcctt cttctgctct cggcctcggc ctcgctgcta ttgctgctta ctgggctctc | | 480 |
| ctctctctca cagatattga tctcaggcag gctacaccta tcattggct cgtgctcctc | | 540 |
| tactggggcg tggatgctct cgctacaggc ctctctcctg tgagggctgc tgctctcgtg | | 600 |
| ggcctcgcta agctcacact ctacctcctc gtgttcgctc tcgctgctag ggtgctcagg | | 660 |
| aatcctaggc tcaggtctct cctcttctct gtggtggtga ttacatctct cttcgtgtct | | 720 |
| gtgtacggcc tcaatcagtg gatttacggc gtggaggagc tcgctacatg ggtggatagg | | 780 |
| aattctgtgg ctgatttcac atctagggtg tactcttacc tcgcaatcc taatctcctc | | 840 |
| gctgcttacc tcgtgcctac aacagctttc tctgctgctg ctattggcgt gtggaggggc | | 900 |

-continued

```
tggctcccta agctcctcgc tattgctgct acaggcgctt cttctctctg cctcattctc    960
acatactcta ggggcggctg gctcggcttc gtggctatga ttttcgtgtg ggctctcctc   1020
ggcctctact ggttccagcc taggctccct gctccttgga ggaggtggct cttccctgtg   1080
gtgctcggcg gcctcgtggc tgtgctcctc gtggctgtgc tcggcctcga gcctctcagg   1140
gtgagggtgc tctctatttt cgtgggcagg gaggattctt ctaataattt caggattaat   1200
gtgtggctcg ctgtgctcca gatgattcag gataggcctt ggctcggcat ggccctggc    1260
aatacagctt tcaatctcgt gtaccctctc taccagcagg ctaggttcac agctctctct   1320
gcttactctg tgcctctcga ggtggctgtg gagggcggcc tcctcggcct cacagctttc   1380
gcttggctcc tcctcgtgac agctgtgaca gctgtgcgcc aggtgtctag gctcaggagg   1440
gataggaatc ctcaggcttt ctggctcatg gcttctctcg ctggcctcgc tggcatgctc   1500
ggccatggcc tcttcgatac agtgctctac aggcctgagg cttctacact ctggtggctc   1560
tgcattggcg ctattgcttc tttctggcag cctcagcctt ctaagcagct ccctcctgag   1620
gctgagcatt ctgatgagaa gatgtga                                       1647
```

<210> SEQ ID NO 16
<211> LENGTH: 548
<212> TYPE: PRT
<213> ORGANISM: Synechococcus sp. PCC 7942
<220> FEATURE:
<221> NAME/KEY: MISC_FEATURE
<222> LOCATION: (1)..(548)
<223> OTHER INFORMATION: RbcS_signal_peptide-ictB
<220> FEATURE:
<221> NAME/KEY: MISC_FEATURE
<222> LOCATION: (1)..(81)
<223> OTHER INFORMATION: P.sativum_RbcS_signal_peptide
<220> FEATURE:
<221> NAME/KEY: MISC_FEATURE
<222> LOCATION: (82)..(548)
<223> OTHER INFORMATION: ictB

<400> SEQUENCE: 16

```
Met Ala Ser Met Ile Ser Ser Ala Val Thr Thr Val Ser Arg Ala
1               5                   10                  15

Ser Arg Gly Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Met Thr Val Trp Gln Thr Leu Thr Phe Ala His Tyr Gln Pro Gln
                85                  90                  95

Gln Trp Gly His Ser Ser Phe Leu His Arg Leu Phe Gly Ser Leu Arg
            100                 105                 110

Ala Trp Arg Ala Ser Ser Gln Leu Leu Val Trp Ser Glu Ala Leu Gly
        115                 120                 125

Gly Phe Leu Leu Ala Val Val Tyr Gly Ser Ala Pro Phe Val Pro Ser
    130                 135                 140

Ser Ala Leu Gly Leu Gly Leu Ala Ala Ile Ala Ala Tyr Trp Ala Leu
145                 150                 155                 160

Leu Ser Leu Thr Asp Ile Asp Leu Arg Gln Ala Thr Pro Ile His Trp
                165                 170                 175
```

```
Leu Val Leu Leu Tyr Trp Gly Val Asp Ala Leu Ala Thr Gly Leu Ser
            180                 185                 190

Pro Val Arg Ala Ala Leu Val Gly Leu Ala Lys Leu Thr Leu Tyr
        195                 200                 205

Leu Leu Val Phe Ala Leu Ala Ala Arg Val Leu Arg Asn Pro Arg Leu
    210                 215                 220

Arg Ser Leu Leu Phe Ser Val Val Ile Thr Ser Leu Phe Val Ser
225                 230                 235                 240

Val Tyr Gly Leu Asn Gln Trp Ile Tyr Gly Val Glu Glu Leu Ala Thr
            245                 250                 255

Trp Val Asp Arg Asn Ser Val Ala Asp Phe Thr Ser Arg Val Tyr Ser
        260                 265                 270

Tyr Leu Gly Asn Pro Asn Leu Leu Ala Ala Tyr Leu Val Pro Thr Thr
    275                 280                 285

Ala Phe Ser Ala Ala Ile Gly Val Trp Arg Gly Trp Leu Pro Lys
290                 295                 300

Leu Leu Ala Ile Ala Ala Thr Gly Ala Ser Ser Leu Cys Leu Ile Leu
305                 310                 315                 320

Thr Tyr Ser Arg Gly Gly Trp Leu Gly Phe Val Ala Met Ile Phe Val
            325                 330                 335

Trp Ala Leu Leu Gly Leu Tyr Trp Phe Gln Pro Arg Leu Pro Ala Pro
        340                 345                 350

Trp Arg Arg Trp Leu Phe Pro Val Leu Gly Gly Leu Val Ala Val
    355                 360                 365

Leu Leu Val Ala Val Leu Gly Leu Glu Pro Leu Arg Val Arg Val Leu
    370                 375                 380

Ser Ile Phe Val Gly Arg Glu Asp Ser Ser Asn Asn Phe Arg Ile Asn
385                 390                 395                 400

Val Trp Leu Ala Val Leu Gln Met Ile Gln Asp Arg Pro Trp Leu Gly
            405                 410                 415

Ile Gly Pro Gly Asn Thr Ala Phe Asn Leu Val Tyr Pro Leu Tyr Gln
        420                 425                 430

Gln Ala Arg Phe Thr Ala Leu Ser Ala Tyr Ser Val Pro Leu Glu Val
    435                 440                 445

Ala Val Glu Gly Gly Leu Leu Gly Leu Thr Ala Phe Ala Trp Leu Leu
450                 455                 460

Leu Val Thr Ala Val Thr Ala Val Arg Gln Val Ser Arg Leu Arg Arg
465                 470                 475                 480

Asp Arg Asn Pro Gln Ala Phe Trp Leu Met Ala Ser Leu Ala Gly Leu
            485                 490                 495

Ala Gly Met Leu Gly His Gly Leu Phe Asp Thr Val Leu Tyr Arg Pro
        500                 505                 510

Glu Ala Ser Thr Leu Trp Trp Leu Cys Ile Gly Ala Ile Ala Ser Phe
    515                 520                 525

Trp Gln Pro Gln Pro Ser Lys Gln Leu Pro Pro Glu Ala Glu His Ser
    530                 535                 540

Asp Glu Lys Met
545

<210> SEQ ID NO 17
<211> LENGTH: 167
<212> TYPE: PRT
<213> ORGANISM: Zea mays
<220> FEATURE:
<221> NAME/KEY: MISC_FEATURE
```

-continued

<222> LOCATION: (1)..(167)
<223> OTHER INFORMATION: Thioredoxin

<400> SEQUENCE: 17

Met Ala Met Glu Thr Cys Phe Arg Ala Trp Ala Leu His Ala Pro Ala
1               5                   10                  15

Gly Ser Lys Asp Arg Leu Leu Val Gly Asn Leu Val Leu Pro Ser Lys
            20                  25                  30

Arg Ala Leu Ala Pro Leu Ser Val Gly Arg Val Ala Thr Arg Arg Pro
        35                  40                  45

Arg His Val Cys Gln Ser Lys Asn Ala Val Asp Glu Val Val Val Ala
    50                  55                  60

Asp Glu Lys Asn Trp Asp Gly Leu Val Met Ala Cys Glu Thr Pro Val
65                  70                  75                  80

Leu Val Glu Phe Trp Ala Pro Trp Cys Gly Pro Cys Arg Met Ile Ala
                85                  90                  95

Pro Val Ile Asp Glu Leu Ala Lys Asp Tyr Ala Gly Lys Ile Thr Cys
            100                 105                 110

Cys Lys Val Asn Thr Asp Asp Ser Pro Asn Val Ala Ser Thr Tyr Gly
        115                 120                 125

Ile Arg Ser Ile Pro Thr Val Leu Ile Phe Lys Gly Gly Glu Lys Lys
    130                 135                 140

Glu Ser Val Ile Gly Ala Val Pro Lys Ser Thr Leu Thr Thr Leu Ile
145                 150                 155                 160

Asp Lys Tyr Ile Gly Ser Ser
                165

<210> SEQ ID NO 18
<211> LENGTH: 178
<212> TYPE: PRT
<213> ORGANISM: Saccharum hybrid cultivar GT28
<220> FEATURE:
<221> NAME/KEY: MISC_FEATURE
<222> LOCATION: (1)..(178)
<223> OTHER INFORMATION: Thioredoxin

<400> SEQUENCE: 18

Met Ala Leu Glu Thr Cys Phe Arg Ala Trp Ala Leu His Ala Pro Ala
1               5                   10                  15

Ala Gly Ser Lys Asp Arg Leu Leu Val Gly Ser Ser Gly Ser Ser
            20                  25                  30

Ser Asn Leu Val Leu Pro Ser Lys Arg Ala Ser Ala Val Ala Pro
        35                  40                  45

Leu Ser Val Gly Arg Val Ala Thr Arg Leu Pro Arg His Val Cys Gln
    50                  55                  60

Ser Lys Asn Ala Val Asp Glu Val Leu Val Ala Asp Glu Lys Asn Trp
65                  70                  75                  80

Asp Gly Met Val Ile Ala Cys Glu Thr Pro Val Leu Val Glu Phe Trp
                85                  90                  95

Ala Pro Trp Cys Gly Pro Cys Arg Met Ile Ala Pro Val Ile Asp Glu
            100                 105                 110

Leu Ala Lys Asp Tyr Ala Gly Lys Ile Thr Cys Cys Lys Val Asn Thr
        115                 120                 125

Asp Glu Ser Pro Asn Val Ala Ser Thr Tyr Gly Ile Arg Ser Ile Pro
    130                 135                 140

Thr Val Leu Ile Phe Lys Gly Gly Glu Lys Lys Glu Ser Val Ile Gly
145                 150                 155                 160

```
Ala Val Pro Lys Ser Thr Leu Thr Thr Leu Ile Asp Lys Tyr Val Gly
                165                 170                 175

Ser Ser

<210> SEQ ID NO 19
<211> LENGTH: 172
<212> TYPE: PRT
<213> ORGANISM: Setaria italica
<220> FEATURE:
<221> NAME/KEY: MISC_FEATURE
<222> LOCATION: (1)..(172)
<223> OTHER INFORMATION: Thioredoxin

<400> SEQUENCE: 19

Met Ala Leu Glu Thr Cys Phe Arg Ala Trp Ala Leu His Ala Ala Pro
1               5                   10                  15

Ala Gly Gly Lys Asp Arg Leu Leu Ala Gly Ser Ser Thr Ser Phe
                20                  25                  30

Ala Pro Ser Lys Arg Ala Ala Ala Pro Leu Ser Val Gly Arg
            35                  40                  45

Val Ala Thr Pro Arg Pro Arg His Val Cys Gln Ser Lys Asn Ala Val
        50                  55                  60

Asp Glu Val Leu Val Ala Asp Ala Asn Trp Asp Gly Met Val Ile
65                  70                  75                  80

Ala Cys Glu Thr Pro Val Leu Val Glu Phe Trp Ala Pro Trp Cys Gly
                85                  90                  95

Pro Cys Arg Met Ile Ala Pro Val Ile Asp Glu Leu Ala Lys Asp Tyr
            100                 105                 110

Ala Gly Lys Ile Lys Cys Cys Lys Val Asn Thr Asp Asp Asn Pro Lys
        115                 120                 125

Val Ala Ser Thr Tyr Gly Ile Arg Ser Ile Pro Thr Val Leu Ile Phe
    130                 135                 140

Lys Gly Gly Asp Lys Lys Glu Ser Val Ile Gly Ala Val Pro Lys Thr
145                 150                 155                 160

Thr Leu Thr Thr Leu Ile Asp Lys Tyr Ile Gly Ser
                165                 170

<210> SEQ ID NO 20
<211> LENGTH: 183
<212> TYPE: PRT
<213> ORGANISM: Sorghum bicolor
<220> FEATURE:
<221> NAME/KEY: MISC_FEATURE
<222> LOCATION: (1)..(183)
<223> OTHER INFORMATION: Thioredoxin

<400> SEQUENCE: 20

Met Ala Leu Glu Thr Cys Phe Arg Ala Trp Ala Leu His Ala Ala Pro
1               5                   10                  15

Ala Ala Gly Gly Lys Asp Ser Arg Leu Leu Val Val Gly Ser Ser Ser
                20                  25                  30

Gly Ser Gly Ser Asn Leu Val Leu Pro Ser Lys Arg Ala Ala Ala
            35                  40                  45

Ala Val Val Ala Pro Leu Ser Val Gly Arg Val Ala Thr Arg Arg Pro
        50                  55                  60

Arg His Val Cys Gln Ser Lys Asn Ala Val Asp Glu Val Leu Val Ala
65                  70                  75                  80

Asp Glu Lys Asn Trp Asp Gly Met Val Met Ala Cys Glu Thr Pro Val
```

```
                85                  90                  95
Leu Val Glu Phe Trp Ala Pro Trp Cys Gly Pro Cys Arg Met Ile Ala
            100                 105                 110

Pro Val Ile Asp Glu Leu Ala Lys Asp Tyr Ala Gly Lys Ile Thr Cys
        115                 120                 125

Cys Lys Val Asn Thr Asp Glu Ser Pro Asn Val Ala Ser Thr Tyr Gly
    130                 135                 140

Ile Arg Ser Ile Pro Thr Val Leu Ile Phe Lys Ala Gly Glu Lys Lys
145                 150                 155                 160

Glu Ser Val Ile Gly Ala Val Pro Lys Ser Thr Leu Thr Thr Leu Ile
                165                 170                 175

Asp Lys Tyr Ile Gly Thr Ser
            180

<210> SEQ ID NO 21
<211> LENGTH: 168
<212> TYPE: PRT
<213> ORGANISM: Zea mays
<220> FEATURE:
<221> NAME/KEY: MISC_FEATURE
<222> LOCATION: (1)..(168)
<223> OTHER INFORMATION: Thioredoxin

<400> SEQUENCE: 21

Met Ala Met Glu Thr Cys Phe Arg Ala Trp Ser Leu Ser Ile Pro Ala
1               5                   10                  15

Gly Ser Lys Asp Arg Leu Leu Val Gly Asn Leu Gln Leu Leu Pro Ser
            20                  25                  30

Lys Arg Pro His Ala Pro Leu Ser Val Ser Arg Ile Ser Met Glu Arg
        35                  40                  45

Pro Arg His Val Cys Gln Ser Lys Asn Ile Val Gln Glu Val Val Val
    50                  55                  60

Ala Asp Glu Lys Asn Trp Asp Ser Leu Leu Ile Ala Cys Glu Thr Pro
65                  70                  75                  80

Val Leu Val Glu Phe Trp Ala Pro Trp Leu Gly Pro Ser Arg Met Ile
                85                  90                  95

Ala Pro Lys Ile His Ser His Lys His Tyr Thr Gly His Phe Thr
            100                 105                 110

Cys Cys Lys Val Asn Thr Tyr Asp Ser Pro Asn Val Ala Ser Ile Tyr
        115                 120                 125

Val Ile Arg Ser Ile Pro Thr Val Leu Ile Phe Lys Gly Gly Glu Asn
    130                 135                 140

Lys Glu Ser Val Ile Gly Ala Val Pro Lys Ser Thr Leu Thr Thr Leu
145                 150                 155                 160

Leu Asp Lys Tyr Ile Gly Ser Ser
                165

<210> SEQ ID NO 22
<211> LENGTH: 175
<212> TYPE: PRT
<213> ORGANISM: Aegilops tauschii
<220> FEATURE:
<221> NAME/KEY: MISC_FEATURE
<222> LOCATION: (1)..(175)
<223> OTHER INFORMATION: Thioredoxin

<400> SEQUENCE: 22

Met Ala Leu Glu Thr Cys Leu Arg Gly Trp Ala Leu His Ala Pro Gln
1               5                   10                  15
```

```
Ala Gly Ile Arg Glu Arg Leu Ser Ser Gly Ser Tyr Ala Pro Ser Arg
            20                  25                  30

Pro Arg Thr Ala Ala Pro Ala Val Val Ser Pro Ser Pro Tyr Lys Tyr
        35                  40                  45

Ala Leu Val Ala Ala Arg Arg Pro Ser Arg Phe Val Cys Lys Cys Lys
 50                  55                  60

Asn Val Val Asp Glu Val Ile Val Ala Asp Glu Lys Asn Trp Asp Asn
65                  70                  75                  80

Met Val Ile Ala Cys Glu Ser Pro Val Leu Val Glu Phe Trp Ala Pro
                85                  90                  95

Trp Cys Gly Pro Cys Arg Met Ile Ala Pro Val Ile Asp Glu Leu Ala
            100                 105                 110

Lys Asp Tyr Val Gly Lys Ile Lys Cys Cys Lys Val Asn Thr Asp Asp
        115                 120                 125

Cys Pro Asn Ile Ala Ser Thr Tyr Gly Ile Arg Ser Ile Pro Thr Val
130                 135                 140

Leu Met Phe Lys Asp Gly Glu Lys Lys Glu Ser Val Ile Gly Ala Val
145                 150                 155                 160

Pro Lys Thr Thr Leu Cys Thr Ile Ile Asp Lys Tyr Ile Gly Ser
                165                 170                 175

<210> SEQ ID NO 23
<211> LENGTH: 175
<212> TYPE: PRT
<213> ORGANISM: Triticum aestivum
<220> FEATURE:
<221> NAME/KEY: MISC_FEATURE
<222> LOCATION: (1)..(175)
<223> OTHER INFORMATION: Thioredoxin

<400> SEQUENCE: 23

Met Ala Leu Glu Thr Cys Leu Arg Gly Trp Ala Leu Tyr Ala Pro Gln
1               5                   10                  15

Ala Gly Ile Arg Glu Arg Leu Ser Ser Gly Ser Tyr Ala Pro Ser Arg
            20                  25                  30

Pro Arg Thr Ala Ala Pro Ala Val Val Ser Pro Ser Pro Tyr Lys Ser
        35                  40                  45

Ala Leu Val Ala Ala Arg Arg Pro Ser Arg Phe Val Cys Lys Cys Lys
 50                  55                  60

Asn Val Val Asp Glu Val Ile Val Ala Asp Glu Lys Asn Trp Asp Asn
65                  70                  75                  80

Met Val Ile Ala Cys Glu Ser Pro Val Leu Val Glu Phe Trp Ala Pro
                85                  90                  95

Trp Cys Gly Pro Cys Arg Met Ile Ala Pro Val Ile Asp Glu Leu Ala
            100                 105                 110

Lys Asp Tyr Val Gly Lys Ile Lys Cys Cys Lys Val Asn Thr Asp Asp
        115                 120                 125

Cys Pro Asn Ile Ala Ser Thr Tyr Gly Ile Arg Ser Ile Pro Thr Val
130                 135                 140

Leu Met Phe Lys Asp Gly Glu Lys Lys Glu Ser Val Ile Gly Ala Val
145                 150                 155                 160

Pro Lys Thr Thr Leu Cys Thr Ile Ile Asp Lys Tyr Ile Gly Ser
                165                 170                 175

<210> SEQ ID NO 24
<211> LENGTH: 175
```

```
<212> TYPE: PRT
<213> ORGANISM: Hordeum vulgare
<220> FEATURE:
<221> NAME/KEY: MISC_FEATURE
<222> LOCATION: (1)..(175)
<223> OTHER INFORMATION: Thioredoxin

<400> SEQUENCE: 24

Met Ala Leu Glu Thr Cys Leu Arg Val Trp Ala Leu His Ala Pro Gln
1               5                   10                  15

Thr Gly Ile Arg Glu Arg Leu Ser Ser Gly Ser Tyr Ala Pro Ser Arg
            20                  25                  30

Pro Arg Thr Ala Ala Pro Ala Val Val Leu Pro Ser Pro Tyr Pro Phe
        35                  40                  45

Ala Pro Val Ala Ala Gln Arg Pro Ser Arg Phe Val Cys Lys Cys Lys
50                  55                  60

Asn Val Val Asp Glu Val Ile Val Ala Asp Glu Lys Asn Trp Asp Asn
65                  70                  75                  80

Met Val Ile Ala Cys Glu Ser Pro Val Leu Val Glu Phe Trp Ala Pro
                85                  90                  95

Trp Cys Gly Pro Cys Arg Met Ile Ala Pro Val Ile Asp Glu Leu Ala
            100                 105                 110

Lys Asp Tyr Met Gly Lys Ile Lys Cys Cys Lys Val Asn Thr Asp Asp
        115                 120                 125

Cys Pro Asn Ile Ala Ser Thr Tyr Gly Ile Arg Ser Ile Pro Thr Val
130                 135                 140

Leu Met Phe Lys Asp Gly Glu Lys Lys Glu Ser Val Ile Gly Ala Val
145                 150                 155                 160

Pro Lys Thr Thr Leu Cys Thr Ile Ile Asp Lys Tyr Ile Gly Ser
                165                 170                 175

<210> SEQ ID NO 25
<211> LENGTH: 181
<212> TYPE: PRT
<213> ORGANISM: Brachypodium distachyon
<220> FEATURE:
<221> NAME/KEY: MISC_FEATURE
<222> LOCATION: (1)..(181)
<223> OTHER INFORMATION: Thioredoxin

<400> SEQUENCE: 25

Met Ala Leu Glu Thr Cys Phe Arg Ala Trp Ala Leu His Ala Pro Gln
1               5                   10                  15

Ala Gly Gly Val Arg Asp Arg Pro Ser Gly Ile Ser Ser Ser Ser Tyr
            20                  25                  30

Ala Pro Ser Arg Pro Arg Thr Thr Ala Ala Ala Val Val Ser Pro
        35                  40                  45

Ser Pro Ser Ala Leu Gln Gln Leu Ala Pro Arg Arg Pro Ser Arg
50                  55                  60

Phe Val Cys His Cys Lys Asn Ala Val Asp Val Val Val Ala Asp
65                  70                  75                  80

Glu Lys Asn Trp Glu Ser Met Val Ile Ala Ser Glu Ala Pro Val Leu
                85                  90                  95

Val Glu Phe Trp Ala Pro Trp Cys Gly Pro Cys Arg Met Ile Ala Pro
            100                 105                 110

Val Ile Asp Glu Leu Ala Lys Asp Tyr Val Gly Lys Ile Lys Cys Cys
        115                 120                 125

Lys Val Asn Thr Asp Asp Cys Pro Asn Ile Ala Ser Thr Tyr Gly Ile
```

```
                    130                 135                 140

Arg Ser Ile Pro Thr Val Leu Met Phe Lys Asp Gly Glu Lys Glu
145                 150                 155                 160

Ser Val Ile Gly Ala Val Pro Lys Thr Thr Leu Ser Gly Ile Ile Asp
                    165                 170                 175

Lys Tyr Val Ala Ala
            180
```

<210> SEQ ID NO 26
<211> LENGTH: 172
<212> TYPE: PRT
<213> ORGANISM: Oryza sativa
<220> FEATURE:
<221> NAME/KEY: MISC_FEATURE
<222> LOCATION: (1)..(172)
<223> OTHER INFORMATION: Thioredoxin

<400> SEQUENCE: 26

```
Met Ala Leu Glu Thr Cys Phe Arg Ala Trp Ala Thr Leu His Ala Pro
1               5                   10                  15

Gln Pro Pro Ser Ser Gly Gly Ser Arg Asp Arg Leu Leu Leu Ser Gly
                20                  25                  30

Ala Gly Ser Ser Gln Ser Lys Pro Arg Leu Ser Val Ala Ser Pro Ser
            35                  40                  45

Pro Leu Arg Pro Ala Ser Arg Phe Ala Cys Gln Cys Ser Asn Val Val
        50                  55                  60

Asp Glu Val Val Ala Asp Glu Lys Asn Trp Asp Ser Met Val Leu
65                  70                  75                  80

Gly Ser Glu Ala Pro Val Leu Val Glu Phe Trp Ala Pro Trp Cys Gly
                85                  90                  95

Pro Cys Arg Met Ile Ala Pro Val Ile Asp Glu Leu Ala Lys Glu Tyr
                100                 105                 110

Val Gly Lys Ile Lys Cys Cys Lys Val Asn Thr Asp Asp Ser Pro Asn
            115                 120                 125

Ile Ala Thr Asn Tyr Gly Ile Arg Ser Ile Pro Thr Val Leu Met Phe
        130                 135                 140

Lys Asn Gly Glu Lys Lys Glu Ser Val Ile Gly Ala Val Pro Lys Thr
145                 150                 155                 160

Thr Leu Ala Thr Ile Ile Asp Lys Tyr Val Ser Ser
                165                 170
```

<210> SEQ ID NO 27
<211> LENGTH: 182
<212> TYPE: PRT
<213> ORGANISM: Phoenix dactylifera
<220> FEATURE:
<221> NAME/KEY: MISC_FEATURE
<222> LOCATION: (1)..(182)
<223> OTHER INFORMATION: Thioredoxin

<400> SEQUENCE: 27

```
Met Ala Leu Glu Thr Cys Phe Gln Met Ser Thr Ile Ala Ser Thr Thr
1               5                   10                  15

Pro Thr Asn Ser Arg Ala Arg Phe Phe Ser Tyr Lys Glu Lys His Asn
                20                  25                  30

Leu Pro Ala Asn Ser Gly Leu Lys Arg Ala Ile Ser Ala Leu Ser Ser
            35                  40                  45

Ser Ser Thr Pro Ser Thr Ser Ile Pro Ser Ala Asn Asn Arg Arg Lys
        50                  55                  60
```

```
Arg Phe Ile Cys Gln Ala Lys Asn Ala Val Asp Glu Val Leu Val Val
 65                  70                  75                  80

Asn Asp Ala Asn Trp Asp Ser Met Val Ile Gly Cys Gly Thr Pro Val
                 85                  90                  95

Leu Val Asp Phe Trp Ala Pro Trp Cys Gly Pro Cys Arg Met Ile Ala
            100                 105                 110

Pro Ile Ile Asp Glu Leu Ala Lys Asp Tyr Ala Gly Lys Ile Ile Cys
        115                 120                 125

Cys Lys Val Asn Thr Asp Glu Cys Pro Asn Ile Ala Ser Lys Tyr Gly
    130                 135                 140

Ile Arg Ser Ile Pro Thr Val Leu Phe Lys Asn Gly Asp Lys Lys
145                 150                 155                 160

Glu Ser Val Ile Gly Ala Val Pro Lys Ser Thr Leu Cys Gly Ile Ile
                165                 170                 175

Asp Lys Tyr Leu Glu Met
            180
```

<210> SEQ ID NO 28
<211> LENGTH: 188
<212> TYPE: PRT
<213> ORGANISM: Elaeis guineensis
<220> FEATURE:
<221> NAME/KEY: MISC_FEATURE
<222> LOCATION: (1)..(188)
<223> OTHER INFORMATION: Thioredoxin

<400> SEQUENCE: 28

```
Met Ala Leu Glu Ser Cys Phe Gln Met Ser Thr Ile Ala Ser Thr Thr
  1               5                  10                  15

Lys Thr Thr Ser Gly Ala Arg Phe Leu His Ala His His Pro Phe Ser
                 20                  25                  30

Tyr Lys Glu Lys His Asn Leu Pro Ala Tyr Ser Gly Leu Lys Arg Thr
             35                  40                  45

Ile Ser Ala Leu Ser Thr Ser Ser Thr Pro Ser Thr Ser Ile Ser Leu
 50                  55                  60

Val Asn Asn Arg Arg Asn Arg Phe Ile Cys Arg Ala Lys Asn Ala Val
 65                  70                  75                  80

Asp Glu Val Leu Val Ala Asn Asp Ala Asn Trp Asp Asn Met Val Ile
                 85                  90                  95

Gly Cys Glu Thr Pro Val Leu Val Gly Phe Trp Ala Pro Trp Cys Gly
            100                 105                 110

Pro Cys Arg Met Ile Ala Pro Met Ile Asp Glu Leu Ala Lys Asp Tyr
        115                 120                 125

Ala Gly Lys Ile Ile Cys Cys Lys Val Asn Thr Asp Asp Cys Pro Asn
    130                 135                 140

Ile Ala Ser Lys Tyr Gly Ile Arg Ser Ile Pro Thr Val Leu Leu Phe
145                 150                 155                 160

Lys Asn Gly Asp Lys Lys Glu Ser Val Ile Gly Ala Val Pro Lys Ser
                165                 170                 175

Thr Leu Cys Gly Ile Ile Asp Lys Tyr Leu Glu Met
            180                 185
```

<210> SEQ ID NO 29
<211> LENGTH: 189
<212> TYPE: PRT
<213> ORGANISM: Phoenix dactylifera
<220> FEATURE:

<210> SEQ ID NO 29
...
<221> NAME/KEY: MISC_FEATURE
<222> LOCATION: (1)..(189)
<223> OTHER INFORMATION: Thioredoxin

<400> SEQUENCE: 29

```
Met Ala Phe Glu Thr Cys Phe Gln Met Ser Thr Ile Ala Ser Thr Thr
1               5                   10                  15

Thr Ala Thr Ser Arg Ala Arg Phe Leu His Ala His His Pro Phe Ser
            20                  25                  30

Tyr Lys Glu Arg His Ile Trp Pro Ala Ser His Gly Ser Lys Arg Ala
        35                  40                  45

Ile Ser Ser Leu Ser Ser Pro Thr Pro Ser Thr Ser Ile Pro Ser
50                  55                  60

Val Asn Asn His Arg Ser Arg Phe Val Cys Gln Ala Lys Asn Ala Val
65                  70                  75                  80

Asp Glu Val Leu Val Ala Asn Asp Ala Asn Trp Asp Asn Met Val Ile
                85                  90                  95

Gly Cys Glu Thr Pro Val Val Leu Val Glu Phe Trp Ala Pro Trp Cys
            100                 105                 110

Gly Pro Cys Arg Met Ile Thr Pro Val Ile Asp Glu Leu Ala Lys Asp
        115                 120                 125

Tyr Ala Gly Lys Ile Ile Cys Cys Lys Val Asn Thr Asp Asp Cys Pro
130                 135                 140

Asn Ile Ala Ser Lys Tyr Gly Ile Arg Ser Ile Pro Thr Val Leu Leu
145                 150                 155                 160

Phe Lys Ser Gly Asp Lys Lys Glu Ser Val Ile Gly Ala Val Pro Lys
                165                 170                 175

Asn Thr Leu Cys Asp Ile Ile Asp Lys Tyr Leu Glu Met
            180                 185
```

<210> SEQ ID NO 30
<211> LENGTH: 188
<212> TYPE: PRT
<213> ORGANISM: Elaeis guineensis
<220> FEATURE:
<221> NAME/KEY: MISC_FEATURE
<222> LOCATION: (1)..(188)
<223> OTHER INFORMATION: Thioredoxin

<400> SEQUENCE: 30

```
Met Ala Leu Glu Thr Cys Phe Gln Met Ser Thr Val Ala Ser Thr Thr
1               5                   10                  15

Thr Thr Ala Ser Arg Ala Arg Phe Leu Gln Ala His His Phe Ser
            20                  25                  30

Cys Lys Glu Lys His Ile Trp Pro Ala Ser Ser Gly Phe Lys Arg Ala
        35                  40                  45

Ile Ser Ser Leu Pro Ser Ser Pro Asn Pro Ser Met Ser Ile Leu Pro
50                  55                  60

Val Asn Asn Arg Cys Thr Arg Phe Ile Cys Gln Ala Lys Asn Val Val
65                  70                  75                  80

Asp Glu Val Leu Val Ala Asn Glu Ala Asn Trp Asp Asn Met Val Ile
                85                  90                  95

Gly Cys Glu Ala Pro Val Leu Val Asp Phe Trp Ala Pro Trp Cys Gly
            100                 105                 110

Pro Cys Arg Met Ile Ala Pro Val Ile Asp Glu Leu Ala Lys Asp Tyr
        115                 120                 125

Ala Gly Lys Ile Val Cys Cys Lys Val Asn Thr Asp Asp Cys Pro Asn
```

```
                    130                 135                 140
Ile Ala Ser Lys Tyr Gly Ile Arg Ser Ile Pro Thr Val Leu Leu Phe
145                 150                 155                 160

Lys Asn Gly Asp Lys Lys Glu Ser Val Ile Gly Ala Val Pro Lys Ser
                165                 170                 175

Thr Leu Cys Asp Ile Ile Asp Lys Tyr Leu Glu Met
                180                 185
```

<210> SEQ ID NO 31
<211> LENGTH: 110
<212> TYPE: PRT
<213> ORGANISM: Triticum urartu
<220> FEATURE:
<221> NAME/KEY: MISC_FEATURE
<222> LOCATION: (1)..(110)
<223> OTHER INFORMATION: Thioredoxin

<400> SEQUENCE: 31

```
Met Ala His Ala Val Ile Val Ala Asp Glu Lys Asn Trp Asp Asn Met
1               5                   10                  15

Val Ile Ala Cys Glu Ser Pro Val Leu Val Glu Phe Trp Ala Pro Trp
                20                  25                  30

Cys Gly Pro Cys Arg Met Ile Ala Pro Val Ile Asp Glu Leu Ala Lys
            35                  40                  45

Asp Tyr Val Gly Lys Ile Lys Cys Cys Lys Val Asn Thr Asp Asp Cys
        50                  55                  60

Pro Asn Ile Ala Ser Thr Tyr Gly Ile Arg Ser Ile Pro Thr Val Leu
65                  70                  75                  80

Met Phe Lys Asp Gly Glu Lys Lys Glu Ser Val Ile Gly Ala Val Pro
                85                  90                  95

Lys Thr Thr Leu Cys Thr Ile Ile Asp Lys Tyr Ile Gly Ser
                100                 105                 110
```

<210> SEQ ID NO 32
<211> LENGTH: 183
<212> TYPE: PRT
<213> ORGANISM: Vitis vinifera
<220> FEATURE:
<221> NAME/KEY: MISC_FEATURE
<222> LOCATION: (1)..(183)
<223> OTHER INFORMATION: Thioredoxin

<400> SEQUENCE: 32

```
Met Ala Leu Glu Asn Cys Phe Gln Val Ser Thr Val Ser Cys Ala Arg
1               5                   10                  15

Ala Gly Val Leu Gln Ser His His Pro Phe Ser Ala Lys Glu Lys Leu
                20                  25                  30

Asn Leu Pro Thr Cys Lys Gly Val Lys Pro Ser Ile Leu Ser Phe Ser
            35                  40                  45

Ser Ser Pro Ser Ser Leu Asp Tyr Ser Phe His Arg Ile Cys Arg Lys
        50                  55                  60

Ser Arg Ile Val Cys Lys Ala Arg Glu Ala Val Asp Glu Val Gln Val
65                  70                  75                  80

Val Thr Asp Ser Ser Trp Ser Asn Val Val Ile Ala Ser Glu Asn Pro
                85                  90                  95

Val Leu Val Glu Phe Trp Ala Pro Trp Cys Gly Pro Cys Arg Met Ile
                100                 105                 110

Ala Pro Val Ile Asp Glu Leu Ala Lys Glu Tyr Ala Gly Lys Ile Val
            115                 120                 125
```

```
Cys Cys Lys Val Asn Thr Asp Asp Cys Pro Asn Ile Ala Thr Gln Tyr
            130                 135                 140

Gly Ile Arg Ser Ile Pro Thr Val Leu Phe Phe Lys Asn Gly Glu Arg
145                 150                 155                 160

Lys Glu Ser Val Ile Gly Ala Val Pro Lys Ser Thr Leu Thr Ala Thr
                165                 170                 175

Ile Glu Lys Tyr Val Asp Met
            180

<210> SEQ ID NO 33
<211> LENGTH: 181
<212> TYPE: PRT
<213> ORGANISM: Glycine max
<220> FEATURE:
<221> NAME/KEY: MISC_FEATURE
<222> LOCATION: (1)..(181)
<223> OTHER INFORMATION: Thioredoxin

<400> SEQUENCE: 33

Met Ala Leu Glu Asn Cys Leu Arg Val Thr Thr Val Gly Thr Ala Thr
1               5                   10                  15

Pro Gln Cys Phe Ser Pro Phe Phe Pro Ser Ser Arg Asp Lys Leu Val
            20                  25                  30

Phe Pro Thr His Arg Gly Phe Lys Lys Ser Leu Gln Asn Ser Thr Leu
        35                  40                  45

Ser Tyr Pro Tyr Leu Tyr Ser Thr Gly Ala Ala Tyr Arg Lys Ser Arg
    50                  55                  60

Phe Val Cys Asn Ala Arg Glu Ala Val Asn Glu Val Lys Val Val Thr
65                  70                  75                  80

Asp Ser Ser Trp Asn Asn Leu Val Ile Ala Ser Glu Thr Pro Val Leu
                85                  90                  95

Val Glu Phe Trp Ala Pro Trp Cys Gly Pro Cys Arg Met Ile Ala Pro
            100                 105                 110

Ala Ile Asp Glu Leu Ala Lys Glu Tyr Ala Gly Lys Ile Ala Cys Phe
        115                 120                 125

Lys Leu Asn Thr Asp Asp Ser Pro Asn Ile Ala Thr Gln Tyr Gly Ile
130                 135                 140

Arg Ser Ile Pro Thr Val Leu Phe Phe Lys Asn Gly Glu Lys Lys Glu
145                 150                 155                 160

Ser Ile Ile Gly Ala Val Pro Lys Ser Thr Leu Ser Ala Thr Val Glu
                165                 170                 175

Lys Tyr Val Asp Ser
            180

<210> SEQ ID NO 34
<211> LENGTH: 180
<212> TYPE: PRT
<213> ORGANISM: Pyrus x bretschneideri
<220> FEATURE:
<221> NAME/KEY: MISC_FEATURE
<222> LOCATION: (1)..(180)
<223> OTHER INFORMATION: Thioredoxin

<400> SEQUENCE: 34

Met Ala Leu Glu Asn Cys Leu Gln Leu Ser Thr Val Cys Thr Thr Arg
1               5                   10                  15

Val Gly Ala Ala Ala His His Pro Phe Ser Ser Thr Asp Lys Phe Val
            20                  25                  30
```

```
Val Pro Thr Ser Asn Gly Leu Lys Lys Ser Ala Leu Lys Phe Ser Ser
        35                  40                  45

Ser Ser Ser Ser Phe Ser Arg Ser Gly Lys Ser Gln Lys Ser Arg Phe
 50                  55                  60

Ile Cys Lys Ala Arg Glu Ala Val Asn Glu Val Gln Val Val Asn Asp
 65                  70                  75                  80

Ser Ser Trp Asn Thr Leu Val Ile Ala Ser Glu Asn Pro Val Leu Val
                 85                  90                  95

Glu Phe Trp Ala Pro Trp Cys Gly Pro Cys Arg Met Ile Ala Pro Val
                100                 105                 110

Ile Asp Glu Leu Ala Lys Glu Tyr Ala Gly Lys Ile Ser Cys Phe Lys
                115                 120                 125

Leu Asn Thr Asp Glu Ser Pro Asn Thr Ala Thr Gln Tyr Gly Ile Arg
        130                 135                 140

Ser Ile Pro Thr Val Leu Phe Phe Lys Asn Gly Glu Lys Lys Glu Ser
145                 150                 155                 160

Val Ile Gly Ala Val Pro Lys Ser Thr Leu Ser Ala Thr Ile Glu Lys
                165                 170                 175

Tyr Val Asp Leu
        180

<210> SEQ ID NO 35
<211> LENGTH: 180
<212> TYPE: PRT
<213> ORGANISM: Prunus persica
<220> FEATURE:
<221> NAME/KEY: MISC_FEATURE
<222> LOCATION: (1)..(180)
<223> OTHER INFORMATION: Thioredoxin

<400> SEQUENCE: 35

Met Ala Leu Glu Asn Cys Leu Gln Leu Ser Thr Val Cys Thr Thr Arg
1               5                   10                  15

Val Gly Ala Ala Gln Cys Tyr Gln Pro Phe Ser Ser Arg Glu Arg Leu
                20                  25                  30

Ile Val Pro Thr Cys Asn Gly Leu Lys Lys Ser Val Leu Lys Phe Ser
        35                  40                  45

Ser Ser Ser Ser Phe Ala Pro Ser Asn Lys Ser His Arg Ser Arg Phe
 50                  55                  60

Ile Cys Lys Ala Arg Glu Ala Val Asn Glu Val Gln Val Val Asn Asp
 65                  70                  75                  80

Ser Ser Trp Asn Asn Leu Val Ile Ala Ser Glu Asp Pro Val Leu Val
                 85                  90                  95

Glu Phe Trp Ala Pro Trp Cys Gly Pro Cys Arg Met Ile Ala Pro Val
                100                 105                 110

Ile Asp Glu Leu Ala Lys Glu Tyr Ala Gly Lys Ile Ala Cys Phe Lys
                115                 120                 125

Leu Asn Thr Asp Asp Ser Pro Asn Ile Ala Thr Gln Tyr Gly Ile Arg
        130                 135                 140

Ser Ile Pro Thr Val Leu Phe Phe Lys Asn Gly Glu Lys Lys Glu Ser
145                 150                 155                 160

Val Ile Gly Ala Val Pro Lys Ser Thr Leu Ser Ala Thr Ile Glu Lys
                165                 170                 175

Tyr Val Asp Leu
        180
```

-continued

```
<210> SEQ ID NO 36
<211> LENGTH: 182
<212> TYPE: PRT
<213> ORGANISM: Cajanus cajan
<220> FEATURE:
<221> NAME/KEY: MISC_FEATURE
<222> LOCATION: (1)..(182)
<223> OTHER INFORMATION: Thioredoxin

<400> SEQUENCE: 36

Met Ala Met Glu Asn Cys Leu Arg Leu Thr Thr Val Ala Thr Thr Thr
1               5                   10                  15

Pro Gln Cys Leu Ser Pro Phe Phe Pro Thr Ser Arg Glu Lys Leu Val
            20                  25                  30

Phe Pro Thr Gln Thr Gly Phe Lys Lys Ser Met Leu Asn Ser Lys Val
        35                  40                  45

Ser Tyr Pro Ser Ser Leu Tyr Ser Thr Gly Ala Thr Tyr Lys Lys Ser
    50                  55                  60

Arg Phe Val Cys Lys Ala Arg Glu Ala Val Asn Glu Val Lys Val Val
65                  70                  75                  80

Asn Asp Ser Ser Trp Asn Asn Leu Val Ile Ala Ser Asp Thr Pro Val
                85                  90                  95

Leu Val Glu Phe Trp Ala Pro Trp Cys Gly Pro Cys Arg Met Ile Ala
            100                 105                 110

Pro Val Ile Asp Glu Leu Ala Lys Glu Tyr Ala Gly Lys Ile Ala Cys
        115                 120                 125

Tyr Lys Leu Asn Thr Asp Asp Ser Pro Asn Thr Ala Thr Gln Tyr Gly
    130                 135                 140

Ile Arg Ser Ile Pro Thr Val Leu Phe Phe Lys Asn Gly Glu Lys Lys
145                 150                 155                 160

Glu Ser Ile Ile Gly Ala Val Pro Lys Ser Thr Leu Ser Ala Thr Val
                165                 170                 175

Glu Lys Tyr Val Asp Ser
            180

<210> SEQ ID NO 37
<211> LENGTH: 185
<212> TYPE: PRT
<213> ORGANISM: Glycine max
<220> FEATURE:
<221> NAME/KEY: MISC_FEATURE
<222> LOCATION: (1)..(185)
<223> OTHER INFORMATION: Thioredoxin

<400> SEQUENCE: 37

Met Gly Met Glu Asn Cys Leu Arg Val Thr Thr Val Gly Thr Ala Thr
1               5                   10                  15

Pro Gln Cys Leu Ser Pro Phe Phe Pro Ser Ser Arg Asp Lys Leu Val
            20                  25                  30

Phe Pro Thr His Arg Gly Phe Lys Lys Ser Leu Gln Asn Ser Thr Leu
        35                  40                  45

Ser Cys Pro Ser Leu Tyr Ser Thr Gly Ala Ala Tyr Arg Arg Ser Arg
    50                  55                  60

Phe Val Cys Asn Ala Arg Glu Ala Val Asn Glu Val Lys Val Val Thr
65                  70                  75                  80

Asp Ser Ser Trp Asn Asn Leu Val Ile Ala Ser Glu Thr Pro Val Leu
                85                  90                  95

Val Glu Phe Trp Ala Pro Trp Cys Gly Pro Cys Arg Met Ile Ala Pro
            100                 105                 110
```

Val Ile Asp Glu Leu Ala Lys Asp Tyr Ala Gly Lys Ile Ala Cys Tyr
        115                 120                 125

Lys Leu Asn Thr Asp Asp Ser Pro Asn Ile Ala Thr Gln Tyr Gly Ile
130                 135                 140

Arg Ser Ile Pro Thr Val Leu Phe Phe Lys Asn Gly Glu Lys Lys Glu
145                 150                 155                 160

Ser Ile Ile Gly Ala Val Pro Lys Ser Thr Leu Ser Ala Thr Val Glu
                165                 170                 175

Asn Met Leu Asn Tyr Lys Leu Arg Lys
        180                 185

<210> SEQ ID NO 38
<211> LENGTH: 180
<212> TYPE: PRT
<213> ORGANISM: Malus domestica
<220> FEATURE:
<221> NAME/KEY: MISC_FEATURE
<222> LOCATION: (1)..(180)
<223> OTHER INFORMATION: Thioredoxin
<220> FEATURE:
<223> OTHER INFORMATION: Xaa represents any amino acid

<400> SEQUENCE: 38

Met Ala Leu Glu Asn Cys Leu Gln Leu Ser Thr Val Cys Thr Thr Arg
1               5                   10                  15

Val Gly Ala Ala Ala His His Pro Phe Ser Ser Thr Asp Lys Phe Val
                20                  25                  30

Val Pro Thr Xaa Asn Gly Leu Lys Lys Ser Ala Leu Lys Phe Ser Ser
            35                  40                  45

Ser Ser Ser Ser Phe Pro Arg Ser Gly Lys Ser Gln Lys Ser Arg Phe
50                  55                  60

Ile Cys Lys Ala Arg Glu Ala Val Asn Glu Val Gln Val Val Asn Asp
65                  70                  75                  80

Ser Ser Trp Asn Thr Leu Val Ile Ala Ser Glu Asn Pro Val Leu Val
                85                  90                  95

Glu Phe Trp Ala Pro Trp Cys Gly Pro Cys Arg Met Ile Ala Pro Val
            100                 105                 110

Ile Asp Glu Leu Ala Lys Glu Tyr Ala Gly Lys Ile Ser Cys Phe Lys
        115                 120                 125

Leu Asn Thr Asp Glu Ser Pro Asn Thr Ala Thr Gln Tyr Gly Ile Arg
130                 135                 140

Ser Ile Pro Thr Val Leu Phe Phe Lys Asn Gly Glu Lys Lys Glu Ser
145                 150                 155                 160

Val Ile Gly Ala Val Pro Lys Ser Thr Leu Ser Ala Thr Ile Glu Lys
                165                 170                 175

Tyr Val Asp Leu
        180

<210> SEQ ID NO 39
<211> LENGTH: 236
<212> TYPE: PRT
<213> ORGANISM: Prunus mume
<220> FEATURE:
<221> NAME/KEY: MISC_FEATURE
<222> LOCATION: (1)..(236)
<223> OTHER INFORMATION: Thioredoxin

<400> SEQUENCE: 39

Met Gln Pro Arg Gln Asn Arg Lys Phe Lys Glu Glu Ile Cys Thr Asn

```
           1               5                   10                  15
        Cys Cys Arg Asn Leu Pro Ile Arg Lys Ala Thr Phe Ser Val Gln His
                        20                  25                  30

Pro Ile His Cys Lys Lys Ile Tyr Leu Ala Lys Lys Arg Glu Arg Glu
                        35                  40                  45

Arg Glu Arg Glu Arg Glu Val Met Ala Leu Glu Asn Cys Leu Gln
            50                  55                  60

Leu Ser Thr Val Cys Thr Thr Arg Val Gly Ala Ala Gln Cys Tyr Gln
        65                  70                  75                  80

Pro Phe Ser Ser Arg Glu Lys Leu Ile Val Pro Thr Cys Asn Gly Leu
                        85                  90                  95

Lys Lys Ser Val Leu Lys Phe Ser Ser Ser Ser Phe Ala Pro Ser
                        100                 105                 110

Asn Lys Ser His Arg Ser Arg Phe Ile Cys Lys Ala Arg Glu Ala Val
                        115                 120                 125

Asn Glu Val Gln Val Val Asn Asp Ser Ser Trp Asn Asn Leu Val Ile
                        130                 135                 140

Ala Ser Glu Asn Pro Val Leu Val Glu Phe Trp Ala Pro Trp Cys Gly
        145                 150                 155                 160

Pro Cys Arg Met Ile Ala Pro Val Ile Asp Glu Leu Ala Lys Glu Tyr
                        165                 170                 175

Ala Gly Lys Ile Ala Cys Phe Lys Leu Asn Thr Asp Asp Ser Pro Asn
                        180                 185                 190

Ile Ala Thr Gln Tyr Gly Ile Arg Ser Ile Pro Thr Val Leu Phe Phe
                        195                 200                 205

Lys Asn Gly Glu Lys Lys Glu Ser Val Ile Gly Ala Val Pro Lys Ser
                        210                 215                 220

Thr Leu Ser Ala Thr Ile Glu Lys Tyr Val Asp Leu
        225                 230                 235

<210> SEQ ID NO 40
        <211> LENGTH: 182
        <212> TYPE: PRT
        <213> ORGANISM: Arachis duranensis
        <220> FEATURE:
        <221> NAME/KEY: MISC_FEATURE
        <222> LOCATION: (1)..(182)
        <223> OTHER INFORMATION: Thioredoxin

<400> SEQUENCE: 40

Met Ala Leu Glu Asn Cys Leu Arg Leu Ser Thr Thr Val Gly Thr Ala
        1               5                   10                  15

Arg Ile Gln Cys Leu Ser Pro Leu Ser Ser Arg Lys Lys Leu Val Phe
                        20                  25                  30

Ser Ser Tyr Arg Gly Phe Asn Lys Ser Met Leu His Ser Thr Val Ser
                        35                  40                  45

Asn Ser Asn Pro Ser Leu Tyr Ser Thr Ala Gly Thr Ser Arg Lys Ser
                        50                  55                  60

Ser Phe Val Cys Asn Ala Arg Glu Lys Val Asn Glu Val Gln Val Val
        65                  70                  75                  80

Thr Asp Ser Ser Trp Asn Lys Leu Val Ile Gly Ser Glu Thr Pro Val
                        85                  90                  95

Leu Val Glu Phe Trp Ala Pro Trp Cys Gly Pro Cys Arg Met Ile Ala
                        100                 105                 110

Pro Ile Ile Asp Glu Leu Ala Lys Glu Tyr Ala Gly Lys Ile Ala Cys
                        115                 120                 125
```

```
Tyr Lys Ile Asn Thr Asp Asp Cys Pro Asn Ile Ala Thr Gln Tyr Gly
        130                 135                 140

Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Ala Thr Leu
                165                 170                 175

Asp Lys Tyr Val Asp Ile
            180

<210> SEQ ID NO 41
<211> LENGTH: 182
<212> TYPE: PRT
<213> ORGANISM: Arachis ipaensis
<220> FEATURE:
<221> NAME/KEY: MISC_FEATURE
<222> LOCATION: (1)..(182)
<223> OTHER INFORMATION: Thioredoxin

<400> SEQUENCE: 41

Met Ala Leu Glu Asn Cys Leu Arg Leu Ser Thr Val Gly Thr Ala
1               5                   10                  15

Arg Ile Gln Cys Leu Ser Pro Leu Ser Ser Arg Lys Lys Leu Val Phe
                20                  25                  30

Ser Ser Tyr Arg Gly Phe Asn Lys Ser Met Leu Tyr Ser Thr Val Ser
            35                  40                  45

Asn Ser Asn Pro Ser Leu Tyr Ser Thr Ala Gly Thr Ser Arg Lys Ser
        50                  55                  60

Ser Phe Val Cys Asn Ala Arg Glu Lys Val Asn Glu Val Gln Val Val
65                  70                  75                  80

Thr Asp Ser Ser Trp Asn Lys Leu Val Ile Gly Ser Glu Thr Pro Val
                85                  90                  95

Leu Val Glu Phe Trp Ala Pro Trp Cys Gly Pro Cys Arg Met Ile Ala
                100                 105                 110

Pro Ile Ile Asp Glu Leu Ala Lys Glu Tyr Ala Gly Lys Ile Ala Cys
            115                 120                 125

Tyr Lys Ile Asn Thr Asp Asp Cys Pro Asn Ile Ala Thr Gln Tyr Gly
        130                 135                 140

Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Ala Thr Leu
                165                 170                 175

Asp Lys Tyr Val Asp Ile
            180

<210> SEQ ID NO 42
<211> LENGTH: 179
<212> TYPE: PRT
<213> ORGANISM: Cicer arietinum
<220> FEATURE:
<221> NAME/KEY: MISC_FEATURE
<222> LOCATION: (1)..(179)
<223> OTHER INFORMATION: Thioredoxin

<400> SEQUENCE: 42

Met Ala Leu Glu Asn Cys Leu Arg Val Ser Thr Ala Arg Pro His Cys
1               5                   10                  15

Leu Pro Pro Leu Phe Ser Ser Ser Arg Glu Lys Leu Val Phe Ser Ala
                20                  25                  30
```

```
Gln Arg Gly Gly Phe Lys Lys Ser Val Gln Asn Ala Thr Val Ser Leu
            35                  40                  45

Pro Ser Leu Tyr Ser Thr Gly Val Ala Tyr Arg Lys Ser Arg Phe Val
 50                  55                  60

Cys Asn Ala Arg Glu Ala Leu Asn Glu Val Gly Val Thr Asp Ala
 65                  70                  75                  80

Asn Trp Asn Asp Leu Val Leu Ala Ser Glu Ile Pro Val Leu Val Asp
                 85                  90                  95

Phe Trp Ala Ser Trp Cys Gly Pro Cys Arg Met Ile Ala Pro Ile Leu
                100                 105                 110

Asp Glu Leu Ala Lys Glu Tyr Ala Gly Lys Ile Ala Cys Tyr Lys Leu
                115                 120                 125

Asn Thr Asp Asp Cys Pro Asn Ile Ala Thr Lys Tyr Gly Ile Arg Ser
            130                 135                 140

Ile Pro Thr Val Leu Phe Phe Lys Asn Gly Glu Lys Lys Glu Ser Val
145                 150                 155                 160

Ile Gly Ala Val Pro Lys Ser Thr Leu Ser Ala Thr Leu Glu Lys Tyr
                    165                 170                 175

Ile Glu Ala

<210> SEQ ID NO 43
<211> LENGTH: 184
<212> TYPE: PRT
<213> ORGANISM: Cajanus cajan
<220> FEATURE:
<221> NAME/KEY: MISC_FEATURE
<222> LOCATION: (1)..(184)
<223> OTHER INFORMATION: Thioredoxin

<400> SEQUENCE: 43

Met Ala Leu Glu Asn Cys Val Arg Val Ala Thr Val Gly Thr Gly Ala
 1               5                  10                  15

Arg Pro Gln Gln Cys Leu Leu His Pro Phe Ser Lys Arg Glu Lys Leu
                20                  25                  30

Val Phe Pro Thr Phe Gly Gly Phe Lys Lys Ser Leu Ser Lys Ser Thr
            35                  40                  45

Leu Ser Asn Ala Ser Ser Leu Tyr Ser Ala Ala Gly Lys Asn Arg
 50                  55                  60

Lys Ser Arg Phe Ile Cys Lys Ala Arg Glu Ala Val Asn Glu Val Arg
 65                  70                  75                  80

Val Val Thr Asp Ser Ser Trp Asn Ser Leu Val Ile Glu Ser Glu Thr
                 85                  90                  95

Pro Val Leu Val Asp Phe Trp Ala Pro Trp Cys Gly Pro Cys Arg Met
                100                 105                 110

Ile Ala Pro Ile Ile Asp Glu Leu Ala Lys Glu Tyr Ala Gly Lys Ile
            115                 120                 125

Val Cys Tyr Lys Leu Asn Thr Asp Asp Cys Pro Asn Ile Ala Thr Gln
            130                 135                 140

Tyr Gly Ile Arg Ser Ile Pro Thr Val Leu Phe Phe Lys Asn Gly Glu
145                 150                 155                 160

Lys Lys Glu Ser Ile Ile Gly Ala Val Pro Lys Ser Thr Leu Ser Ala
                    165                 170                 175

Thr Val Glu Lys Tyr Ala Asp Ile
                180

<210> SEQ ID NO 44
```

```
<211> LENGTH: 175
<212> TYPE: PRT
<213> ORGANISM: Medicago truncatula
<220> FEATURE:
<221> NAME/KEY: MISC_FEATURE
<222> LOCATION: (1)..(175)
<223> OTHER INFORMATION: Thioredoxin

<400> SEQUENCE: 44

Met Ala Leu Glu Asn Cys Leu Arg Val Ser Thr Ala Arg Pro Gln Cys
1               5                   10                  15

Leu Pro Ser Leu Phe Pro Thr Ser Arg Glu Lys Val Val Phe Ser Ala
            20                  25                  30

Gln Arg Ala Gly Phe Lys Lys Ser Val Leu Asn Ser Thr Leu Ser Phe
        35                  40                  45

Pro Ser Gly Val Ala Tyr Arg Lys Ser Arg Phe Ile Cys Asn Ala Arg
    50                  55                  60

Glu Ala Val Asn Glu Val Gly Ala Val Thr Asp Ser Ser Trp Asn Glu
65                  70                  75                  80

Leu Val Leu Ala Ser Asp Thr Pro Val Leu Val Asp Phe Trp Ala Pro
                85                  90                  95

Trp Cys Gly Pro Cys Arg Met Ile Ala Pro Ile Ile Asp Glu Leu Ala
            100                 105                 110

Lys Glu Tyr Ala Gly Lys Ile Ser Cys Tyr Lys Leu Asn Thr Asp Glu
        115                 120                 125

Asn Pro Asn Ile Ala Thr Lys Tyr Gly Ile Arg Ser Ile Pro Thr Val
    130                 135                 140

Leu Phe Phe Lys Asn Gly Glu Lys Glu Ser Val Ile Gly Ala Val
145                 150                 155                 160

Pro Lys Ser Thr Leu Ser Thr Thr Val Glu Lys Tyr Ile Asp Ala
                165                 170                 175

<210> SEQ ID NO 45
<211> LENGTH: 177
<212> TYPE: PRT
<213> ORGANISM: Vigna radiata
<220> FEATURE:
<221> NAME/KEY: MISC_FEATURE
<222> LOCATION: (1)..(177)
<223> OTHER INFORMATION: Thioredoxin

<400> SEQUENCE: 45

Met Ala Leu Glu Lys Cys Leu Gly Val Thr Thr Val Arg Thr Ala Thr
1               5                   10                  15

Pro His Leu Ser Pro Cys Phe Pro Thr Ser Arg Glu Lys Leu Val Phe
            20                  25                  30

Pro Thr His Thr Ala Phe Lys Lys Ser Met Ser Asn Thr Lys Leu Ser
        35                  40                  45

Tyr Gln Ser Leu Tyr Ser Thr Tyr Arg Lys Ser Arg Phe Val Cys Asn
    50                  55                  60

Ala Arg Glu Ala Val Asn Glu Val Lys Val Val Thr Asp Ser Ser Trp
65                  70                  75                  80

Asn Lys Leu Val Ile Ala Asn Glu Thr Pro Val Leu Val Glu Phe Trp
                85                  90                  95

Ala Pro Trp Cys Gly Pro Cys Arg Met Ile Ala Pro Val Ile Asp Glu
            100                 105                 110

Leu Ala Lys Gln Tyr Gly Asp Lys Ile Ala Cys Tyr Lys Leu Asn Thr
        115                 120                 125
```

```
Asp Asp Ser Pro Asn Ile Ala Thr Gln Tyr Gly Ile Arg Ser Ile Pro
    130                 135                 140

Thr Val Leu Phe Phe Lys Asn Gly Glu Lys Lys Glu Ser Ile Ile Gly
145                 150                 155                 160

Ala Val Pro Lys Ser Thr Leu Ser Ala Thr Ile Glu Lys Tyr Val Asp
                165                 170                 175

Leu

<210> SEQ ID NO 46
<211> LENGTH: 181
<212> TYPE: PRT
<213> ORGANISM: Lotus japonicus
<220> FEATURE:
<221> NAME/KEY: MISC_FEATURE
<222> LOCATION: (1)..(181)
<223> OTHER INFORMATION: Thioredoxin

<400> SEQUENCE: 46

Met Ala Met Glu Ser Cys Leu Gln Val Thr Thr Val Gly Thr Val Ala
1               5                   10                  15

Arg Pro Gln Ser Leu His Pro Phe Ser Ala Arg Glu Lys Val Val Phe
                20                  25                  30

Pro Thr Tyr Arg Gly Phe Lys Lys Cys Phe Ser Lys Ser Ala Thr Ser
            35                  40                  45

Ser Asn Pro Ser Leu Tyr Ser Ala Ala Gly Thr Asn Arg Lys Phe Ser
    50                  55                  60

Val Ile Cys Asn Ala Arg Glu Ala Val Asn Glu Val Lys Val Val Thr
65                  70                  75                  80

Glu Ser Ser Trp Asn Asp Leu Val Ile Ala Ser Glu Ile Pro Val Leu
                85                  90                  95

Val Asp Phe Trp Ala Pro Trp Cys Gly Pro Cys Arg Met Ile Ala Pro
                100                 105                 110

Leu Ile Asp Glu Leu Ala Lys Glu Tyr Ala Gly Lys Ile Ala Cys Tyr
            115                 120                 125

Lys Leu Asn Thr Asp Asp Ser Pro Asn Ile Ala Thr Gln Tyr Gly Ile
    130                 135                 140

Arg Ser Ile Pro Thr Val Leu Phe Phe Lys Asn Gly Glu Lys Lys Glu
145                 150                 155                 160

Ser Val Ile Gly Ala Val Pro Lys Ser Thr Leu Thr Ala Ser Leu Glu
                165                 170                 175

Lys Tyr Ile Ala Ile
            180

<210> SEQ ID NO 47
<211> LENGTH: 177
<212> TYPE: PRT
<213> ORGANISM: Vigna angularis
<220> FEATURE:
<221> NAME/KEY: MISC_FEATURE
<222> LOCATION: (1)..(177)
<223> OTHER INFORMATION: Thioredoxin

<400> SEQUENCE: 47

Met Ala Leu Glu Lys Cys Leu Gly Val Thr Thr Val Arg Thr Ala Thr
1               5                   10                  15

Pro His Leu Ser Pro Cys Phe Pro Thr Ser Arg Glu Lys Leu Leu Phe
                20                  25                  30

Pro Thr His Thr Gly Phe Lys Lys Ser Met Pro Asn Thr Lys Leu Ser
            35                  40                  45
```

-continued

Tyr Gln Ser Leu Tyr Ser Thr Tyr Arg Lys Ser Arg Phe Val Cys Asn
            50                  55                  60

Ala Arg Glu Ala Val Asn Glu Val Lys Glu Val Thr Asp Ser Ser Trp
 65                  70                  75                  80

Asn Lys Leu Val Ile Ala Asn Glu Thr Pro Val Leu Val Glu Phe Trp
                    85                  90                  95

Ala Pro Trp Cys Gly Pro Cys Arg Met Ile Ala Pro Val Ile Asp Glu
                100                 105                 110

Leu Ala Lys Gln Tyr Gly Asp Lys Ile Ala Cys Tyr Lys Leu Asn Thr
                115                 120                 125

Asp Asp Ser Pro Asn Ile Ala Thr Gln Tyr Gly Ile Arg Ser Ile Pro
130                 135                 140

Thr Val Leu Phe Phe Asn Asn Gly Glu Lys Lys Glu Ser Ile Ile Gly
145                 150                 155                 160

Ala Val Pro Lys Ser Thr Leu Ser Ala Thr Ile Glu Lys Tyr Ile Asp
                165                 170                 175

Leu

<210> SEQ ID NO 48
<211> LENGTH: 175
<212> TYPE: PRT
<213> ORGANISM: Medicago truncatula
<220> FEATURE:
<221> NAME/KEY: MISC_FEATURE
<222> LOCATION: (1)..(175)
<223> OTHER INFORMATION: Thioredoxin

<400> SEQUENCE: 48

Met Ala Leu Glu Asn Cys Leu Arg Val Ser Thr Ala Arg Pro Gln Cys
  1               5                  10                  15

Leu Pro Ser Leu Phe Pro Thr Ser Arg Glu Lys Val Val Phe Ser Ala
                 20                  25                  30

Gln Arg Ala Gly Phe Lys Lys Ser Leu Leu Asn Ser Thr Leu Ser Phe
             35                  40                  45

Pro Ser Gly Val Ala Tyr Arg Lys Ser Arg Phe Ile Cys Asn Ala Arg
 50                  55                  60

Glu Ala Val Asn Glu Val Gly Ala Val Thr Asp Ser Ser Trp Asn Glu
 65                  70                  75                  80

Leu Val Leu Ala Ser Asp Thr Pro Val Leu Val Asp Phe Trp Ala Pro
                 85                  90                  95

Trp Cys Gly Pro Cys Arg Met Ile Ala Pro Ile Ile Asp Glu Leu Ala
                100                 105                 110

Lys Glu Tyr Ala Gly Lys Ile Ser Cys Tyr Lys Leu Asn Thr Asp Glu
                115                 120                 125

Asn Pro Asn Ile Ala Thr Lys Tyr Gly Ile Arg Ser Ile Pro Thr Val
130                 135                 140

Leu Phe Phe Lys Asn Gly Glu Lys Lys Glu Ser Val Ile Gly Ala Val
145                 150                 155                 160

Pro Lys Ser Thr Leu Ser Thr Thr Val Glu Lys Tyr Ile Asp Ala
                165                 170                 175

<210> SEQ ID NO 49
<211> LENGTH: 180
<212> TYPE: PRT
<213> ORGANISM: Arachis hypogaea
<220> FEATURE:
<221> NAME/KEY: MISC_FEATURE
<222> LOCATION: (1)..(180)
<223> OTHER INFORMATION: Thioredoxin

<400> SEQUENCE: 49

Met Ala Leu Glu Asn Cys Leu Arg Leu Ser Thr Thr Val Gly Thr Ala
1               5                   10                  15

Arg Ile Gln Cys Leu Ser Pro Leu Ser Ser Trp Lys Lys Leu Val Phe
            20                  25                  30

Ser Ser Tyr Arg Gly Phe Asn Lys Ser Met Leu Tyr Ser Thr Val Ser
        35                  40                  45

Asn Ser Asn Pro Ser Leu Tyr Ser Thr Ala Gly Thr Ser Arg Lys Ser
    50                  55                  60

Ser Phe Val Cys Asn Ala Arg Glu Lys Val Asn Glu Val Gln Val Val
65                  70                  75                  80

Thr Asp Ser Ser Trp Asn Lys Leu Val Ile Gly Ser Glu Thr Pro Val
                85                  90                  95

Leu Val Glu Phe Trp Ala Pro Trp Cys Gly Pro Cys Arg Met Ile Ala
            100                 105                 110

Pro Ile Ile Asp Glu Leu Ala Lys Glu Tyr Ala Gly Lys Ile Ala Cys
        115                 120                 125

Tyr Lys Ile Asn Thr Asp Asp Cys Pro Asn Ile Ala Thr Gln Tyr Gly
    130                 135                 140

Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Ala Thr Leu
                165                 170                 175

Asp Lys Tyr Val
            180

<210> SEQ ID NO 50
<211> LENGTH: 175
<212> TYPE: PRT
<213> ORGANISM: Medicago truncatula
<220> FEATURE:
<221> NAME/KEY: MISC_FEATURE
<222> LOCATION: (1)..(175)
<223> OTHER INFORMATION: Thioredoxin

<400> SEQUENCE: 50

Met Ala Leu Glu Asn Cys Leu Arg Val Ser Thr Ala Arg Pro Gln Cys
1               5                   10                  15

Leu Pro Ser Leu Phe Pro Thr Ser Arg Glu Lys Val Val Phe Ser Ala
            20                  25                  30

Gln Arg Ala Gly Phe Lys Lys Ser Val Leu Asn Ser Thr Leu Ser Phe
        35                  40                  45

Pro Ser Gly Val Ala Tyr Arg Lys Ser Arg Phe Ile Cys Asn Ala Arg
    50                  55                  60

Glu Ala Val Asn Glu Val Gly Ala Val Thr Asp Ser Ser Trp Asn Glu
65                  70                  75                  80

Leu Val Leu Ala Ser Asp Thr Pro Val Leu Val Asp Phe Trp Ala Pro
                85                  90                  95

Trp Cys Gly Pro Cys Arg Met Ile Ala Pro Ile Ile Asp Glu Leu Ala
            100                 105                 110

Lys Glu Tyr Ala Gly Lys Ile Ser Cys Tyr Lys Leu Asn Thr Asp Glu
        115                 120                 125

Asn Pro Asn Ile Ala Thr Lys Tyr Gly Ile Arg Ser Ile Pro Thr Val
    130                 135                 140

```
Leu Phe Phe Lys Asn Gly Glu Lys Lys Glu Ser Val Ile Gly Ala Val
145                 150                 155                 160

Pro Lys Ser Thr Leu Ser Thr Thr Ala Glu Lys Tyr Ile Asp Ala
            165                 170                 175
```

<210> SEQ ID NO 51
<211> LENGTH: 183
<212> TYPE: PRT
<213> ORGANISM: Musa acuminata
<220> FEATURE:
<221> NAME/KEY: MISC_FEATURE
<222> LOCATION: (1)..(183)
<223> OTHER INFORMATION: Thioredoxin

<400> SEQUENCE: 51

```
Met Ala Leu Lys Ala Cys Phe Gln Val Ser Thr Ile Ala Ser Ser Ala
1               5                   10                  15

Ala Ala Thr Thr Gly Thr Trp Ala Leu Pro Ala His Arg Pro Val Phe
                20                  25                  30

Ile Arg Asp Lys Phe His Leu Pro Ala Thr Gly His Arg Lys Ser
            35                  40                  45

Val Ser Ser Pro Pro Ser Thr Ser Thr Gly Asp Gly Arg Arg Ser
50                  55                      60

Arg Val Thr Cys Arg Ala Lys Lys Thr Val Asp Glu Val Leu Val Val
65                  70                  75                  80

Val Asp Ala Asn Trp Glu Asn Leu Val Ala Ala Ser Asp Lys Pro Val
                85                  90                  95

Leu Val Glu Phe Trp Ala Pro Trp Cys Gly Pro Cys Arg Met Ile Ala
            100                 105                 110

Pro Val Ile Lys Glu Leu Ala Arg Asp Tyr Ala Gly Lys Ile Val Cys
            115                 120                 125

Cys Gln Val Asn Thr Asp Asp Cys Ser Gly Ile Ala Ser Arg Phe Gly
130                 135                     140

Ile Arg Ser Ile Pro Thr Val Leu Val Phe Lys Asn Gly Glu Lys Lys
145                 150                 155                 160

Glu Ser Val Ile Gly Ala Val Pro Lys Ser Thr Leu Val Ser Val Val
                165                 170                 175

Asp Lys Tyr Leu Glu Gly Ser
            180
```

<210> SEQ ID NO 52
<211> LENGTH: 185
<212> TYPE: PRT
<213> ORGANISM: Theobroma cacao
<220> FEATURE:
<221> NAME/KEY: MISC_FEATURE
<222> LOCATION: (1)..(185)
<223> OTHER INFORMATION: Thioredoxin

<400> SEQUENCE: 52

```
Met Ala Leu Glu Asn Cys Phe Gln Leu Ser Ser Ala Cys Thr Thr Arg
1               5                   10                  15

Ala Ser Val Leu Gln Ser Tyr His His Phe Ser Val Glu Lys Val
                20                  25                  30

His Leu Pro Thr Phe Arg Gly Phe Asn Lys Pro Asn Leu Ser Phe Thr
            35                  40                  45

Ser Ser Ser Ser Ser Ser Ser Leu Ala His Ser Phe Thr Arg Arg Ser
50                  55                      60
```

```
Gln Lys Ser Arg Leu Ile Cys Lys Ala Arg Glu Ala Val Asp Glu Val
 65                  70                  75                  80

Ala Val Val Thr Glu Ser Ser Trp Gly Glu Leu Val Val Gly Ser Glu
                 85                  90                  95

Thr Pro Val Leu Val Glu Phe Trp Ala Pro Trp Cys Gly Pro Cys Arg
            100                 105                 110

Met Ile Glu Pro Val Ile Ala Glu Leu Ala Lys Glu Tyr Ala Gly Lys
        115                 120                 125

Ile Ala Cys Tyr Lys Leu Asn Thr Asp Ser Pro Asn Ile Ala Thr
    130                 135                 140

Glu Phe Gly Ile Arg Ser Ile Pro Thr Met Leu Phe Phe Lys Asp Gly
145                 150                 155                 160

Glu Lys Lys Glu Ser Ile Ile Gly Ala Val Pro Lys Ser Thr Leu Ala
                165                 170                 175

Ala Thr Ile Asp Lys Tyr Val Asp Ser
            180                 185
```

```
<210> SEQ ID NO 53
<211> LENGTH: 181
<212> TYPE: PRT
<213> ORGANISM: Morus notabilis
<220> FEATURE:
<221> NAME/KEY: MISC_FEATURE
<222> LOCATION: (1)..(181)
<223> OTHER INFORMATION: Thioredoxin

<400> SEQUENCE: 53
```

```
Met Ala Leu Gly Asn Cys Leu Gln Leu Ser Thr Thr Cys Thr Arg Val
  1               5                  10                  15

Gly Ala Val Gln Cys His His Thr Phe Ser Ser Lys Glu Lys Leu Asn
                 20                  25                  30

Phe Pro Thr Phe Asn Lys Gly Leu Lys Lys Ser Ala Leu Ser Phe Ser
            35                  40                  45

Ser Ser Ser Ser Pro Phe Gly Tyr Phe Asn Ser Thr Thr Arg Lys Ser
        50                  55                  60

Leu Phe Val Cys Lys Ala Arg Glu Ala Leu Asp Glu Val Gln Val Val
 65                  70                  75                  80

Thr Asp Ser Ser Trp Asn Ser Leu Val Ile Ala Ser Glu Asn Pro Val
                 85                  90                  95

Leu Val Glu Phe Trp Ala Pro Trp Cys Gly Pro Cys Arg Met Ile Ala
            100                 105                 110

Pro Val Ile Asn Glu Leu Ala Lys Glu Tyr Ser Gly Lys Leu Asp Cys
        115                 120                 125

Tyr Lys Leu Asn Thr Asp Asp Cys Pro Asn Ile Ala Thr Gln Tyr Gly
    130                 135                 140

Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Thr Thr Ile
                165                 170                 175

Glu Lys Tyr Val Glu
            180
```

```
<210> SEQ ID NO 54
<211> LENGTH: 182
<212> TYPE: PRT
<213> ORGANISM: Fragaria vesca
<220> FEATURE:
<221> NAME/KEY: MISC_FEATURE
```

<222> LOCATION: (1)..(182)
<223> OTHER INFORMATION: Thioredoxin

<400> SEQUENCE: 54

Met Ala Leu Glu Asn Cys Leu Gln Leu Ser Thr Val Cys Thr Thr Arg
1               5                   10                  15

Val Gly Ala Ala Gln Cys Tyr His Pro Phe Ser Ser Glu Lys Leu Val
            20                  25                  30

Val Pro Thr Cys Asn Gly Leu Arg Lys Ser Gly Leu Lys Phe Ser Ser
        35                  40                  45

Ser Ser Ser Phe Val Ala Arg Pro Lys Ser Thr Arg Leu Gln Lys Ser
    50                  55                  60

Gly Phe Val Cys Lys Ala Arg Glu Ala Val Asp Gln Val Gln Val Val
65                  70                  75                  80

Thr Asp Ser Ser Trp Asn Asn Leu Val Ile Ala Ser Glu Asn Pro Val
                85                  90                  95

Leu Val Glu Phe Trp Ala Pro Trp Cys Gly Pro Cys Arg Met Ile Ala
            100                 105                 110

Pro Val Ile Asp Glu Leu Ala Lys Glu Tyr Ala Gly Lys Ile Ser Cys
        115                 120                 125

Phe Lys Leu Asn Thr Asp Asp Ser Pro Asn Thr Ala Thr Gln Tyr Gly
    130                 135                 140

Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Ala Thr Ile
                165                 170                 175

Glu Lys Tyr Val Asp Leu
            180

<210> SEQ ID NO 55
<211> LENGTH: 182
<212> TYPE: PRT
<213> ORGANISM: Pyrus x bretschneideri
<220> FEATURE:
<221> NAME/KEY: MISC_FEATURE
<222> LOCATION: (1)..(182)
<223> OTHER INFORMATION: Thioredoxin

<400> SEQUENCE: 55

Met Ala Leu Glu Asn Cys Leu Gln Leu Ser Thr Val Cys Thr Thr Arg
1               5                   10                  15

Val Gly Ala Ala Ala Gln Cys His His Pro Phe Ser Ser Met Gly Lys
            20                  25                  30

Phe Val Val Pro Ile Cys Asn Gly Leu Lys Lys Ser Ala Leu Lys Phe
        35                  40                  45

Ser Ser Ser Ser Ser Ser Phe Pro His Ser Ser Lys Ser Gln Lys Ser
    50                  55                  60

Arg Phe Ile Cys Lys Ala Arg Glu Ala Leu Asn Glu Val Gln Val Val
65                  70                  75                  80

Asn Asp Ser Ser Trp Ser Ser Leu Val Ile Ala Ser Glu Asn Pro Val
                85                  90                  95

Leu Val Glu Phe Trp Ala Pro Trp Cys Gly Pro Cys Arg Met Ile Ala
            100                 105                 110

Pro Val Ile Asp Glu Leu Ala Lys Glu Tyr Ala Gly Lys Ile Ser Cys
        115                 120                 125

Phe Lys Leu Asn Thr Asp Glu Ser Pro Asn Thr Ala Thr Gln Tyr Gly
    130                 135                 140

```
Ile Arg Ser Ile Pro Thr Val Leu Phe Phe Lys Asn Gly Glu Lys Lys
145                 150                 155                 160

Glu Ser Val Ile Gly Ala Val Pro Lys Ser Thr Leu Ser Ala Thr Ile
                165                 170                 175

Glu Lys Tyr Val Asp Leu
            180

<210> SEQ ID NO 56
<211> LENGTH: 187
<212> TYPE: PRT
<213> ORGANISM: Manihot esculenta
<220> FEATURE:
<221> NAME/KEY: MISC_FEATURE
<222> LOCATION: (1)..(187)
<223> OTHER INFORMATION: Thioredoxin

<400> SEQUENCE: 56

Met Ala Met Lys Asn Cys Phe Gln Val Ser Thr Val Cys Thr Gly Ala
1               5                   10                  15

Arg Ala Gly Val Leu Phe Ala Pro Val Glu Lys Leu His Leu Pro Thr
                20                  25                  30

Ser Cys Arg Gly Phe Asn Asn Gln Ser Asn Ser Ser Leu Ser Ser
            35                  40                  45

Thr Ser Ser Ser Ser Ser Phe Ala His Ser Leu Thr Thr Leu Arg Gly
50                  55                  60

Arg Ser Gln Lys Ser Arg Phe Val Cys Lys Ala Arg Glu Ala Leu Asp
65                  70                  75                  80

Glu Val Lys Ala Val Thr Asp Ser Ser Trp Asp Leu Val Ile Ala
                85                  90                  95

Ser Glu Thr Pro Val Leu Val Glu Phe Trp Ala Pro Trp Cys Gly Pro
                100                 105                 110

Cys Arg Met Ile Ala Pro Val Ile Asn Glu Leu Ala Lys Glu Tyr Ala
            115                 120                 125

Gly Lys Ile Ala Cys Phe Lys Val Asn Thr Asp Glu Cys Pro Asn Ile
        130                 135                 140

Ala Asn Lys Tyr Gly Ile Arg Ser Ile Pro Thr Val Leu Phe Phe Asn
145                 150                 155                 160

Lys Gly Glu Lys Lys Glu Ser Val Ile Gly Ala Val Pro Lys Thr Thr
                165                 170                 175

Leu Ser Ser Thr Leu Glu Lys Tyr Ile Asp Ala
            180                 185

<210> SEQ ID NO 57
<211> LENGTH: 191
<212> TYPE: PRT
<213> ORGANISM: Amborella trichopoda
<220> FEATURE:
<221> NAME/KEY: MISC_FEATURE
<222> LOCATION: (1)..(191)
<223> OTHER INFORMATION: Thioredoxin

<400> SEQUENCE: 57

Met Ala Ser Lys Thr Cys Ile Gln Leu Asn Asn Ile Thr Ser Arg Ala
1               5                   10                  15

Ser Ile Leu Arg Pro Pro Ile Pro Ile Pro Phe Pro Phe Pro Phe
                20                  25                  30

Pro Phe Pro Thr Lys Glu Lys Leu Asn Leu Pro Thr Cys Lys Gly Leu
            35                  40                  45
```

```
Lys Leu Thr Thr Ala Ser Leu Ser Ser Ser Leu Ser Ser Thr His Arg
 50                  55                  60

Leu Arg Leu Arg Gly Arg Arg Lys Phe Pro Val Cys Glu Ala Gln
 65                  70                  75                  80

Asn Thr Val Asp Lys Val Met Val Ile Thr Asp Ser Asn Trp Asn Asn
                 85                  90                  95

Leu Val Val Gly Ser Asp Thr Pro Val Ile Val Glu Phe Trp Ala Pro
                100                 105                 110

Trp Cys Gly Pro Cys Arg Met Ile Ala Pro Val Ile Asp Glu Leu Ala
                115                 120                 125

Lys Glu Tyr Ala Gly Lys Ile Met Cys Tyr Lys Leu Asn Thr Asp Glu
130                 135                 140

Cys Pro Thr Ile Ala Ser Gln Tyr Gly Ile Arg Ser Ile Pro Thr Val
145                 150                 155                 160

Leu Leu Phe Lys Asn Gly Glu Lys Glu Ser Ile Ile Gly Ala Val
                165                 170                 175

Pro Lys Ser Thr Leu Ser Ser Thr Ile Asp Lys Tyr Leu Glu Lys
                180                 185                 190
```

<210> SEQ ID NO 58
<211> LENGTH: 175
<212> TYPE: PRT
<213> ORGANISM: Phaseolus vulgaris
<220> FEATURE:
<221> NAME/KEY: MISC_FEATURE
<222> LOCATION: (1)..(175)
<223> OTHER INFORMATION: Thioredoxin

<400> SEQUENCE: 58

```
Met Ala Leu Glu Lys Cys Leu Thr Val Gly Thr Ala Thr Pro Gln Cys
 1               5                  10                  15

Leu Ser Pro Cys Phe Pro Thr Ser Arg Glu Lys Leu Val Phe Pro Thr
                 20                  25                  30

His Arg Gly Phe Lys Lys Ser Met Pro Asn Ala Lys Leu Ser Tyr Gln
                 35                  40                  45

Ser Leu Tyr Ser Thr Tyr Arg Lys Ser Arg Phe Val Cys Asn Ala Arg
 50                  55                  60

Glu Ala Val Asn Glu Val Lys Glu Val Thr Asp Ala Asn Trp Asn Gln
 65                  70                  75                  80

Leu Val Ile Ala Asn Glu Thr Pro Val Leu Val Glu Phe Trp Ala Pro
                 85                  90                  95

Trp Cys Gly Pro Cys Arg Met Ile Ala Pro Val Ile Glu Glu Leu Ala
                100                 105                 110

Lys Glu Tyr Gly Glu Lys Leu Ala Cys Tyr Lys Leu Asn Thr Asp Asp
                115                 120                 125

Ser Pro Asn Thr Ala Thr Gln Tyr Gly Ile Arg Ser Ile Pro Thr Val
                130                 135                 140

Leu Phe Phe Lys Asn Gly Glu Lys Glu Ser Ile Ile Gly Ala Val
145                 150                 155                 160

Pro Lys Ser Thr Leu Ser Ala Thr Val Glu Lys Tyr Ile Asp Leu
                165                 170                 175
```

<210> SEQ ID NO 59
<211> LENGTH: 183
<212> TYPE: PRT
<213> ORGANISM: Manihot esculenta
<220> FEATURE:
<221> NAME/KEY: MISC_FEATURE

```
<222> LOCATION: (1)..(183)
<223> OTHER INFORMATION: Thioredoxin

<400> SEQUENCE: 59

Met Ala Met Lys Asn Cys Phe Gln Val Ser Thr Thr Val Cys Thr Ser
1               5                   10                  15

Gly Arg Ala Gly Val Val Phe Ala Pro Val Glu Lys Leu His Leu Pro
            20                  25                  30

Thr Ser Cys Lys Gly Phe Asn Leu Ser Asn Leu Ser Ser Ser Ser Ser
        35                  40                  45

Ser Ser Leu Phe Ala His Ser Leu Thr Leu Arg Gly Asn Thr Gln Lys
50                  55                  60

Ser Arg Ile Ile Cys Lys Ala Arg Glu Ala Leu Asp Glu Val Gln Ala
65                  70                  75                  80

Val Thr Asp Ser Ser Trp Asp Asn Leu Val Ile Ala Ser Glu Thr Pro
                85                  90                  95

Ala Leu Val Glu Phe Trp Ala Pro Trp Cys Gly Pro Cys Arg Met Ile
            100                 105                 110

Ala Pro Val Ile Asp Glu Leu Ala Lys Glu Tyr Ala Gly Lys Ile Ala
        115                 120                 125

Cys Phe Lys Val Asn Thr Asp Glu Cys Pro Asn Ile Ala Asn Lys Tyr
130                 135                 140

Gly Ile Arg Ser Ile Pro Thr Val Leu Phe Phe Asn Lys Gly Glu Lys
145                 150                 155                 160

Lys Glu Ser Val Ile Gly Ala Val Pro Lys Thr Thr Leu Ser Ser Thr
                165                 170                 175

Leu Glu Lys Tyr Ile Asp Ala
            180

<210> SEQ ID NO 60
<211> LENGTH: 187
<212> TYPE: PRT
<213> ORGANISM: Ziziphus jujuba
<220> FEATURE:
<221> NAME/KEY: MISC_FEATURE
<222> LOCATION: (1)..(187)
<223> OTHER INFORMATION: Thioredoxin

<400> SEQUENCE: 60

Met Ala Met Glu Thr Cys Leu Gln Val Ser Arg Ala Cys Asn Thr Arg
1               5                   10                  15

Val Gly Ala Ile Gln Ser His His Thr Phe Ser Ser Lys Glu Gln Lys
            20                  25                  30

Leu Ile Lys Leu Pro Thr Phe Lys Gly Leu Lys Lys Ser Thr Ile Thr
        35                  40                  45

Leu Ser Ser Ser Pro Pro Pro Thr Ser Phe Pro Leu Ser Asn Ser Thr
50                  55                  60

Gly Gly Arg Lys Ser Leu Phe Val Cys Lys Ala Arg Glu Ala Val Asn
65                  70                  75                  80

Glu Val Gln Val Val Thr Asp Ser Gly Trp Lys Asn Leu Val Leu Gly
                85                  90                  95

Ser Glu Asn Pro Val Leu Val Glu Phe Trp Ala Pro Trp Cys Gly Pro
            100                 105                 110

Cys Arg Met Ile Ala Pro Ile Val Asp Glu Leu Ala Lys Glu Tyr Gly
        115                 120                 125

Gly Lys Ile Ser Cys Tyr Lys Leu Asn Thr Asp Asp Cys Pro Asn Ile
130                 135                 140
```

```
Ala Ser Gln Tyr Gly Ile Arg Ser Ile Pro Thr Val Leu Phe Phe Lys
145                 150                 155                 160

Asn Gly Glu Lys Lys Glu Ser Val Ile Gly Ala Val Pro Lys Ser Thr
                165                 170                 175

Leu Ser Ala Ala Ile Asp Lys Tyr Leu Asp Ser
            180                 185

<210> SEQ ID NO 61
<211> LENGTH: 186
<212> TYPE: PRT
<213> ORGANISM: Nelumbo nucifera
<220> FEATURE:
<221> NAME/KEY: MISC_FEATURE
<222> LOCATION: (1)..(186)
<223> OTHER INFORMATION: Thioredoxin

<400> SEQUENCE: 61

Met Ala Leu Glu Thr Cys Phe Gln Val Ser Thr Ile Ser Ala Thr Thr
1               5                   10                  15

Arg Ala Ser Val Leu Tyr Pro His Ser Ser Val Ser Ser Lys Glu Lys
                20                  25                  30

Leu Asn Leu Pro Thr Cys Lys Gly Leu Lys Val Ser Thr Leu Ser His
            35                  40                  45

Ala Ala Ser Ser Phe Ser Ser Leu Ser Arg Ser Val Asp His Arg
        50                  55                  60

Tyr Arg Gly Tyr Arg Ile Val Cys Lys Ala Gly Glu Val Ile Asn Glu
65                  70                  75                  80

Val Arg Val Val Asn Glu Ser Asp Trp Glu Gln Leu Val Ile Ala Ser
                85                  90                  95

Glu Thr Pro Val Leu Val Glu Phe Trp Ala Pro Trp Cys Gly Pro Cys
            100                 105                 110

Arg Met Ile Gln Pro Val Ile Asp Asp Leu Ala Lys Lys Tyr Ala Gly
        115                 120                 125

Lys Ile Val Cys Tyr Lys Val Asn Thr Asp Asp Cys Pro Asn Ile Ala
130                 135                 140

Thr Thr Tyr Gly Ile Arg Ser Ile Pro Thr Val Leu Val Phe Asn Asn
145                 150                 155                 160

Gly Glu Lys Lys Glu Ser Val Ile Gly Ala Val Pro Phe Ser Thr Leu
                165                 170                 175

Ser Ala Ala Val Glu Lys Tyr Leu Asn Ser
            180                 185

<210> SEQ ID NO 62
<211> LENGTH: 182
<212> TYPE: PRT
<213> ORGANISM: Citrus sinensis
<220> FEATURE:
<221> NAME/KEY: MISC_FEATURE
<222> LOCATION: (1)..(182)
<223> OTHER INFORMATION: Thioredoxin

<400> SEQUENCE: 62

Met Ala Met Lys Asn Cys Phe Gln Val Ser Ser Val Tyr Ser Thr Arg
1               5                   10                  15

Ala Gly Val Val Gln Cys Tyr Gln Pro Phe Ser Ser Val Lys Lys Ile
                20                  25                  30

His Leu Pro Ile Ser Asn Gly Leu Asn Lys Ser Asn Phe Ser Phe Thr
            35                  40                  45
```

```
Ser Ser Cys Ser Ser Leu Ser Leu Pro Leu Gly Ser Arg Ser Arg Asn
        50                  55                  60

Ser Leu Ile Leu Cys Lys Ala Arg Glu Ala Val Asn Glu Val Gln Val
65                  70                  75                  80

Val Thr Asp Ser Ser Trp Glu Asn Leu Val Ile Ser Ser Glu Asn Pro
                85                  90                  95

Val Leu Val Glu Phe Trp Ala Pro Trp Cys Gly Pro Cys Arg Met Ile
            100                 105                 110

Ala Pro Ala Ile Glu Glu Leu Ala Lys Glu Tyr Ala Gly Lys Val Ala
            115                 120                 125

Cys Phe Lys Leu Asn Thr Asp Asp Ser Pro Asn Ile Ala Thr Lys Tyr
130                 135                 140

Gly Ile Arg Ser Ile Pro Thr Val Leu Phe Phe Lys Asn Gly Glu Lys
145                 150                 155                 160

Lys Glu Ser Ile Ile Gly Ala Val Pro Lys Ser Thr Leu Ser Ser Thr
                165                 170                 175

Leu Asp Lys Tyr Val Glu
            180
```

```
<210> SEQ ID NO 63
<211> LENGTH: 178
<212> TYPE: PRT
<213> ORGANISM: Jatropha curcas
<220> FEATURE:
<221> NAME/KEY: MISC_FEATURE
<222> LOCATION: (1)..(178)
<223> OTHER INFORMATION: Thioredoxin

<400> SEQUENCE: 63
```

```
Met Ala Met Lys Asn Cys Phe Gln Val Cys Thr Ser Gly Arg Gly Gly
1               5                   10                  15

Val Val Gln Cys Ser Gln Pro Leu Lys Ile His Leu Pro Thr Ser Cys
            20                  25                  30

Lys Gly Ile Phe Asn Ile Ala Asn Lys Asp Leu Leu Ser Leu Ser Ser
            35                  40                  45

Ser Ser Leu Arg Leu Lys Pro Arg Ser Gln Lys Ala Arg Phe Val Cys
50                  55                  60

Lys Ala Arg Glu Ala Leu Asn Glu Val Gln Ala Val Thr Asp Ser Ser
65                  70                  75                  80

Trp Asp Asn Leu Val Ile Ser Ser Glu Asn Pro Ala Leu Val Glu Phe
                85                  90                  95

Trp Ala Pro Trp Cys Gly Pro Cys Arg Met Ile Ala Pro Val Ile Asp
            100                 105                 110

Glu Leu Ala Lys Glu Tyr Ala Gly Lys Ile Ser Cys Phe Lys Val Asn
            115                 120                 125

Thr Asp Glu Cys Pro Asn Ile Ala Asn Lys Tyr Gly Ile Arg Ser Ile
130                 135                 140

Pro Thr Val Leu Phe Phe Lys Lys Gly Glu Lys Lys Glu Ser Val Ile
145                 150                 155                 160

Gly Ala Val Pro Lys Thr Thr Leu Ser Ser Thr Ile Glu Lys Tyr Ile
                165                 170                 175

Asp Ala
```

```
<210> SEQ ID NO 64
<211> LENGTH: 188
<212> TYPE: PRT
<213> ORGANISM: Eucalyptus grandis
```

```
<220> FEATURE:
<221> NAME/KEY: MISC_FEATURE
<222> LOCATION: (1)..(188)
<223> OTHER INFORMATION: Thioredoxin

<400> SEQUENCE: 64

Met Glu Gln Cys Val Gln Met Met Ser Ala Thr Arg Gly Arg Val Leu
1               5                   10                  15

Gln Cys Cys Asp Arg Pro Val Ala Phe Ala Arg Arg Gly Met Pro Asn
            20                  25                  30

Ser Pro Thr Arg Lys Gly Gly Ala Val Leu Lys Lys Ser Ala Leu Asn
        35                  40                  45

Phe Ser Leu Ser Ser Pro Pro Leu Ala Ser Ser Leu Ser Val
50                  55                  60

Arg His Gln Arg Ser Ser Ile Ile Cys Lys Ala Arg Asp Ala Leu
65                  70                  75                  80

Asp Glu Val Arg Val Val Thr Asp Ser Ser Trp Ser Asn Leu Val Ile
                85                  90                  95

Ala Ser Glu Asn Pro Val Leu Val Glu Phe Trp Ala Pro Trp Cys Gly
            100                 105                 110

Pro Cys Arg Met Ile Ala Pro Val Ile Asp Glu Leu Ala Lys Glu Tyr
            115                 120                 125

Ala Gly Lys Ile Ala Cys Tyr Lys Leu Asn Thr Asp Asp Cys Pro Thr
130                 135                 140

Ile Ala Thr Gln Tyr Gly Ile Arg Ser Ile Pro Thr Val Leu Phe Phe
145                 150                 155                 160

Lys Asn Gly Glu Lys Lys Glu Ser Val Ile Gly Ala Val Pro Lys Ser
                165                 170                 175

Thr Leu Ser Ala Thr Val Glu Lys Tyr Leu Asp Leu
            180                 185

<210> SEQ ID NO 65
<211> LENGTH: 178
<212> TYPE: PRT
<213> ORGANISM: Wolffia australiana
<220> FEATURE:
<221> NAME/KEY: MISC_FEATURE
<222> LOCATION: (1)..(178)
<223> OTHER INFORMATION: Thioredoxin

<400> SEQUENCE: 65

Met Ala Leu Glu Ala Cys Phe Gln Val Ser Thr Met Ala His Ser Thr
1               5                   10                  15

Ile Ala Gly Lys Leu Ser Leu Pro Ala Cys Lys Thr Pro Lys Ile Ala
            20                  25                  30

Ala Phe Ser Phe Ser Ala Ser Ala Ser Arg Leu Ser Ala Asp Phe His
        35                  40                  45

Pro Arg Leu Arg Ala Pro Ser Lys Asn Thr Arg Ala Ala Arg Val Val
50                  55                  60

Cys Glu Ala Lys Asn Val Val Ala Glu Val Leu Glu Ala Asn Thr Asn
65                  70                  75                  80

Asn Trp Asp Ser Leu Val Leu Lys Ser Lys Leu Val Val Leu Val Asp
                85                  90                  95

Phe Trp Ala Pro Trp Cys Gly Pro Cys Arg Met Ile Glu Pro Val Ile
            100                 105                 110

Glu Gln Ile Ala Lys Asp Tyr Ala Gly Gln Val Ile Cys Val Lys Val
            115                 120                 125
```

```
Asn Thr Asp Asp Ser Pro Asn Leu Ala Asn Gln Phe Gly Ile Arg Ser
        130                 135                 140

Ile Pro Thr Val Leu Ile Phe Lys Asp Gly Asp Lys Lys Glu Thr Ile
145                 150                 155                 160

Val Gly Ala Val Pro Ala Ser Thr Leu Thr Asn Ser Leu Thr Lys Tyr
                165                 170                 175

Leu Gly

<210> SEQ ID NO 66
<211> LENGTH: 180
<212> TYPE: PRT
<213> ORGANISM: Populus euphratica
<220> FEATURE:
<221> NAME/KEY: MISC_FEATURE
<222> LOCATION: (1)..(180)
<223> OTHER INFORMATION: Thioredoxin

<400> SEQUENCE: 66

Met Ala Met Lys Asn Cys Phe Gln Val Cys Ser Val Ser Thr Thr Thr
1               5                   10                  15

Arg Ala Gly Val Cys His Pro Phe Ala Ser Val Glu Lys Leu Gln Leu
                20                  25                  30

Pro Ala Cys Lys Gly Leu Asn Thr Ser Asn Leu Pro Leu Ser Ser Pro
            35                  40                  45

Ser Ser Ser Phe Pro Arg Ser Leu Arg Ser Arg Cys Gln Lys Ser Arg
        50                  55                  60

Val Val Cys Lys Ala Arg Glu Ala Val Asp Ala Val Gln Val Ala Thr
65                  70                  75                  80

Asp Ala Ser Trp Asp Thr Val Ile Gly Ser Asp Thr Pro Val Leu Val
                85                  90                  95

Glu Phe Trp Ala Pro Trp Cys Gly Pro Cys Lys Met Ile Ala Pro Val
                100                 105                 110

Val Glu Glu Leu Ala Lys Glu Tyr Ala Gly Lys Ile Ala Cys Tyr Lys
            115                 120                 125

Val Asn Thr Asp Asp Cys Pro Asn Ile Ala Thr Lys Tyr Gly Ile Arg
        130                 135                 140

Ser Ile Pro Thr Val Leu Phe Phe Lys Lys Gly Glu Lys Lys Glu Ser
145                 150                 155                 160

Val Ile Gly Ala Val Pro Lys Thr Thr Leu Ser Asn Ser Ile Asp Lys
                165                 170                 175

Tyr Ile Asp Ala
            180

<210> SEQ ID NO 67
<211> LENGTH: 180
<212> TYPE: PRT
<213> ORGANISM: Populus trichocarpa
<220> FEATURE:
<221> NAME/KEY: MISC_FEATURE
<222> LOCATION: (1)..(180)
<223> OTHER INFORMATION: Thioredoxin

<400> SEQUENCE: 67

Met Ala Met Lys Asn Cys Phe Gln Val Ser Val Ser Thr Thr Thr
1               5                   10                  15

Arg Ala Gly Val Cys His Pro Phe Ala Pro Val Glu Lys Leu Gln Leu
                20                  25                  30

Pro Thr Cys Lys Gly Pro Asn Thr Ser Asn Leu Ser Leu Ser Ser Pro
            35                  40                  45
```

```
Ser Ser Ser Phe Pro Arg Ser Leu Arg Ser Arg Cys Gln Lys Ser Arg
    50                  55                  60

Val Val Cys Lys Ala Arg Glu Ala Val Asp Ala Val Gln Val Ala Thr
65                  70                  75                  80

Asp Ala Ser Trp Asp Thr Val Ile Gly Ser Asp Thr Pro Val Leu Val
                85                  90                  95

Glu Phe Trp Ala Pro Trp Cys Gly Pro Cys Lys Met Ile Ala Pro Val
                100                 105                 110

Val Glu Glu Leu Ala Lys Glu Tyr Ala Gly Lys Ile Ala Cys Tyr Lys
            115                 120                 125

Val Asn Thr Asp Asp Cys Pro Asn Ile Ala Thr Lys Tyr Gly Ile Arg
130                 135                 140

Ser Ile Pro Thr Val Leu Phe Phe Lys Lys Gly Glu Lys Lys Glu Ser
145                 150                 155                 160

Val Ile Gly Ala Val Pro Lys Thr Thr Leu Ser Asn Ser Ile Asp Lys
                165                 170                 175

Tyr Ile Asp Ala
            180

<210> SEQ ID NO 68
<211> LENGTH: 172
<212> TYPE: PRT
<213> ORGANISM: Pisum sativum
<220> FEATURE:
<221> NAME/KEY: MISC_FEATURE
<222> LOCATION: (1)..(172)
<223> OTHER INFORMATION: Thioredoxin

<400> SEQUENCE: 68

Met Ala Leu Glu Ser Leu Phe Lys Ser Ile His Thr Lys Thr Ser Leu
1               5                   10                  15

Ser Ser Ser Ile Val Phe Ile Phe Lys Gly Lys Ala Cys Leu Leu Thr
                20                  25                  30

Ser Lys Ser Arg Ile Gln Glu Ser Phe Ala Glu Leu Asn Ser Phe Thr
            35                  40                  45

Ser Leu Val Leu Leu Ile Glu Asn His Val Leu Leu His Ala Arg Glu
    50                  55                  60

Ala Val Asn Glu Val Gln Val Val Asn Asp Ser Ser Trp Asp Glu Leu
65                  70                  75                  80

Val Ile Gly Ser Glu Thr Pro Val Leu Val Asp Phe Trp Ala Pro Trp
                85                  90                  95

Cys Gly Pro Cys Arg Met Ile Ala Pro Ile Ile Asp Glu Leu Ala Lys
                100                 105                 110

Glu Tyr Ala Gly Lys Ile Lys Cys Tyr Lys Leu Asn Thr Asp Glu Ser
            115                 120                 125

Pro Asn Thr Ala Thr Lys Tyr Gly Ile Arg Ser Ile Pro Thr Val Leu
130                 135                 140

Phe Phe Lys Asn Gly Glu Arg Lys Asp Ser Val Ile Gly Ala Val Pro
145                 150                 155                 160

Lys Ala Thr Leu Ser Glu Lys Val Glu Lys Tyr Ile
                165                 170

<210> SEQ ID NO 69
<211> LENGTH: 187
<212> TYPE: PRT
<213> ORGANISM: Tamarix hispida
<220> FEATURE:
```

```
<221> NAME/KEY: MISC_FEATURE
<222> LOCATION: (1)..(187)
<223> OTHER INFORMATION: Thioredoxin

<400> SEQUENCE: 69

Met Ala Met Glu Asn Cys Phe Tyr Leu Ser Pro Ala Thr Ser Thr Ala
1               5                   10                  15

Arg Ala Ala Phe Ile Thr Lys Ser Met Ile Ala Pro Ser Lys Gly Arg
            20                  25                  30

Cys His Ser Pro Ser Ile Tyr Gln Gly Leu Thr Lys Pro Thr Ser Leu
        35                  40                  45

Phe Ser Ser Ser Ser Ser Ala Phe Pro Ser Ala Leu Ala Phe Glu
    50                  55                  60

Lys Thr Arg Arg Ser Ser Phe Val Cys Lys Ala Ser Gly Ala Ile Asp
65                  70                  75                  80

Glu Val Gln Ala Val Thr Asp Ser Ser Trp Glu Asn Leu Val Ile Gly
                85                  90                  95

Ser Glu Thr Pro Val Leu Val Glu Phe Trp Ala Pro Trp Cys Gly Pro
            100                 105                 110

Cys Arg Met Ile Ala Pro Val Val Asn Glu Leu Ala Lys Glu Trp Ala
        115                 120                 125

Gly Lys Ile Ala Cys Tyr Lys Val Asn Thr Asp Asp Cys Pro Asn Ile
    130                 135                 140

Ala Thr Lys Tyr Gly Ile Arg Ser Ile Pro Thr Val Leu Phe Phe Lys
145                 150                 155                 160

Asn Gly Glu Arg Lys Glu Ser Ala Ile Gly Ala Val Pro Lys Ser Thr
                165                 170                 175

Leu Ala Asp Ser Ile Glu Lys Tyr Leu Ala Val
            180                 185

<210> SEQ ID NO 70
<211> LENGTH: 172
<212> TYPE: PRT
<213> ORGANISM: Pisum sativum
<220> FEATURE:
<221> NAME/KEY: MISC_FEATURE
<222> LOCATION: (1)..(172)
<223> OTHER INFORMATION: Thioredoxin

<400> SEQUENCE: 70

Met Ala Leu Glu Ser Leu Phe Lys Ser Ile His Thr Lys Thr Ser Leu
1               5                   10                  15

Ser Ser Ser Ile Val Phe Ile Phe Lys Gly Lys Ala Cys Phe Leu Thr
            20                  25                  30

Ser Lys Ser Arg Ile Gln Glu Ser Phe Ala Glu Leu Asn Ser Phe Thr
        35                  40                  45

Ser Leu Val Leu Leu Ile Glu Asn His Val Leu Leu His Ala Arg Glu
    50                  55                  60

Ala Val Asn Glu Val Gln Val Val Asn Asp Ser Ser Trp Asp Glu Leu
65                  70                  75                  80

Val Ile Gly Ser Glu Thr Pro Val Leu Val Asp Phe Trp Ala Pro Trp
                85                  90                  95

Cys Gly Pro Cys Arg Met Ile Ala Pro Ile Ile Asp Glu Leu Ala Lys
            100                 105                 110

Glu Tyr Ala Gly Lys Ile Lys Cys Tyr Lys Leu Asn Thr Asp Glu Ser
        115                 120                 125

Pro Asn Thr Ala Thr Lys Tyr Gly Ile Arg Ser Ile Pro Thr Val Leu
```

```
                130               135                140
Phe Phe Lys Asn Gly Glu Arg Lys Asp Ser Val Ile Gly Ala Val Pro
145                 150                 155                 160

Lys Ala Thr Leu Ser Glu Lys Val Glu Lys Tyr Ile
                165                 170

<210> SEQ ID NO 71
<211> LENGTH: 183
<212> TYPE: PRT
<213> ORGANISM: Ricinus communis
<220> FEATURE:
<221> NAME/KEY: MISC_FEATURE
<222> LOCATION: (1)..(183)
<223> OTHER INFORMATION: Thioredoxin

<400> SEQUENCE: 71

Met Ala Met Lys Asn Cys Phe Gln Val Ser Thr Val Ser Ser Ala Arg
1               5                   10                  15

Ala Gly Val Val Gln Cys Phe His Val Asp Lys Ile Tyr Leu Pro Thr
            20                  25                  30

Tyr Cys Lys Gly Leu Asn Ile Ser Asn Leu Ser Leu Ser Ser Ser Ala
        35                  40                  45

Ser Ser Ser Pro Phe Phe Pro His Leu Arg Ser Arg Ser Gln Asn
    50                  55                  60

Ser Arg Ile Val Cys Lys Ala Arg Glu Ala Leu Asp Glu Val Gln Ala
65                  70                  75                  80

Val Thr Asp Ser Gly Trp Glu Ser Leu Val Ile Ala Ser Glu Asn Pro
                85                  90                  95

Val Leu Val Glu Phe Trp Ala Pro Trp Cys Gly Pro Cys Arg Met Ile
            100                 105                 110

Ala Pro Val Ile Asn Glu Leu Ala Lys Glu Tyr Ala Gly Lys Ile Ala
        115                 120                 125

Cys Phe Lys Val Asn Thr Asp Glu Cys Pro Asn Ile Ala Asn Lys Tyr
    130                 135                 140

Gly Ile Arg Ser Ile Pro Thr Val Leu Phe Phe Asn Lys Gly Glu Lys
145                 150                 155                 160

Lys Glu Ser Val Ile Gly Ala Val Pro Lys Thr Thr Leu Ser Ser Thr
                165                 170                 175

Ile Glu Lys Tyr Val Asp Ala
            180

<210> SEQ ID NO 72
<211> LENGTH: 177
<212> TYPE: PRT
<213> ORGANISM: Gossypium hirsutum
<220> FEATURE:
<221> NAME/KEY: MISC_FEATURE
<222> LOCATION: (1)..(177)
<223> OTHER INFORMATION: Thioredoxin

<400> SEQUENCE: 72

Met Ala Leu Lys Asn Cys Phe Gln Leu Thr Ser Val Cys Asn Thr Arg
1               5                   10                  15

Ala Ser Val Leu Gln Ser Tyr His His Gln Val Ser Val Asp
            20                  25                  30

Lys Ile His Phe Gln Thr Phe Lys Gly Leu Lys Leu Asn Lys Pro Asn
        35                  40                  45

Leu Ser Phe Thr Ala Gly Arg Cys Gln Lys Ser Arg Leu Ile Cys Lys
    50                  55                  60
```

```
Ala Ser Glu Ala Val Ala Gln Val Glu Val Val Thr Glu Ala Asp Trp
 65                  70                  75                  80

Glu Glu Leu Val Val Gly Ser Lys Thr Pro Val Leu Val Asp Phe Trp
                 85                  90                  95

Ala Pro Trp Cys Gly Pro Cys Arg Val Ile Glu Pro Val Ile Ala Glu
            100                 105                 110

Leu Ala Lys Glu Tyr Ala Gly Lys Ile Val Cys Tyr Lys Leu Asn Thr
        115                 120                 125

Asp Asp Ser Pro Asn Ile Ala Thr Lys Phe Gly Ile Arg Ser Ile Pro
    130                 135                 140

Thr Val Leu Phe Phe Lys Asn Gly Glu Lys Lys Glu Ser Ile Ile Gly
145                 150                 155                 160

Ala Val Pro Lys Ser Thr Leu Ala Ala Thr Ile Asp Lys Tyr Val Asp
                165                 170                 175

Gly

<210> SEQ ID NO 73
<211> LENGTH: 178
<212> TYPE: PRT
<213> ORGANISM: Arachis ipaensis
<220> FEATURE:
<221> NAME/KEY: MISC_FEATURE
<222> LOCATION: (1)..(178)
<223> OTHER INFORMATION: Thioredoxin

<400> SEQUENCE: 73

Met Ala Thr Ala Leu Glu Phe Leu Ala Val Leu Pro Arg Pro Ser Ser
 1               5                  10                  15

Ser Ala Thr Ala Phe Ser Pro Ala Thr Ala Arg Arg Ala Ser Ala Met
                 20                  25                  30

Phe Pro His Tyr Ser Gly Ile Lys Pro Arg Pro Ile Ala Ala Val Arg
            35                  40                  45

Cys Ala Gly Pro Leu Lys Pro Arg Thr Leu Thr Arg Ser Gly Arg Val
        50                  55                  60

Val Cys Glu Ala Gln Asp Thr Ala Val Glu Val Ala Ser Ile Thr Asp
 65                  70                  75                  80

Ala Asn Trp Gln Ser Leu Val Leu Glu Ser Glu Ser Pro Val Leu Val
                 85                  90                  95

Glu Phe Trp Ala Pro Trp Cys Gly Pro Cys Arg Met Ile His Pro Ile
            100                 105                 110

Ile Asp Glu Leu Ala Lys Glu Phe Ala Gly Lys Leu Lys Cys Tyr Lys
        115                 120                 125

Leu Asn Thr Asp Glu Ser Pro Ser Thr Ala Thr Arg Tyr Gly Ile Arg
    130                 135                 140

Ser Ile Pro Thr Val Met Ile Phe Lys Asn Gly Glu Lys Lys Asp Thr
145                 150                 155                 160

Val Ile Gly Ala Val Pro Lys Ser Thr Leu Thr Thr Ser Ile Glu Lys
                165                 170                 175

Phe Leu

<210> SEQ ID NO 74
<211> LENGTH: 181
<212> TYPE: PRT
<213> ORGANISM: Gossypium hirsutum
<220> FEATURE:
<221> NAME/KEY: MISC_FEATURE
<222> LOCATION: (1)..(181)
```

<223> OTHER INFORMATION: Thioredoxin

<400> SEQUENCE: 74

Met Ala Leu Glu Asn Cys Phe Gln Leu Ser Val Cys Thr Thr Arg
1               5                   10                  15

Ala Cys Val Met Gln Ser Tyr Arg His Gln Phe Ser Val Glu Lys
                20                  25                  30

Ile His Leu Pro Thr Phe Arg Gly Phe Asn Lys Pro Asn Leu Ser Phe
                35                  40                  45

Ser Ser Ser Phe Ala His Ser Phe Asn Gly Arg Cys Gln Lys Ser Arg
            50                  55                  60

Leu Ile Cys Lys Ala Ser Glu Ala Val Asp Gln Val Glu Ala Val Thr
65                  70                  75                  80

Glu Ala Ser Trp Gly Glu Leu Val Leu Gly Ser Glu Thr Pro Val Leu
                85                  90                  95

Val Glu Phe Trp Ala Pro Trp Cys Gly Pro Cys Arg Met Ile Glu Pro
                100                 105                 110

Val Ile Ala Asp Leu Ala Lys Glu Tyr Ala Gly Lys Ile Ala Cys Tyr
                115                 120                 125

Lys Leu Asn Thr Asp Glu Ser Pro Asn Ile Ala Thr Glu Phe Gly Ile
130                 135                 140

Arg Ser Ile Pro Thr Met Leu Phe Phe Lys Asn Gly Glu Lys Lys Glu
145                 150                 155                 160

Ser Ile Ile Gly Ala Val Pro Lys Ser Thr Leu Ala Ala Ser Ile Asp
                165                 170                 175

Lys Tyr Val Asp Ser
                180

<210> SEQ ID NO 75
<211> LENGTH: 182
<212> TYPE: PRT
<213> ORGANISM: Populus trichocarpa
<220> FEATURE:
<221> NAME/KEY: MISC_FEATURE
<222> LOCATION: (1)..(182)
<223> OTHER INFORMATION: Thioredoxin

<400> SEQUENCE: 75

Met Ala Leu His Ala Ser Met Asn Met Ser Thr Met Ser Thr Thr Arg
1               5                   10                  15

Ala Gly Val Leu Cys Ser Asn His Val Ala Cys Ser Lys Glu Lys Leu
                20                  25                  30

Lys Leu Pro Thr Gly Arg Gly Leu Arg Arg Ser Ser Ser Leu Ser Phe
                35                  40                  45

Pro Ser Ser Phe Ser Ser Tyr Ala Ser Val Lys Asn His Lys Ser
            50                  55                  60

Thr Ile Val Cys Lys Ala Gln Glu Ala Val Gly Val Val Gln Val Val
65                  70                  75                  80

Thr Asp Ser Ser Trp Asp Ser Leu Val Ile Gly Cys Glu Ile Pro Val
                85                  90                  95

Leu Val Glu Phe Trp Ala Pro Trp Cys Gly Pro Cys Arg Met Ile Thr
                100                 105                 110

Pro Val Ile Asp Glu Leu Ala Ala Glu Tyr Ala Gly Lys Ile Ala Cys
                115                 120                 125

Phe Lys Val Asn Thr Asp Asp Cys Pro Asn Ile Ala Ser Gln Tyr Ala
130                 135                 140

```
Ile Arg Ser Ile Pro Thr Val Leu Met Phe Lys Asn Gly Glu Lys Lys
145                 150                 155                 160

Glu Gly Val Ile Gly Ala Val Pro Lys Ala Thr Leu Ala Ala Ala Ile
                165                 170                 175

Glu Lys Tyr Val Glu Ala
            180

<210> SEQ ID NO 76
<211> LENGTH: 181
<212> TYPE: PRT
<213> ORGANISM: Gossypium raimondii
<220> FEATURE:
<221> NAME/KEY: MISC_FEATURE
<222> LOCATION: (1)..(181)
<223> OTHER INFORMATION: Thioredoxin

<400> SEQUENCE: 76

Met Ala Leu Glu Asn Cys Phe Gln Leu Ser Val Cys Thr Thr Arg
1               5                   10                  15

Thr Cys Val Met Gln Ser Tyr Arg His Gln Ile Ser Ser Val Glu Lys
                20                  25                  30

Ile His Leu Pro Thr Phe Arg Gly Phe Asn Lys Pro Asn Leu Ser Phe
                35                  40                  45

Ser Ser Ser Phe Val His Ser Phe Lys Gly Arg Cys Gln Lys Ser Arg
50                  55                  60

Leu Ile Cys Lys Ala Ser Glu Ala Val Asp Gln Val Glu Ala Val Thr
65                  70                  75                  80

Glu Ala Ser Trp Gly Glu Leu Val Leu Gly Ser Glu Thr Pro Val Leu
                85                  90                  95

Val Glu Phe Trp Ala Pro Trp Cys Gly Pro Cys Arg Met Ile Glu Pro
                100                 105                 110

Val Ile Ala Asp Leu Ala Lys Glu Tyr Ala Gly Lys Ile Ala Cys Tyr
            115                 120                 125

Lys Leu Asn Thr Asp Glu Ser Pro Asn Ile Ala Thr Glu Phe Gly Ile
        130                 135                 140

Arg Ser Ile Pro Thr Met Leu Phe Phe Lys Asn Gly Glu Lys Lys Glu
145                 150                 155                 160

Ser Ile Ile Gly Ala Val Pro Lys Ser Thr Leu Ala Ala Ser Ile Asp
                165                 170                 175

Lys Tyr Val Asp Ser
            180

<210> SEQ ID NO 77
<211> LENGTH: 178
<212> TYPE: PRT
<213> ORGANISM: Arachis duranensis
<220> FEATURE:
<221> NAME/KEY: MISC_FEATURE
<222> LOCATION: (1)..(178)
<223> OTHER INFORMATION: Thioredoxin

<400> SEQUENCE: 77

Met Ala Thr Ala Leu Glu Phe Leu Ala Val Leu Pro Arg Pro Ser Ser
1               5                   10                  15

Ser Ala Thr Ala Phe Ser Pro Ala Thr Ala Arg Arg Ala Ser Ala Met
                20                  25                  30

Phe Pro His Tyr Ser Gly Ile Lys Pro Arg Pro Ile Ala Ala Val Arg
                35                  40                  45

Cys Ala Gly Pro Leu Asn Pro Arg Thr Leu Thr Arg Ser Gly Arg Val
```

Val Cys Glu Ala Gln Asp Thr Ala Val Glu Val Ala Ser Ile Thr Asp
65                  70                  75                  80

Ala Asn Trp Gln Ser Leu Val Leu Glu Ser Glu Ser Pro Val Leu Ile
                85                  90                  95

Glu Phe Trp Ala Pro Trp Cys Gly Pro Cys Arg Met Ile His Pro Ile
            100                 105                 110

Ile Asp Glu Leu Ala Lys Glu Phe Ala Gly Arg Leu Arg Cys Tyr Lys
                115                 120                 125

Leu Asn Thr Asp Glu Ser Pro Ser Thr Ala Thr Arg Tyr Gly Ile Arg
            130                 135                 140

Ser Ile Pro Thr Val Met Ile Phe Lys Asn Gly Glu Lys Lys Asp Thr
145                 150                 155                 160

Val Ile Gly Ala Val Pro Lys Ser Thr Leu Thr Thr Ser Ile Glu Lys
                165                 170                 175

Phe Leu

<210> SEQ ID NO 78
<211> LENGTH: 191
<212> TYPE: PRT
<213> ORGANISM: Jatropha curcas
<220> FEATURE:
<221> NAME/KEY: MISC_FEATURE
<222> LOCATION: (1)..(191)
<223> OTHER INFORMATION: Thioredoxin

<400> SEQUENCE: 78

Met Ala Thr Val Leu Glu Ser Leu Thr Ile Pro Arg Ser Ser Ala Leu
1               5                   10                  15

Pro Lys Pro Thr Ile Ser Pro Ser Val Thr Ala Ser Ser Ile Ser Tyr
                20                  25                  30

Ile Asn Arg Arg Pro Ala Val Ser Leu Pro Glu Ala Arg Gly Leu Lys
            35                  40                  45

Val Ser Phe Asn Ser Ser Met Thr Arg Ser Phe Gly Trp Ala Ser Gln
50                  55                  60

Thr Leu Asp Arg Ser Arg Leu Ala Arg Gly Ala Arg Ile Val Cys Glu
65                  70                  75                  80

Ala Gln Asn Thr Ala Val Glu Val Leu Glu Val Thr Glu Lys Thr Trp
                85                  90                  95

Gln Ser Leu Val Leu Glu Ser Glu Ser Pro Val Leu Val Glu Phe Trp
            100                 105                 110

Ala Pro Trp Cys Gly Pro Cys Arg Met Ile His Pro Val Ile Asp Ala
        115                 120                 125

Leu Ala Gly Glu Tyr Val Gly Lys Leu Lys Cys Tyr Lys Leu Asn Thr
    130                 135                 140

Asp Glu Ser Pro Ala Ile Ala Thr Arg Tyr Gly Ile Arg Ser Ile Pro
145                 150                 155                 160

Thr Val Met Ile Phe Lys Asn Gly Lys Lys Asp Ala Ile Ile Gly
                165                 170                 175

Ala Val Pro Lys Ser Thr Leu Thr Thr Ser Ile Glu Lys Phe Leu
            180                 185                 190

<210> SEQ ID NO 79
<211> LENGTH: 182
<212> TYPE: PRT
<213> ORGANISM: Populus euphratica
<220> FEATURE:

```
<221> NAME/KEY: MISC_FEATURE
<222> LOCATION: (1)..(182)
<223> OTHER INFORMATION: Thioredoxin

<400> SEQUENCE: 79
```

| | | | | | | | | | | | | | | |
|---|---|---|---|---|---|---|---|---|---|---|---|---|---|---|
|Met|Ala|Leu|His|Ala|Ser|Met|Asn|Met|Ser|Thr|Met|Ser|Thr|Thr|Arg|
|1| | | |5| | | |10| | | |15| | |

| | | | | | | | | | | | | | |
|---|---|---|---|---|---|---|---|---|---|---|---|---|---|
|Ala|Gly|Val|Leu|Cys|Ser|Asn|His|Val|Ala|Cys|Ser|Lys|Glu|Lys|Leu|
| | | |20| | | |25| | | |30| | | |

Lys Leu Pro Thr Gly Gly Gly Leu Arg Arg Ser Ser Ser Leu Ser Phe
             35              40              45

Pro Ser Ser Phe Ser Ser Tyr Ala Ser Val Lys Asn Tyr Lys Ser
 50              55              60

Thr Ile Val Cys Lys Ala Gln Glu Ala Gly Val Val Gln Val Val
65              70              75              80

Thr Asp Ser Ser Trp Asp Ser Leu Val Ile Gly Cys Glu Ile Pro Val
             85              90              95

Leu Val Glu Phe Trp Ala Pro Trp Cys Gly Pro Cys Arg Met Ile Thr
             100             105             110

Pro Val Ile Asp Glu Leu Ala Ala Glu Tyr Ala Gly Lys Ile Ala Cys
             115             120             125

Tyr Lys Val Asn Thr Asp Asp Cys Pro Asn Ile Ala Ser Gln Tyr Ala
130              135             140

Ile Arg Ser Ile Pro Thr Val Leu Met Phe Lys Asn Gly Glu Lys Lys
145              150             155             160

Glu Gly Val Ile Gly Ala Val Pro Lys Ala Thr Leu Ala Ala Ala Ile
             165             170             175

Glu Lys Tyr Val Glu Val
             180

```
<210> SEQ ID NO 80
<211> LENGTH: 191
<212> TYPE: PRT
<213> ORGANISM: Picea sitchensis
<220> FEATURE:
<221> NAME/KEY: MISC_FEATURE
<222> LOCATION: (1)..(191)
<223> OTHER INFORMATION: Thioredoxin

<400> SEQUENCE: 80
```

Met Ala Met Ser Ser Ala Asn Cys Val Ser Ser His Arg Phe Thr Ala
1               5               10              15

Ala Val Ser Ser Ser Ser Cys Thr Tyr Ala Pro Pro Leu His Ser Lys
             20              25              30

Gln Ala Arg Gly Arg Ala Gly Leu Pro Ile Cys Asn Gly Phe Arg Leu
             35              40              45

Lys Ser Ser Thr Ser Phe Ser Gly His Glu Asn Ser Leu His Lys
 50              55              60

Thr Thr Arg Lys Ala His Pro Arg Arg Val Val Cys Glu Ala Gln Glu
65              70              75              80

Thr Ala Thr Glu Ala Leu Glu Val Asn Asp Ser Thr Trp Gln Lys Leu
             85              90              95

Val Leu Glu Ser Asn Ile Pro Val Leu Val Asp Phe Trp Ala Pro Trp
             100             105             110

Cys Gly Pro Cys Arg Met Ile Ala Pro Leu Ile Asp Glu Leu Ala Lys
             115             120             125

Gln Tyr Ala Gly Lys Ile Met Cys Leu Lys Leu Asn Thr Asp Glu Ser

```
                130                 135                 140
Pro Asn Ile Ala Thr Glu Tyr Gly Ile Arg Ser Ile Pro Thr Val Met
145                 150                 155                 160

Val Phe Lys Asn Gly Glu Lys Lys Asp Thr Val Ile Gly Ala Val Pro
                165                 170                 175

Lys Thr Thr Leu Ile Ala Thr Val Glu Lys Tyr Leu Asp Arg Arg
            180                 185                 190

<210> SEQ ID NO 81
<211> LENGTH: 185
<212> TYPE: PRT
<213> ORGANISM: Hevea brasiliensis
<220> FEATURE:
<221> NAME/KEY: MISC_FEATURE
<222> LOCATION: (1)..(185)
<223> OTHER INFORMATION: Thioredoxin

<400> SEQUENCE: 81

Met Ala Thr Val Leu Asp Phe Leu Ser Ile Pro Ser Phe Pro Ser Phe
1               5                   10                  15

Pro Lys Ser Thr Val Ser Pro Ser Leu Thr Ala Ser Ala Ser Pro Ile
                20                  25                  30

Ser Ser Ile Ser Gln Arg Pro Ala Val Arg Leu Pro Glu Ala Ser Gly
            35                  40                  45

Leu Lys Ile Arg Ser Phe Gly Ser Val Thr Gln Thr Pro Ile Arg Ser
    50                  55                  60

Arg Leu Ala Arg Gly Arg Ile Val Cys Glu Thr Gln Glu Thr Ala Val
65                  70                  75                  80

Gly Val Leu Ala Val Asn Glu Lys Thr Trp Lys Asn Leu Val Leu Gly
                85                  90                  95

Ser Glu Ser Pro Val Leu Val Glu Phe Trp Ala Pro Trp Cys Gly Pro
            100                 105                 110

Cys Arg Met Ile His Pro Val Ile Asp Glu Leu Ser Arg Glu Tyr Thr
    115                 120                 125

Gly Lys Leu Lys Cys Tyr Lys Leu Asn Thr Asp Asp Ser Pro Ala Ile
130                 135                 140

Ala Thr Gln Tyr Gly Ile Arg Ser Ile Pro Thr Val Met Ile Phe Lys
145                 150                 155                 160

Asn Gly Glu Lys Lys Asp Ala Ile Ile Gly Ala Val Pro Lys Ser Thr
                165                 170                 175

Leu Val Thr Ser Ile Asp Lys Phe Leu
            180                 185

<210> SEQ ID NO 82
<211> LENGTH: 181
<212> TYPE: PRT
<213> ORGANISM: Vigna angularis
<220> FEATURE:
<221> NAME/KEY: MISC_FEATURE
<222> LOCATION: (1)..(181)
<223> OTHER INFORMATION: Thioredoxin

<400> SEQUENCE: 82

Met Ala Thr Leu Gln Leu Gln Ser Leu Thr Leu Thr Arg Ser Ser Thr
1               5                   10                  15

Leu Pro Ser Leu Thr Ser Pro Ile Pro Val Thr Ala Arg Leu Asn
                20                  25                  30

Ser Ala Ala Leu Pro Arg Tyr Ser Gly Leu Arg Leu Arg Ala Thr Val
            35                  40                  45
```

```
Gly Thr Val Phe Ser Thr Arg Ala Ala Ser Arg Thr Ala Pro Arg Gly
    50                  55                  60

Gly Arg Ile Ala Cys Glu Ala Gln Asp Thr Ala Ile Glu Val Thr Ser
65                  70                  75                  80

Ile Thr Asp Ala Asn Trp Gln Ser Leu Val Leu Glu Ser Glu Thr Pro
                85                  90                  95

Val Leu Val Glu Phe Trp Ala Pro Trp Cys Gly Pro Cys Arg Met Ile
                100                 105                 110

His Pro Ile Ile Asp Glu Leu Ala Lys Glu Tyr Val Gly Lys Leu Lys
            115                 120                 125

Cys Tyr Lys Leu Asn Thr Asp Glu Ser Pro Ser Thr Ala Ser Arg Tyr
    130                 135                 140

Gly Ile Arg Ser Ile Pro Thr Val Ile Ile Phe Lys Asn Gly Glu Lys
145                 150                 155                 160

Lys Asp Thr Val Ile Gly Ala Val Pro Lys Thr Thr Leu Thr Ser Ser
                165                 170                 175

Ile Glu Lys Phe Leu
            180

<210> SEQ ID NO 83
<211> LENGTH: 177
<212> TYPE: PRT
<213> ORGANISM: Gossypium raimondii
<220> FEATURE:
<221> NAME/KEY: MISC_FEATURE
<222> LOCATION: (1)..(177)
<223> OTHER INFORMATION: Thioredoxin

<400> SEQUENCE: 83

Met Ala Leu Lys Asn Cys Phe Gln Leu Thr Ser Val Cys Asn Thr Arg
1               5                   10                  15

Ala Ser Val Leu Gln Ser Tyr His His His Val Ser Ser Val Asp
                20                  25                  30

Lys Ile His Phe Gln Thr Phe Lys Gly Leu Lys Leu Asn Lys Pro Asn
            35                  40                  45

Leu Ser Phe Thr Ala Asp Arg Cys Pro Lys Ser Arg Leu Ile Cys Lys
    50                  55                  60

Ala Ser Glu Ala Val Ala Gln Val Gly Val Val Thr Glu Ala Asp Trp
65                  70                  75                  80

Glu Glu Leu Val Val Gly Ser Lys Thr Pro Val Leu Val Asp Phe Trp
                85                  90                  95

Ala Pro Trp Cys Gly Pro Cys Arg Val Ile Glu Pro Val Ile Ala Glu
                100                 105                 110

Leu Ala Lys Glu Tyr Ala Gly Lys Ile Val Cys Tyr Lys Leu Asn Thr
            115                 120                 125

Asp Asp Ser Pro Asn Ile Ala Thr Lys Phe Gly Ile Arg Ser Ile Pro
    130                 135                 140

Thr Val Leu Phe Phe Lys Asn Gly Glu Lys Lys Glu Ser Ile Ile Gly
145                 150                 155                 160

Ala Val Pro Lys Ser Thr Leu Ala Ala Thr Ile Asp Lys Tyr Val Asp
                165                 170                 175

Gly

<210> SEQ ID NO 84
<211> LENGTH: 176
<212> TYPE: PRT
```

```
<213> ORGANISM: Cicer arietinum
<220> FEATURE:
<221> NAME/KEY: MISC_FEATURE
<222> LOCATION: (1)..(176)
<223> OTHER INFORMATION: Thioredoxin

<400> SEQUENCE: 84

Met Ala Thr Leu Leu Glu Ser Ile Ser Val Val Pro Arg Pro Ser Ala
1               5                   10                  15

Ala Ile Ser Pro Val Val Ala Arg Arg Ser Ser Leu Lys Phe Ala Thr
            20                  25                  30

Tyr Val Gly Leu Arg Pro Arg Pro Arg His Ile Phe Ser Thr
        35                  40                  45

His Cys Ala Thr Ser Arg Ile Ala Ser Arg Asn Ser Arg Val Leu Cys
    50                  55                  60

Glu Ala Gln Asp Thr Ala Val Asp Val Ala Ile Thr Asp Glu Asn
65                  70                  75                  80

Trp Gln Ser Leu Val Leu Glu Ser Gly Ser Pro Val Leu Val Glu Phe
                85                  90                  95

Trp Ala Ser Trp Cys Gly Pro Cys Arg Met Ile His Pro Ile Ile Asp
            100                 105                 110

Glu Leu Ala Lys Gln Tyr Ala Gly Lys Leu Lys Cys Tyr Lys Leu Asn
        115                 120                 125

Thr Asp Glu Ser Pro Ser Thr Ala Thr Arg Tyr Gly Ile Arg Ser Ile
130                 135                 140

Pro Thr Val Met Ile Phe Lys Asn Gly Glu Lys Lys Asp Thr Val Ile
145                 150                 155                 160

Gly Ala Val Pro Lys Ser Thr Leu Thr Ser Ser Ile Glu Lys Phe Leu
                165                 170                 175

<210> SEQ ID NO 85
<211> LENGTH: 179
<212> TYPE: PRT
<213> ORGANISM: Populus trichocarpa x Populus deltoides
<220> FEATURE:
<221> NAME/KEY: MISC_FEATURE
<222> LOCATION: (1)..(179)
<223> OTHER INFORMATION: Thioredoxin

<400> SEQUENCE: 85

Met Ala Met Lys Asn Cys Phe Gln Val Ser Ser Val Ser Thr Thr Arg
1               5                   10                  15

Ala Gly Val Cys His Pro Phe Ala Pro Val Glu Lys Leu Gln Leu Pro
            20                  25                  30

Thr Ser Lys Gly Leu Asn Pro Ser Asn Leu Leu Ser Ser Pro Ser
        35                  40                  45

Ser Ser Phe Pro Pro Ser Leu Arg Ser Arg Cys Gln Glu Ser Arg Ile
    50                  55                  60

Val Cys Lys Ala Arg Glu Ala Val Asp Ala Val Gln Val Ala Thr Asp
65                  70                  75                  80

Ala Ser Trp Asp Ala Val Ile Gly Gly Asp Thr Pro Val Leu Val Glu
                85                  90                  95

Phe Trp Ala Pro Trp Cys Gly Pro Cys Lys Met Ile Ala Pro Val Ile
            100                 105                 110

Glu Glu Leu Ala Gln Glu Tyr Ala Gly Lys Ile Ala Cys Tyr Lys Val
        115                 120                 125

Asn Thr Asp Asp Cys Pro Ser Ile Ala Thr Lys Tyr Gly Ile Arg Ser
130                 135                 140
```

```
Ile Pro Thr Val Leu Phe Phe Lys Lys Gly Glu Lys Glu Ser Val
145                 150                 155                 160

Ile Gly Ala Val Pro Lys Thr Thr Leu Ser Ser Ile Glu Lys Tyr
                165                 170                 175

Ile Asp Val

<210> SEQ ID NO 86
<211> LENGTH: 172
<212> TYPE: PRT
<213> ORGANISM: Cynara cardunculus
<220> FEATURE:
<221> NAME/KEY: MISC_FEATURE
<222> LOCATION: (1)..(172)
<223> OTHER INFORMATION: Thioredoxin

<400> SEQUENCE: 86

Met Ala Met Glu Lys Cys Phe Gly Met Gly Thr Thr Arg Ala Thr Val
1               5                   10                  15

Leu Gln His Thr His Arg His Phe Ala Ser Ile Asp Ala Pro Cys Phe
                20                  25                  30

Thr Lys Ala Pro Met Met Lys Ser Ser Thr Leu Thr Ser Ser Phe Phe
                35                  40                  45

Lys Leu Arg Cys Ser Asn Arg Ser Asn Arg Ile Val Cys Lys Ser Ala
50                  55                  60

Val Asn Gln Val Glu Val Thr Asp Cys Thr Trp Thr Glu Leu Val
65                  70                  75                  80

Val Ala Ala Asp Leu Pro Val Leu Val Glu Phe Trp Ala Pro Trp Cys
                85                  90                  95

Gly Pro Cys Arg Met Ile Ala Pro Val Val Asp Glu Leu Ala Lys Glu
                100                 105                 110

Tyr Ser Gly Lys Ala Val Cys Phe Lys Ile Asn Thr Asp Asp Cys Pro
            115                 120                 125

Asn Ile Ala Ser Gln Tyr Gly Ile Arg Ser Ile Pro Thr Leu Leu Phe
        130                 135                 140

Phe Lys Asn Gly Glu Lys Lys Glu Ser Val Val Gly Ala Val Pro Lys
145                 150                 155                 160

Ser Thr Leu Ile Ala Thr Leu Asp Lys Tyr Ile Asp
                165                 170

<210> SEQ ID NO 87
<211> LENGTH: 104
<212> TYPE: PRT
<213> ORGANISM: Vitis vinifera
<220> FEATURE:
<221> NAME/KEY: MISC_FEATURE
<222> LOCATION: (1)..(104)
<223> OTHER INFORMATION: Thioredoxin

<400> SEQUENCE: 87

Met Glu Pro Asp Ser Ser Trp Ser Asn Val Ile Ala Ser Glu Asn
1               5                   10                  15

Pro Val Leu Val Glu Phe Trp Ala Pro Trp Cys Gly Pro Cys Arg Met
                20                  25                  30

Ile Ala Pro Val Ile Asp Glu Leu Ala Lys Glu Tyr Ala Gly Lys Ile
                35                  40                  45

Val Cys Cys Lys Val Asn Thr Asp Asp Cys Pro Asn Ile Ala Thr Gln
50                  55                  60

Tyr Gly Ile Arg Ser Ile Pro Thr Val Leu Phe Phe Lys Asn Gly Glu
```

```
                65                  70                  75                  80
Arg Lys Glu Ser Val Ile Gly Ala Val Pro Lys Ser Thr Leu Thr Ala
                    85                  90                  95

Thr Ile Glu Lys Tyr Val Asp Met
                100

<210> SEQ ID NO 88
<211> LENGTH: 174
<212> TYPE: PRT
<213> ORGANISM: Vigna angularis
<220> FEATURE:
<221> NAME/KEY: MISC_FEATURE
<222> LOCATION: (1)..(174)
<223> OTHER INFORMATION: Thioredoxin

<400> SEQUENCE: 88

Met Ala Thr Leu Phe Asp Ser Leu Ala Phe Val Gly Ile Pro Ser Ala
1               5                   10                  15

Val Ser Phe Pro Phe Ala Ala Arg Pro Thr Ser Ala Lys Leu Pro Gln
            20                  25                  30

Cys Ile Gly Leu Arg Leu Arg Pro Thr Val Ala Arg Phe Val Ala Ala
        35                  40                  45

Ser Ala Pro Lys Val Ala Ser His Ala Ala Arg Val Val Cys Glu Ala
    50                  55                  60

Gln Asp Ala Val Val Asp Val Ala Ile Thr Asp Ala Asn Trp Gln
65                  70                  75                  80

Ser Leu Val Leu Glu Ser Asp Ser Ala Val Leu Val Glu Phe Trp Ala
                85                  90                  95

Pro Trp Cys Gly Pro Cys Arg Met Ile His Pro Ile Ile Asp Glu Leu
            100                 105                 110

Ala Lys Gln Tyr Thr Gly Lys Leu Lys Cys Tyr Lys Leu Asn Thr Asp
        115                 120                 125

Glu Ser Pro Ser Thr Ala Thr Arg Tyr Gly Ile Arg Ser Ile Pro Thr
    130                 135                 140

Val Met Ile Phe Lys Asn Gly Glu Lys Lys Asp Thr Val Ile Gly Ala
145                 150                 155                 160

Val Pro Lys Ser Thr Leu Thr Thr Ser Ile Glu Lys Phe Val
                165                 170

<210> SEQ ID NO 89
<211> LENGTH: 174
<212> TYPE: PRT
<213> ORGANISM: Gossypium hirsutum
<220> FEATURE:
<221> NAME/KEY: MISC_FEATURE
<222> LOCATION: (1)..(174)
<223> OTHER INFORMATION: Thioredoxin

<400> SEQUENCE: 89

Met Ala Ser Ser Thr Val Pro Ile Gly Val Ala Val Ser Ala Pro Ser
1               5                   10                  15

Ser Val Leu Ser Asn Arg Arg Ile Ser Val Arg Phe Ser Glu Phe Arg
            20                  25                  30

Gly Leu Lys Ile Lys Pro Arg Leu Ala Ser Leu Thr Gln Ser Thr Arg
        35                  40                  45

Ser Ala Ile Gln Asp Arg Arg Arg Val Gly Arg Val Val Cys Glu Ala
    50                  55                  60

Gln Asn Thr Ala Val Asp Val Pro Ala Ile Lys Asp Glu Thr Trp Gln
65                  70                  75                  80
```

```
Ser Leu Val Leu Glu Cys Glu Leu Pro Val Leu Val Glu Phe Trp Ala
                85                  90                  95

Pro Trp Cys Gly Pro Cys Arg Met Ile His Pro Ile Ile Asp Glu Leu
            100                 105                 110

Ser Lys Gln Tyr Ala Gly Lys Leu Lys Cys Tyr Lys Val Asn Thr Asp
        115                 120                 125

Glu Ser Pro Asn Ile Ala Thr Arg Tyr Gly Ile Arg Ser Ile Pro Thr
130                 135                 140

Val Met Ile Phe Lys Arg Gly Glu Lys Asp Ala Val Ile Gly Ala
145                 150                 155                 160

Val Pro Lys Ser Thr Leu Thr Thr Cys Ile Glu Arg Leu Leu
                165                 170
```

<210> SEQ ID NO 90
<211> LENGTH: 179
<212> TYPE: PRT
<213> ORGANISM: Populus euphratica
<220> FEATURE:
<221> NAME/KEY: MISC_FEATURE
<222> LOCATION: (1)..(179)
<223> OTHER INFORMATION: Thioredoxin

<400> SEQUENCE: 90

```
Met Ala Met Lys Asn Cys Phe Gln Val Ser Ser Val Ser Thr Thr Arg
1               5                   10                  15

Ala Gly Val Cys Arg Pro Phe Ala Pro Val Glu Lys Leu Gln Leu Pro
            20                  25                  30

Thr Ser Lys Gly Leu Asn Thr Ser Asn Leu Leu Leu Ser Ser Pro Ser
        35                  40                  45

Ser Ser Phe Pro Pro Ser Leu Arg Ser Arg Cys Gln Glu Ser Arg Ile
50                  55                  60

Val Cys Lys Ala Arg Glu Ala Val Asp Ala Val Gln Val Ala Thr Asp
65                  70                  75                  80

Ala Ser Trp Asp Ala Val Ile Gly Gly Asp Thr Pro Val Leu Val Glu
                85                  90                  95

Phe Trp Ala Pro Trp Cys Gly Pro Cys Lys Met Ile Ala Pro Val Ile
            100                 105                 110

Glu Glu Leu Ala Gln Glu Tyr Ala Gly Lys Ile Ala Cys Tyr Lys Val
        115                 120                 125

Asn Thr Asp Asp Cys Pro Ser Ile Ala Thr Lys Tyr Gly Ile Arg Ser
130                 135                 140

Ile Pro Thr Val Leu Phe Phe Lys Gly Glu Lys Lys Glu Ser Val
145                 150                 155                 160

Ile Gly Ala Val Pro Lys Thr Thr Leu Ser Ser Ser Ile Glu Lys Tyr
                165                 170                 175

Ile Asp Val
```

<210> SEQ ID NO 91
<211> LENGTH: 179
<212> TYPE: PRT
<213> ORGANISM: Populus trichocarpa
<220> FEATURE:
<221> NAME/KEY: MISC_FEATURE
<222> LOCATION: (1)..(179)
<223> OTHER INFORMATION: Thioredoxin

<400> SEQUENCE: 91

```
Met Ala Met Lys Asn Cys Phe Gln Val Ser Ser Val Ser Thr Thr Arg
```

```
                 1               5                  10                 15
Ala Gly Val Cys His Pro Phe Ala Pro Val Glu Lys Leu Gln Leu Pro
                20                  25                 30
Thr Ser Lys Gly Leu Asn Thr Ser Asn Leu Leu Ser Ser Pro Ser
                35                  40                 45
Ser Ser Phe Pro Pro Ser Leu Arg Ser Arg Cys Gln Glu Ser Arg Ile
        50                  55                 60
Val Cys Lys Ala Arg Glu Ala Val Asp Ala Val Gln Val Ala Thr Asp
65                  70                  75                 80
Ala Ser Trp Asp Ala Val Ile Gly Gly Asp Thr Pro Val Leu Val Glu
                85                  90                 95
Phe Trp Ala Pro Trp Cys Gly Pro Cys Lys Met Ile Ala Pro Val Ile
                100                 105                110
Glu Glu Leu Ala Gln Glu Tyr Ala Gly Lys Ile Ala Cys Tyr Lys Val
                115                 120                125
Asn Thr Asp Asp Cys Pro Ser Ile Ala Thr Lys Tyr Gly Ile Arg Ser
                130                 135                140
Ile Pro Thr Val Leu Phe Phe Lys Lys Gly Glu Lys Lys Glu Ser Val
145                 150                 155                160
Ile Gly Ala Val Pro Lys Thr Thr Leu Ser Ser Ile Glu Lys Tyr
                165                 170                175
Ile Asp Val
```

<210> SEQ ID NO 92
<211> LENGTH: 182
<212> TYPE: PRT
<213> ORGANISM: Solanum tuberosum
<220> FEATURE:
<221> NAME/KEY: MISC_FEATURE
<222> LOCATION: (1)..(182)
<223> OTHER INFORMATION: Thioredoxin

<400> SEQUENCE: 92

```
Met Ala Ala Val Leu Glu Thr Ile Thr Val Pro Arg Ala Ser Ala Leu
1               5                  10                 15
Pro Ser Ser Ser Leu Ala Pro Val Ala Gly Tyr Ser Phe Ser Gly Pro
                20                  25                 30
Arg Ser Ser Val Arg Phe Ser Gln Ser Ser Gly Leu Lys Ile Gln Pro
                35                  40                 45
Ile Arg Ser Ser Val Ser Thr Ser Ser Cys Ser Lys Ile Ile Pro Arg
        50                  55                 60
Gly Gly Arg Val Val Cys Glu Ala Gln Asn Ala Ala Val Glu Val Ala
65                  70                  75                 80
Ala Val Ser Asp Lys Thr Trp Lys Thr Leu Val Val Glu Ser Thr Val
                85                  90                 95
Pro Val Leu Val Glu Phe Trp Ala Pro Trp Cys Gly Pro Cys Arg Met
                100                 105                110
Ile His Pro Val Ile Asp Glu Leu Ala Lys Glu Tyr Val Gly Lys Leu
                115                 120                125
Thr Cys Leu Lys Leu Asn Thr Asp Glu Ser Pro Ser Ile Ala Thr Glu
                130                 135                140
Phe Gly Ile Arg Ser Ile Pro Thr Val Met Ile Phe Lys Asn Gly Glu
145                 150                 155                160
Lys Lys Asp Ala Ile Ile Gly Ala Val Pro Lys Ser Thr Leu Thr Thr
                165                 170                175
```

```
Ser Ile Glu Lys Phe Leu
            180

<210> SEQ ID NO 93
<211> LENGTH: 174
<212> TYPE: PRT
<213> ORGANISM: Gossypium arboreum
<220> FEATURE:
<221> NAME/KEY: MISC_FEATURE
<222> LOCATION: (1)..(174)
<223> OTHER INFORMATION: Thioredoxin

<400> SEQUENCE: 93

Met Ala Ser Ser Thr Val Pro Ile Gly Val Ala Val Ser Ala Pro Cys
1               5                   10                  15

Ser Phe Leu Ser Asn Arg Arg Thr Ser Val Arg Phe Ser Glu Phe Arg
            20                  25                  30

Gly Leu Lys Ile Lys Pro Arg Leu Ala Ser Leu Thr Gln Ser Thr Arg
        35                  40                  45

Ser Ala Ile Gln Asp Arg Arg Val Gly Arg Val Val Cys Glu Ala
    50                  55                  60

Gln Asn Thr Ala Val Asp Val Pro Ala Ile Lys Asp Glu Thr Trp Gln
65                  70                  75                  80

Ser Leu Val Leu Glu Cys Glu Leu Pro Val Leu Val Glu Phe Trp Ala
                85                  90                  95

Pro Trp Cys Gly Pro Cys Arg Met Ile His Pro Ile Ile Asp Glu Leu
            100                 105                 110

Ser Lys Gln Tyr Ala Gly Lys Leu Lys Cys Tyr Lys Val Asn Thr Asp
        115                 120                 125

Glu Ser Pro Asn Ile Ala Thr Arg Tyr Gly Ile Arg Ser Ile Pro Thr
    130                 135                 140

Val Met Ile Phe Lys Arg Gly Glu Lys Lys Asp Ala Val Ile Gly Ala
145                 150                 155                 160

Val Pro Lys Ser Thr Leu Thr Thr Cys Ile Glu Arg Leu Leu
                165                 170

<210> SEQ ID NO 94
<211> LENGTH: 94
<212> TYPE: PRT
<213> ORGANISM: Oryza brachyantha
<220> FEATURE:
<221> NAME/KEY: MISC_FEATURE
<222> LOCATION: (1)..(94)
<223> OTHER INFORMATION: Thioredoxin

<400> SEQUENCE: 94

Met Val Leu Gly Ser Glu Ala Pro Val Leu Val Glu Phe Trp Ala Pro
1               5                   10                  15

Trp Cys Gly Pro Cys Arg Met Ile Ala Pro Val Ile Asp Glu Leu Ala
            20                  25                  30

Lys Glu Tyr Val Gly Lys Ile Arg Cys Cys Lys Val Asn Thr Asp Asp
        35                  40                  45

Ser Pro Asn Ile Ala Thr Asn Tyr Gly Ile Arg Ser Ile Pro Thr Val
    50                  55                  60

Leu Met Phe Lys Asn Gly Glu Lys Lys Glu Ser Val Ile Gly Ala Val
65                  70                  75                  80

Pro Lys Thr Thr Leu Ala Thr Ile Ile Asp Lys Tyr Val Thr
                85                  90
```

-continued

```
<210> SEQ ID NO 95
<211> LENGTH: 181
<212> TYPE: PRT
<213> ORGANISM: Vigna radiata
<220> FEATURE:
<221> NAME/KEY: MISC_FEATURE
<222> LOCATION: (1)..(181)
<223> OTHER INFORMATION: Thioredoxin

<400> SEQUENCE: 95

Met Ala Thr Val Gln Leu Gln Ser Leu Thr Leu Thr Arg Ser Ser Thr
1               5                   10                  15

Leu Pro Ser Leu Thr Ser Pro Ile Pro Val Thr Ala Arg Arg Asn
            20                  25                  30

Ser Ala Ala Leu Pro Arg Tyr Ser Gly Leu Arg Leu Arg Ala Thr Val
        35                  40                  45

Gly Thr Val Phe Ser Thr Cys Ala Ala Ser Arg Thr Thr Pro Arg Gly
    50                  55                  60

Gly Arg Ile Ala Cys Glu Ala Gln Asp Thr Ala Val Glu Val Thr Ala
65                  70                  75                  80

Ile Thr Asp Ala Asn Trp Gln Ser Leu Val Leu Glu Ser Glu Thr Pro
                85                  90                  95

Val Leu Val Glu Phe Trp Ala Pro Trp Cys Gly Pro Cys Arg Met Ile
            100                 105                 110

His Pro Ile Ile Asp Glu Leu Ala Lys Glu Tyr Val Gly Lys Leu Lys
        115                 120                 125

Cys Tyr Lys Leu Asn Thr Asp Glu Ser Pro Ser Thr Ala Ser Arg Tyr
    130                 135                 140

Gly Ile Arg Ser Ile Pro Thr Val Ile Ile Phe Lys Asn Gly Glu Lys
145                 150                 155                 160

Lys Asp Thr Val Ile Gly Ala Val Pro Lys Thr Thr Leu Thr Ser Ser
                165                 170                 175

Ile Glu Lys Phe Leu
            180

<210> SEQ ID NO 96
<211> LENGTH: 173
<212> TYPE: PRT
<213> ORGANISM: Medicago truncatula
<220> FEATURE:
<221> NAME/KEY: MISC_FEATURE
<222> LOCATION: (1)..(173)
<223> OTHER INFORMATION: Thioredoxin

<400> SEQUENCE: 96

Met Ala Thr Val Gln Leu Glu Ser Phe Ser Leu Ile Arg Ser Pro Ile
1               5                   10                  15

Val Ala Ser Ser Arg Arg Ser Thr Ala Thr Phe Pro Pro Tyr Thr Gly
            20                  25                  30

Leu Lys Leu Arg Pro Val Ser Ala Thr Arg Leu Arg Ser Gln Ser Thr
        35                  40                  45

Gly Arg Val Phe Pro Arg Gly Gly Thr Val Val Cys Glu Ala Arg Asp
    50                  55                  60

Thr Thr Ala Val Glu Val Ala Ser Ile Thr Asp Gly Asn Trp Gln Ser
65                  70                  75                  80

Leu Val Ile Glu Ser Glu Thr Pro Val Leu Val Glu Phe Trp Ala Pro
                85                  90                  95

Trp Cys Gly Pro Cys Arg Met Ile His Pro Ile Ile Asp Glu Leu Ala
            100                 105                 110
```

```
Lys Glu Tyr Ala Gly Lys Leu Lys Cys Tyr Lys Leu Asn Thr Asp Glu
            115                 120                 125

Ser Pro Ser Val Ala Thr Arg Tyr Gly Ile Arg Ser Ile Pro Thr Val
        130                 135                 140

Ile Phe Phe Lys Asn Gly Glu Lys Lys Asp Thr Val Ile Gly Ala Val
145                 150                 155                 160

Pro Lys Ala Thr Leu Thr Thr Asn Ile Glu Lys Phe Leu
                165                 170

<210> SEQ ID NO 97
<211> LENGTH: 187
<212> TYPE: PRT
<213> ORGANISM: Eucalyptus grandis
<220> FEATURE:
<221> NAME/KEY: MISC_FEATURE
<222> LOCATION: (1)..(187)
<223> OTHER INFORMATION: Thioredoxin

<400> SEQUENCE: 97

Met Ala Ala Val Leu Glu Ser Leu Ala Val Pro Arg Ser Ser Gly Ala
1               5                   10                  15

Ala Ser Ala Ala Ala Leu Ser Pro Val Ala Ser Ala Ser Ser Leu Ala
            20                  25                  30

Pro Thr Ala Gly Arg Arg Ser Ala Thr Phe Pro Gln Ala Ser Gly
        35                  40                  45

Leu Arg Ile Gly Pro Val Ser Val Ala Arg Ser Leu Arg Ser Pro Ser
    50                  55                  60

Gln Arg Pro Arg Arg Ala Pro Ala Val Val Cys Glu Ala Gln Asp Thr
65                  70                  75                  80

Ala Val Glu Val Ala Gly Val Thr Asp Ala Thr Trp Gln Ser Leu Val
                85                  90                  95

Leu Glu Ser Glu Ser Pro Val Leu Val Glu Phe Trp Ala Pro Trp Cys
            100                 105                 110

Gly Pro Cys Arg Met Ile His Pro Val Ile Asp Glu Leu Ala Lys Gln
        115                 120                 125

Tyr Ala Gly Lys Leu Lys Cys Tyr Lys Val Asn Thr Asp Glu Ser Pro
    130                 135                 140

Ser Val Ala Thr Arg Tyr Gly Ile Arg Ser Ile Pro Thr Val Met Ile
145                 150                 155                 160

Phe Lys Ser Gly Glu Lys Lys Asp Ala Val Ile Gly Ala Val Pro Lys
                165                 170                 175

Ser Thr Leu Thr Thr Ser Ile Glu Lys Phe Leu
            180                 185

<210> SEQ ID NO 98
<211> LENGTH: 190
<212> TYPE: PRT
<213> ORGANISM: Populus euphratica
<220> FEATURE:
<221> NAME/KEY: MISC_FEATURE
<222> LOCATION: (1)..(190)
<223> OTHER INFORMATION: Thioredoxin

<400> SEQUENCE: 98

Met Ala Ala Leu Leu Glu Ser Leu Thr Val Pro Pro Leu Thr Phe Thr
1               5                   10                  15

Lys Pro Lys Pro Thr Thr Thr Thr Thr Leu Ser Ala Phe Ser Ser Ser
            20                  25                  30
```

Ile His Arg Arg Ser Leu Arg Leu Pro His Val Lys Gly Leu Lys Leu
            35                  40                  45

Ser Phe Asn Ser Ser Thr Ile Asn Arg Ser Ser Gly Ser Phe Val Thr
 50                  55                  60

Leu Thr Ser Ser Arg Leu Ser Arg Gly Gly Arg Ile Val Cys Glu Ala
 65                  70                  75                  80

Gln Glu Thr Ala Val Glu Val Ala Ser Val Thr Asp Ala Thr Trp Lys
                 85                  90                  95

Ser Val Val Leu Glu Ser Glu Ser Pro Val Leu Val Glu Phe Trp Ala
                100                 105                 110

Pro Trp Cys Gly Pro Cys Arg Met Ile His Pro Ile Ile Asp Glu Leu
            115                 120                 125

Ala Arg Gln Tyr Thr Gly Lys Leu Lys Cys Tyr Lys Val Asn Thr Asp
130                 135                 140

Asp Cys Pro Ser Ile Ala Thr Gln Tyr Gly Ile Arg Ser Ile Pro Thr
145                 150                 155                 160

Val Ile Ile Phe Lys Asn Gly Glu Lys Lys Glu Ala Ile Ile Gly Ala
                165                 170                 175

Val Pro Lys Thr Thr Leu Thr Thr Thr Ile Asp Lys Phe Leu
                180                 185                 190

<210> SEQ ID NO 99
<211> LENGTH: 174
<212> TYPE: PRT
<213> ORGANISM: Cajanus cajan
<220> FEATURE:
<221> NAME/KEY: MISC_FEATURE
<222> LOCATION: (1)..(174)
<223> OTHER INFORMATION: Thioredoxin

<400> SEQUENCE: 99

Met Ala Thr Leu Phe Asp Ser Leu Ala Val Ser Arg Leu Pro Ser Ala
 1               5                  10                  15

Ala Phe Ser Pro Val Ala Ala Arg Arg Thr Ser Val Lys Leu Pro His
                 20                  25                  30

Cys Ala Gly Leu Lys Leu Arg Pro Ala Ala Thr Arg Phe Val Ala Ser
            35                  40                  45

Pro Thr Pro Lys Thr Val Ser Arg Ala Ala Arg Val Ala Cys Glu Ala
 50                  55                  60

Gln Asp Thr Ala Val Asp Val Ala Pro Ile Thr Asp Ala Asn Trp Gln
 65                  70                  75                  80

Ser Leu Val Leu Glu Ser Glu Thr Ala Val Leu Val Glu Phe Trp Ala
                 85                  90                  95

Pro Trp Cys Gly Pro Cys Arg Met Ile His Pro Ile Ile Asp Glu Leu
            100                 105                 110

Ala Lys Gln Tyr Ala Gly Lys Leu Lys Cys Tyr Lys Leu Asn Thr Asp
            115                 120                 125

Glu Ser Pro Ser Thr Ala Thr Arg Tyr Gly Ile Arg Ser Ile Pro Thr
130                 135                 140

Val Met Ile Phe Lys Asn Gly Glu Lys Lys Asp Thr Val Ile Gly Ala
145                 150                 155                 160

Val Pro Lys Ser Thr Leu Thr Thr Ser Ile Glu Lys Phe Val
                165                 170

<210> SEQ ID NO 100
<211> LENGTH: 184
<212> TYPE: PRT

<213> ORGANISM: Arachis ipaensis
<220> FEATURE:
<221> NAME/KEY: MISC_FEATURE
<222> LOCATION: (1)..(184)
<223> OTHER INFORMATION: Thioredoxin

<400> SEQUENCE: 100

```
Met Ala Thr Val Gln Leu Gln Ser Leu Thr Leu Ser Arg Ser Ser Ala
1               5                   10                  15

Leu Ser Ala Pro Thr Thr Val Ser Ser Ile Ser Gly Arg Arg Glu Ser
            20                  25                  30

Ile Lys Leu Pro Arg His Ala Gly Leu Arg Leu Ala Thr Ser Thr Arg
        35                  40                  45

Phe Ser Gly Ser Pro Ser Arg Ala Val Ser Arg Ile Ala Ala Ser Arg
    50                  55                  60

Ala Gly Gly Arg Val Val Cys Glu Thr Gln Asp Thr Ala Ala Val Gln
65                  70                  75                  80

Val Asp Pro Ile Thr Asp Ala Asn Trp Gln Ser Leu Val Leu Glu Ser
                85                  90                  95

Asp Thr Pro Val Leu Val Glu Phe Trp Ala Pro Trp Cys Gly Pro Cys
            100                 105                 110

Arg Met Ile His Pro Ile Ile Asp Glu Leu Ala Lys Glu Tyr Ala Gly
        115                 120                 125

Lys Leu Lys Cys Tyr Lys Leu Asn Thr Asp Glu Ser Pro Ser Thr Ala
    130                 135                 140

Thr Arg Tyr Gly Ile Arg Ser Ile Pro Thr Val Ile Ile Phe Lys Asn
145                 150                 155                 160

Gly Glu Lys Lys Asp Ala Val Ile Gly Ala Val Pro Lys Thr Thr Leu
                165                 170                 175

Met Thr Ser Ile Glu Lys Phe Leu
            180
```

<210> SEQ ID NO 101
<211> LENGTH: 1086
<212> TYPE: DNA
<213> ORGANISM: Zea mays
<220> FEATURE:
<221> NAME/KEY: misc_feature
<222> LOCATION: (1)..(1086)
<223> OTHER INFORMATION: transcription factor

<400> SEQUENCE: 101

| | | | | |
|---|---|---|---|---|
| atgggctcca acgatccaaa cacaccgtcc aaggcctcca aggcgagcga gcaggatcag | | | | 60 |
| ccaccggcga caaccacctc cagcgggacc gccagcgtgt acccagagtg gccgtccttt | | | | 120 |
| caagcgtatt ccgccattcc accgcacgcc ttttccac cgaccgtcgc ggccaacccg | | | | 180 |
| caggcgcatc cgtacatgtg gggcgcccaa ccaatcgtcc cgccatatgg accccacca | | | | 240 |
| ccgccgccat atgtcatgta cccgccgggg accgtctatg cgcacccgtc cacaccacca | | | | 300 |
| gcgatgcacc catttgggca ctatccgatg ccgacaaatg ccatgccga acacacgggg | | | | 360 |
| gccgccccga gcgcgccaga aatgaacggc aaatccgagc caggccgcac aagcgcccca | | | | 420 |
| agcgcgaacg gcattaccag ccactccgaa tccggcagcg aaagcgaatc cgaaggctcc | | | | 480 |
| gatgacaatt cccaaaatga ttcccactcc aaggataacg acgggaagga agacgggaat | | | | 540 |
| tcccaaaacg ggatgagcta ttccggctcc caggggggtcg tgaatcagac catggcgatg | | | | 600 |
| ctccgatgc agccaggggc gatggtcggg ggggtgccga gctccacagc cgccaatctg | | | | 660 |
| aatatcgggg tggactactg ggccgcgccg gggtccgccg cggtcccggc ggcgcacggg | | | | 720 |

```
aaggccccag cggggagcgc gaggggcgac cagtgggatg agcgcgagct caaaaaacag      780
aaaaggaaac aatccaatcg cgaaagcgcg cgcaggtccc gcctcaggaa gcaggccgag      840
tgtgaggaac tggggcagcg cgccgaagcg ctgcgcagcg aaaactccag cctgcgcgcc      900
gagctcgagc gcatcaggaa agaatacgag cagctcctct cccagaatgc gtccctcaaa      960
gagaagctgg gggcggcgag ctccgacagc ctgccagaca tgaatgaaca aaatgatggc     1020
gacggcgatg ggggctacag gaaacaaccg gattccgacg ccaccaacc gggcagcgaa      1080 tcctga                                                                1086

<210> SEQ ID NO 102
<211> LENGTH: 361
<212> TYPE: PRT
<213> ORGANISM: Zea mays
<220> FEATURE:
<221> NAME/KEY: MISC_FEATURE
<222> LOCATION: (1)..(361)
<223> OTHER INFORMATION: transcription factor

<400> SEQUENCE: 102

Met Gly Ser Asn Asp Pro Asn Thr Pro Ser Lys Ala Ser Lys Ala Ser
1               5                   10                  15

Glu Gln Asp Gln Pro Pro Ala Thr Thr Thr Ser Ser Gly Thr Ala Ser
                20                  25                  30

Val Tyr Pro Glu Trp Pro Ser Phe Gln Ala Tyr Ser Ala Ile Pro Pro
            35                  40                  45

His Ala Phe Phe Pro Pro Thr Val Ala Ala Asn Pro Gln Ala His Pro
        50                  55                  60

Tyr Met Trp Gly Ala Gln Pro Ile Val Pro Pro Tyr Gly Thr Pro Pro
65                  70                  75                  80

Pro Pro Pro Tyr Val Met Tyr Pro Pro Gly Thr Val Tyr Ala His Pro
                85                  90                  95

Ser Thr Pro Pro Ala Met His Pro Phe Gly His Tyr Pro Met Pro Thr
            100                 105                 110

Asn Gly His Ala Glu Thr His Gly Ala Ala Pro Ser Ala Pro Glu Met
        115                 120                 125

Asn Gly Lys Ser Glu Pro Gly Arg Thr Ser Ala Pro Ser Ala Asn Gly
    130                 135                 140

Ile Thr Ser His Ser Glu Ser Gly Ser Glu Ser Glu Ser Glu Gly Ser
145                 150                 155                 160

Asp Asp Asn Ser Gln Asn Asp Ser His Ser Lys Asp Asn Asp Gly Lys
                165                 170                 175

Glu Asp Gly Asn Ser Gln Asn Gly Met Ser Tyr Ser Gly Ser Gln Gly
            180                 185                 190

Val Val Asn Gln Thr Met Ala Met Leu Pro Met Gln Pro Gly Ala Met
        195                 200                 205

Val Gly Gly Val Pro Ser Ser Thr Ala Ala Asn Leu Asn Ile Gly Val
    210                 215                 220

Asp Tyr Trp Ala Ala Pro Gly Ser Ala Ala Val Pro Ala Ala His Gly
225                 230                 235                 240

Lys Ala Pro Ala Gly Ser Ala Arg Gly Asp Gln Trp Asp Glu Arg Glu
                245                 250                 255

Leu Lys Lys Gln Lys Arg Lys Gln Ser Asn Arg Glu Ser Ala Arg Arg
            260                 265                 270

Ser Arg Leu Arg Lys Gln Ala Glu Cys Glu Glu Leu Gly Gln Arg Ala
```

```
                275                 280                 285
Glu Ala Leu Arg Ser Glu Asn Ser Ser Leu Arg Ala Glu Leu Glu Arg
    290                 295                 300

Ile Arg Lys Glu Tyr Glu Gln Leu Leu Ser Gln Asn Ala Ser Leu Lys
305                 310                 315                 320

Glu Lys Leu Gly Ala Ala Ser Ser Asp Ser Leu Pro Asp Met Asn Glu
                325                 330                 335

Gln Asn Asp Gly Asp Gly Asp Gly Tyr Arg Lys Gln Pro Asp Ser
                340                 345                 350

Asp Gly His Gln Pro Gly Ser Glu Ser
            355                 360

<210> SEQ ID NO 103
<211> LENGTH: 912
<212> TYPE: DNA
<213> ORGANISM: Zea mays
<220> FEATURE:
<221> NAME/KEY: promoter
<222> LOCATION: (1)..(912)
<223> OTHER INFORMATION: ZmRbcS promoter

<400> SEQUENCE: 103
gagctccctt taatctggcg ctagatctgc atccgcggct tgcaaagata aatggcacat      60
ttagtgtgtt attttgcaat acctttcata gtagatatcc ttaaatgcag ttttaggcat    120
gtttgggtaa ttaaataaca ttttaggag gagttttaga tttacctttc tttcgtgatg     180
actgatgaca gacgtgggga attcaaatgc aactctagcg aaagttcata tatttttcat    240
aaatagctga ggctggggta attatttttt ttgtagaaaa atagaatagg tggaatggtt    300
ggggaaggcg taggcgctcg tggacgacgc ccgataaaag acaagaggcg gaattgccat    360
gaattcgagg tagctaagta aggcgcatat atatgccaaa aaattctact gtcactttcc    420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga agccgaagcc aaaactgtt    600 ttgtctttgc ccagaaccgc gacgagccta aactgcgctt cctcctatct acaagtccct    660
ggcacatcac gcatagtcca accatggcgc gcaggcgata aggcgcgcca cggggacgcg    720
acatgtggtg gcgacgcga tcaggatagg gccaggctgg ccgggcgcgg ccacgggaga    780
acggtggcca ctcgtcccac atccgcttcg tcctgtcctg tactgcgtcc tgccccaac    840 gagagccgga gccggccatc ccgtcgcaca ctctcccct ctatatatgc cgtcggtgtg    900
ggggagccta ct                                                       912

<210> SEQ ID NO 104
<211> LENGTH: 1404
<212> TYPE: DNA
<213> ORGANISM: Synechococcus sp.
<220> FEATURE:
<221> NAME/KEY: misc_feature
<222> LOCATION: (1)..(1404)
<223> OTHER INFORMATION: ictB

<400> SEQUENCE: 104
atgacagtgt ggcagacact cacattcgct cattaccagc ctcagcagtg gggccattct      60
tctttcctcc ataggctctt cggctctctc agggcttgga gggcttcttc tcagctcctc    120
gtgtggtctg aggctctcgg cggcttcctc ctcgctgtgg tgtacggctc tgctcctttc    180
```

```
gtgccttctt ctgctctcgg cctcggcctc gctgctattg ctgcttactg ggctctcctc      240
tctctcacag atattgatct caggcaggct acacctattc attggctcgt gctcctctac      300
tggggcgtgg atgctctcgc tacaggcctc tctcctgtga gggctgctgc tctcgtgggc      360
ctcgctaagc tcacactcta cctcctcgtg ttcgctctcg ctgctagggt gctcaggaat      420
cctaggctca ggtctctcct cttctctgtg gtggtgatta catctctctt cgtgtctgtg      480
tacggcctca atcagtggat ttacggcgtg gaggagctcg ctacatgggt ggataggaat      540
tctgtggctg atttcacatc tagggtgtac tcttacctcg gcaatcctaa tctcctcgct      600
gcttacctcg tgcctacaac agctttctct gctgctgcta ttggcgtgtg gaggggctgg      660
ctccctaagc tcctcgctat tgctgctaca ggcgcttctt ctctctgcct cattctcaca      720
tactctaggg gcggctggct cggcttcgtg gctatgattt tcgtgtgggc tctcctcggc      780
ctctactggt tccagcctag gctccctgct ccttggagga ggtggctctt ccctgtggtg      840
ctcggcggcc tcgtggctgt gctcctcgtg gctgtgctcg gcctcgagcc tctcagggtg      900
agggtgctct ctattttcgt gggcagggag gattcttcta ataatttcag gattaatgtg      960
tggctcgctg tgctccagat gattcaggat aggccttggc tcggcattgg ccctggcaat     1020
acagctttca atctcgtgta ccctctctac cagcaggcta ggttcacagc tctctctgct     1080
tactctgtgc ctctcgaggt ggctgtggag ggcggcctcc tcggcctcac agctttcgct     1140
tggctcctcc tcgtgacagc tgtgacagct gtgcgccagg tgtctaggct caggagggat     1200
aggaatcctc aggctttctg gctcatggct tctctcgctg gcctcgctgg catgctcggc     1260
catggcctct tcgatacagt gctctacagg cctgaggctt ctacactctg gtggctctgc     1320
attggcgcta ttgcttcttt ctggcagcct cagccttcta gcagctccc tcctgaggct     1380 gagcattctg atgagaagat gtga                                            1404
```

<210> SEQ ID NO 105
<211> LENGTH: 467
<212> TYPE: PRT
<213> ORGANISM: Synechococcus sp.
<220> FEATURE:
<221> NAME/KEY: MISC_FEATURE
<222> LOCATION: (1)..(467)
<223> OTHER INFORMATION: ictB

<400> SEQUENCE: 105

```
Met Thr Val Trp Gln Thr Leu Thr Phe Ala His Tyr Gln Pro Gln Gln
1               5                   10                  15

Trp Gly His Ser Ser Phe Leu His Arg Leu Phe Gly Ser Leu Arg Ala
            20                  25                  30

Trp Arg Ala Ser Ser Gln Leu Leu Val Trp Ser Glu Ala Leu Gly Gly
        35                  40                  45

Phe Leu Leu Ala Val Val Tyr Gly Ser Ala Pro Phe Val Pro Ser Ser
    50                  55                  60

Ala Leu Gly Leu Gly Leu Ala Ala Ile Ala Ala Tyr Trp Ala Leu Leu
65                  70                  75                  80

Ser Leu Thr Asp Ile Asp Leu Arg Gln Ala Thr Pro Ile His Trp Leu
                85                  90                  95

Val Leu Leu Tyr Trp Gly Val Asp Ala Leu Ala Thr Gly Leu Ser Pro
            100                 105                 110

Val Arg Ala Ala Ala Leu Val Gly Leu Ala Lys Leu Thr Leu Tyr Leu
        115                 120                 125

Leu Val Phe Ala Leu Ala Ala Arg Val Leu Arg Asn Pro Arg Leu Arg
```

```
              130                 135                 140
Ser Leu Leu Phe Ser Val Val Ile Thr Ser Leu Phe Val Ser Val
145                 150                 155                 160

Tyr Gly Leu Asn Gln Trp Ile Tyr Gly Val Glu Leu Ala Thr Trp
                165                 170                 175

Val Asp Arg Asn Ser Val Ala Asp Phe Thr Ser Arg Val Tyr Ser Tyr
            180                 185                 190

Leu Gly Asn Pro Asn Leu Leu Ala Ala Tyr Leu Val Pro Thr Thr Ala
            195                 200                 205

Phe Ser Ala Ala Ala Ile Gly Val Trp Arg Gly Trp Leu Pro Lys Leu
            210                 215                 220

Leu Ala Ile Ala Ala Thr Gly Ala Ser Ser Leu Cys Leu Ile Leu Thr
225                 230                 235                 240

Tyr Ser Arg Gly Gly Trp Leu Gly Phe Val Ala Met Ile Phe Val Trp
                245                 250                 255

Ala Leu Leu Gly Leu Tyr Trp Phe Gln Pro Arg Leu Pro Ala Pro Trp
                260                 265                 270

Arg Arg Trp Leu Phe Pro Val Val Leu Gly Gly Leu Ala Val Leu
            275                 280                 285

Leu Val Ala Val Leu Gly Leu Glu Pro Leu Arg Val Arg Val Leu Ser
            290                 295                 300

Ile Phe Val Gly Arg Glu Asp Ser Ser Asn Asn Phe Arg Ile Asn Val
305                 310                 315                 320

Trp Leu Ala Val Leu Gln Met Ile Gln Asp Arg Pro Trp Leu Gly Ile
                325                 330                 335

Gly Pro Gly Asn Thr Ala Phe Asn Leu Val Tyr Pro Leu Tyr Gln Gln
                340                 345                 350

Ala Arg Phe Thr Ala Leu Ser Ala Tyr Ser Val Pro Leu Glu Val Ala
            355                 360                 365

Val Glu Gly Gly Leu Leu Gly Leu Thr Ala Phe Ala Trp Leu Leu Leu
            370                 375                 380

Val Thr Ala Val Thr Ala Val Arg Gln Val Ser Arg Leu Arg Arg Asp
385                 390                 395                 400

Arg Asn Pro Gln Ala Phe Trp Leu Met Ala Ser Leu Ala Gly Leu Ala
                405                 410                 415

Gly Met Leu Gly His Gly Leu Phe Asp Thr Val Leu Tyr Arg Pro Glu
                420                 425                 430

Ala Ser Thr Leu Trp Trp Leu Cys Ile Gly Ala Ile Ala Ser Phe Trp
            435                 440                 445

Gln Pro Gln Pro Ser Lys Gln Leu Pro Pro Glu Ala Glu His Ser Asp
450                 455                 460

Glu Lys Met
465

<210> SEQ ID NO 106
<211> LENGTH: 1533
<212> TYPE: DNA
<213> ORGANISM: Zea mays
<220> FEATURE:
<221> NAME/KEY: misc_feature
<222> LOCATION: (1)..(1533)
<223> OTHER INFORMATION: GRMZM2G004528

<400> SEQUENCE: 106
atgttcatcg agagcttccg cgtcgagagc ccccacgtgc ggtacggccc gacggagatc      60
```

```
gagtcggagt accggtacga cacgacggag ctggtgcacg aggccaagga cggcgcctcc      120
cgctgggtcg tccgccccaa gtccgtcaag tacaacttcc ggaccagcac cgcggtcccc      180
aagctcgggg tcatgcttgt ggggtgggga ggcaacaacg gtccacgct gacggctggg       240 gtcattgcca cagggaggg gatctcatgg gcgaccaagg acaaggtgca gcaagccaac       300
tactacggct ccctcaccca ggcttccacc atcagagtag gcagctacaa cggggaggag      360
atatatgcgc cgttcaagag cctcctaccc atggtgaacc cagacgacct tgtgtttgga      420
ggctgggaca tcagcagcat gaacctggca gatgccatga ccagggccaa ggtgctggac      480
attgacctgc agaagcagct caggccctac atggagtcca tggtgccact tcccggtgtc      540
tatgatccgg acttcatcgc cgctaaccag ggctctcgtg ccaacaatgt catcaagggc      600
accaagaaag aacaggtgga gcagatcatc aaagatatca gggagtttaa ggagaagaac      660
aaagtggaca aggtagttgt gctgtggact gcaaacactg aaaggtacag caatgtatgt      720
gctggtctca cgacacaat ggagaatctg ctggcatctg tggacaagaa cgaggcggag       780
atctcgccat caacactata tgccattgcc tgtgtcacgg agggggtgcc gttcatcaat      840
gggagccccc agaacacttt tgtgcctggg ctgattgatc ttgctatcaa gaacaactgc      900
ctgatcggtg gtgacgactt caagagtggg cagaccaaga tgaaatcggt cctggttgat      960
tttcttgttg gtgctggaat aaagcccacc tcgattgtga gctacaacca cttgggaaac      1020
aacgacggca tgaacctgtc tgcccctcaa acattcaggt ccaaggagat ctccaagagc     1080
aacgtggtgg atgacatggt ctcaagcaat gccattctct atgggcccgg cgagcatccc      1140
gatcatgttg ttgtcatcaa gtatgtgccg tatgtgggag acagtaagag ggctatggac      1200
gagtacacat cagagatctt catgggcggc aagagcacca tcgtgctgca caacacctgc      1260
gaggactcgc tcctcgccgc accgatcatc ctcgatctgg tgctcctggc tgagctcagc      1320
accaggatcc agttaaaacc tgagggaacg acaagttcc actccttcca cccggtggcc       1380
accatcctta gctacctcac caaggcacca ctggttccac ccgcacacc ggtggtgaac       1440 gctcttgcaa agcagagggc gatgctggag aacatcatga gggcttgcgt tggcctggcc      1500
ccagagaaca acatgatcct ggagtacaag tga                                   1533
```

<210> SEQ ID NO 107
<211> LENGTH: 510
<212> TYPE: PRT
<213> ORGANISM: Zea mays
<220> FEATURE:
<221> NAME/KEY: MISC_FEATURE
<222> LOCATION: (1)..(510)
<223> OTHER INFORMATION: GRMZM2G004528

<400> SEQUENCE: 107

```
Met Phe Ile Glu Ser Phe Arg Val Glu Ser Pro His Val Arg Tyr Gly
1               5                   10                  15

Pro Thr Glu Ile Glu Ser Glu Tyr Arg Tyr Asp Thr Thr Glu Leu Val
            20                  25                  30

His Glu Ala Lys Asp Gly Ala Ser Arg Trp Val Val Arg Pro Lys Ser
        35                  40                  45

Val Lys Tyr Asn Phe Arg Thr Ser Thr Ala Val Pro Lys Leu Gly Val
    50                  55                  60

Met Leu Val Gly Trp Gly Gly Asn Asn Gly Ser Thr Leu Thr Ala Gly
65                  70                  75                  80

Val Ile Ala Asn Arg Glu Gly Ile Ser Trp Ala Thr Lys Asp Lys Val
                85                  90                  95
```

```
Gln Gln Ala Asn Tyr Tyr Gly Ser Leu Thr Gln Ala Ser Thr Ile Arg
                100                 105                 110

Val Gly Ser Tyr Asn Gly Glu Glu Ile Tyr Ala Pro Phe Lys Ser Leu
            115                 120                 125

Leu Pro Met Val Asn Pro Asp Asp Leu Val Phe Gly Gly Trp Asp Ile
        130                 135                 140

Ser Ser Met Asn Leu Ala Asp Ala Met Thr Arg Ala Lys Val Leu Asp
145                 150                 155                 160

Ile Asp Leu Gln Lys Gln Leu Arg Pro Tyr Met Glu Ser Met Val Pro
                165                 170                 175

Leu Pro Gly Val Tyr Asp Pro Asp Phe Ile Ala Ala Asn Gln Gly Ser
            180                 185                 190

Arg Ala Asn Asn Val Ile Lys Gly Thr Lys Lys Glu Gln Val Glu Gln
        195                 200                 205

Ile Ile Lys Asp Ile Arg Glu Phe Lys Glu Lys Asn Lys Val Asp Lys
        210                 215                 220

Val Val Val Leu Trp Thr Ala Asn Thr Glu Arg Tyr Ser Asn Val Cys
225                 230                 235                 240

Ala Gly Leu Asn Asp Thr Met Glu Asn Leu Leu Ala Ser Val Asp Lys
                245                 250                 255

Asn Glu Ala Glu Ile Ser Pro Ser Thr Leu Tyr Ala Ile Ala Cys Val
            260                 265                 270

Thr Glu Gly Val Pro Phe Ile Asn Gly Ser Pro Gln Asn Thr Phe Val
        275                 280                 285

Pro Gly Leu Ile Asp Leu Ala Ile Lys Asn Asn Cys Leu Ile Gly Gly
        290                 295                 300

Asp Asp Phe Lys Ser Gly Gln Thr Lys Met Lys Ser Val Leu Val Asp
305                 310                 315                 320

Phe Leu Val Gly Ala Gly Ile Lys Pro Thr Ser Ile Val Ser Tyr Asn
                325                 330                 335

His Leu Gly Asn Asn Asp Gly Met Asn Leu Ser Ala Pro Gln Thr Phe
            340                 345                 350

Arg Ser Lys Glu Ile Ser Lys Ser Asn Val Val Asp Asp Met Val Ser
        355                 360                 365

Ser Asn Ala Ile Leu Tyr Gly Pro Gly Glu His Pro Asp His Val Val
        370                 375                 380

Val Ile Lys Tyr Val Pro Tyr Val Gly Asp Ser Lys Arg Ala Met Asp
385                 390                 395                 400

Glu Tyr Thr Ser Glu Ile Phe Met Gly Gly Lys Ser Thr Ile Val Leu
                405                 410                 415

His Asn Thr Cys Glu Asp Ser Leu Leu Ala Ala Pro Ile Ile Leu Asp
            420                 425                 430

Leu Val Leu Leu Ala Glu Leu Ser Thr Arg Ile Gln Leu Lys Pro Glu
        435                 440                 445

Gly Thr Asp Lys Phe His Ser Phe His Pro Val Ala Thr Ile Leu Ser
        450                 455                 460

Tyr Leu Thr Lys Ala Pro Leu Val Pro Pro Gly Thr Pro Val Val Asn
465                 470                 475                 480

Ala Leu Ala Lys Gln Arg Ala Met Leu Glu Asn Ile Met Arg Ala Cys
                485                 490                 495

Val Gly Leu Ala Pro Glu Asn Asn Met Ile Leu Glu Tyr Lys
            500                 505                 510
```

<210> SEQ ID NO 108
<211> LENGTH: 1497
<212> TYPE: DNA
<213> ORGANISM: Oryza sativa
<220> FEATURE:
<221> NAME/KEY: promoter
<222> LOCATION: (1)..(1497)
<223> OTHER INFORMATION: OsRbcS promoter

<400> SEQUENCE: 108

```
gaaccatacg gaattgacgg accaattgtg catacggact tagctaaaat aattgttgat      60
ttttggcaat aagaaaagcg agtagcacat aaaatctaaa gtggatgagt aaagggacaa     120
aatttttatac atgttcaggc cttctcgatg agaagtaata ctatactcct gttttgggga    180
ttatatttgt cagatgttgt atcaatctga cgatcgagtt atggttattg ttggcggctg     240
ttaaatatcg atttttatgcc atcaatacct gtataattta tacagaaata ataaaacatt    300
caacatagtg gtaggcttta attctaacat attccataag tgttggtgta tatttggatg     360
caggtaataa accaccgaat taggaggaaa tctagactaa gttgaaggaa attttcatcc     420
atacaagtgt tgggctttttt aactccattt taacaccaaa atgcaagccc aaaaacctgc    480
gaaatggata aggcagactg agaaggaggc ccaggccaaa acttgggcca gttgggccaa     540
gccaggtttc ggccaaatcc tgatcatcgc tgttgatctc agggtttggc atggacgctc     600
ttgatttact cctgatggca gttgcagggc atttccgatc attcgcatgc tctacaacca    660
tcatacctac ttatttaagg agctctcatc ctcacttcat atcacacact ccaatcttga    720
gctgaattat aagaggctct attgtatttt attgtatact agaattaggg aaagattaag    780
gtcgtagaag aaatcggagg aattccggag ttatcggtga tccttttcta tttcttatac    840
tttgttatttt gctttaatag aaatatcatt tcaagtaatt aagatttgtt tagtgagaac    900
tattattggc tagttcctaa ttagcgtatg agatcactgt tcactataat ccgttaaaat    960
atagtgattg cttagtgag ttacaaacac tacagtagtt attgattgct taaacgtggt    1020
gtttagatag ttaatttcta gtggttgctg cgtatcccat agtacgttag aggcgggtgt    1080
agaggtggtg accgccctca agagcactta attcctcctt gtttgtgtac gtggtagagc    1140
gacatctggg aacagtgggt taccagtgcc tgaagtacca tgttaggatt aaaattgtaa    1200
cattgttttct cattagtaaa tcttctctac cctctaccca catttgcttt gtatccttgg    1260
tgaacctgaa gaggaactga acacacacgt tccatgagga agacactcag tactcaagcc    1320
ggaggcagca cactgcaact taagtttttc tatagctcct agcaagctag caatggctcc    1380
ctcggtgatg gcttcgtcgg ccacctccgt ggctcccttc caggggctca agtccactgc    1440
gggcctcccg gtgaaccgcc gctccagcag ctcgagcttt gcaacgtca gcatcga       1497
```

<210> SEQ ID NO 109
<211> LENGTH: 888
<212> TYPE: DNA
<213> ORGANISM: Zea mays
<220> FEATURE:
<221> NAME/KEY: misc_feature
<222> LOCATION: (1)..(888)
<223> OTHER INFORMATION: GRMZM2G075336

<400> SEQUENCE: 109

```
atggccggcg aagggaatgg ggatgaaggg tggaggcgga gcggcatcga ggtcagcgcc      60
ctgcagttcg gctacgacgg gcagccgccg ctcttcgcgc gcttcaacct ctgcgtcgca    120
cccggctccc gctgcctcct cgtcggcgcc aacggatcag gcaagaccac actcttgaag    180
```

```
attcttgcgg gaaagcatat ggttggagga agagatgtgg tccgtgtcct caatggttcc    240
gcttttcatg atacacagct agtgtgcaat ggtgacctttt cgtacttggg tggttcttgg    300
agccgtacta ttggttcagc tggggatgtt ccactgcaag gcgacttctc tgctgagcac    360 atgattttttg gagttgatgg ggttgatcct gtcaggcgag agaagctggt tgatctgcta    420
gacattgatc tgcagtggcg catgcataaa gtttcagatg ggcagcgccg cagggtgcaa    480
atctgcatgg gtcttcttca tccatacaag gtgcttttgc tcgatgagat cacgttgat    540 ctggacgtgg tgaccaggat ggacctgctt ggtttcttca aggaagagtg cgagcagagg    600
gaagctacca tcgtgtacgc cacccatata tttgacggac tcgagacgtg ggctaccgac    660
tttgcgtaca tccaagaagg cgagctgaga aggtccggga gatactccga catcgaggag    720
ctaaggagcg ccaagaactt gctgtcggta gtcgagtcgt ggctgaggtc agagaccaaa    780
cttccgaaga aggaaccccc accacgtcct gagacccagg ccaggcgttc ctcgccgttc    840
gatgcttctc ctttccgttc gtcacgccac atggcctact accgttga                 888
```

<210> SEQ ID NO 110
<211> LENGTH: 295
<212> TYPE: PRT
<213> ORGANISM: Zea mays
<220> FEATURE:
<221> NAME/KEY: MISC_FEATURE
<222> LOCATION: (1)..(295)
<223> OTHER INFORMATION: GRMZM2G075336

<400> SEQUENCE: 110

```
Met Ala Gly Glu Gly Asn Gly Asp Glu Gly Trp Arg Arg Ser Gly Ile
1               5                   10                  15

Glu Val Ser Ala Leu Gln Phe Gly Tyr Asp Gly Gln Pro Pro Leu Phe
            20                  25                  30

Ala Arg Phe Asn Leu Cys Val Ala Pro Gly Ser Arg Cys Leu Leu Val
        35                  40                  45

Gly Ala Asn Gly Ser Gly Lys Thr Thr Leu Leu Lys Ile Leu Ala Gly
    50                  55                  60

Lys His Met Val Gly Gly Arg Asp Val Arg Val Leu Asn Gly Ser
65                  70                  75                  80

Ala Phe His Asp Thr Gln Leu Val Cys Asn Gly Asp Leu Ser Tyr Leu
                85                  90                  95

Gly Gly Ser Trp Ser Arg Thr Ile Gly Ser Ala Gly Asp Val Pro Leu
            100                 105                 110

Gln Gly Asp Phe Ser Ala Glu His Met Ile Phe Gly Val Asp Gly Val
        115                 120                 125

Asp Pro Val Arg Arg Glu Lys Leu Val Asp Leu Leu Asp Ile Asp Leu
    130                 135                 140

Gln Trp Arg Met His Lys Val Ser Asp Gly Gln Arg Arg Val Gln
145                 150                 155                 160

Ile Cys Met Gly Leu Leu His Pro Tyr Lys Val Leu Leu Leu Asp Glu
                165                 170                 175

Ile Thr Val Asp Leu Asp Val Val Thr Arg Met Asp Leu Leu Gly Phe
            180                 185                 190

Phe Lys Glu Glu Cys Glu Gln Arg Glu Ala Thr Ile Val Tyr Ala Thr
        195                 200                 205

His Ile Phe Asp Gly Leu Glu Thr Trp Ala Thr Asp Phe Ala Tyr Ile
    210                 215                 220
```

```
Gln Glu Gly Glu Leu Arg Arg Ser Gly Arg Tyr Ser Asp Ile Glu Glu
225                 230                 235                 240

Leu Arg Ser Ala Lys Asn Leu Leu Ser Val Val Glu Ser Trp Leu Arg
            245                 250                 255

Ser Glu Thr Lys Leu Pro Lys Lys Glu Pro Pro Arg Pro Glu Thr
        260                 265                 270

Gln Ala Arg Arg Ser Ser Pro Phe Asp Ala Ser Pro Phe Arg Ser Ser
        275                 280                 285

Arg His Met Ala Tyr Tyr Arg
        290             295

<210> SEQ ID NO 111
<211> LENGTH: 1429
<212> TYPE: DNA
<213> ORGANISM: Oryza sativa
<220> FEATURE:
<221> NAME/KEY: 3'UTR
<222> LOCATION: (1)..(1429)
<223> OTHER INFORMATION: OsRbcS 3'UTR

<400> SEQUENCE: 111
gttcgcgctt tcgttccttc gtgcatgttc tttctttttc tttttttttt gtgtgtccgt      60
gttaagctgc acgtaattgt tctctcgcgc tccgacctgc cgttgttgca agagtactac     120
tacaactatc ggtctatcgt tcggtgacgg tgagacaggg cacgtgaatg caagatctcc     180
ggctatacac acgtactcat gtaatatgat gcctagagca tatctgaatc cgtcgacaat     240
gaaattttgg ttttgcaaaa tgctggtatt tgtttatcat cctggcacgt gatatttgcc     300
tagagcatct aaatcacttt tacgaaatgt gcgcgtcaac aaactgatac ggcccaaatg     360
ccagaaatta ccagcatata tagccatatc aacttttgat tcgtatatat gaaggttgat     420
ttagttagag aaattcggtt gtgagagaag gaggctagca aagattcggt tgatcaagct     480
gtaccgccag gccaggacgt gctgtgcgcg cggctgtgcc gcttgaccgc agaaccatac     540
ggaattgacg gaccaattgt gcatacggac ttagctaaaa taattgttga ttttttggcaa     600
taagaaaagc gagtagcaca taaaatctaa agtggatgag taaagggaca aaattttata     660
catgttcagg ccttctcgat gagaagtaat actatactcc tgttttgggg attatatttg     720
tcagatgttg tatcaatctg acgatcgagt tatggttatt gttggcggct gttaaatatc     780
gattttatgc catcaatacc tgtataattt atacagaaat aataaaacat tcaacatagt     840
ggtaggcttt aattctaaca tattccataa gtgttggtgt atatttggat gcaggtaata     900
aaccaccgaa ttaggaggaa atctagacta agttgaagga aattttcatc catacaagtg     960
ttgggctttt taactccatt ttaacaccaa aatgcaagcc caaaacctg cgaaatggat    1020
aaggcagact gagaaggagg cccaggccaa aacttgggcc agttgggcca agccaggttt    1080
cggccaaatc ctgatcatcg ctgttgatct cagggtttgg catggacgct cttgatttac    1140
tcctgatggc agttgcaggg catttccgat cattcgcatg ctctacaacc atcataccta    1200
cttatttaag gagctctcat cctcacttca tatcacacac tccaatcttg agctgaatta    1260
taagaggctc tattgtattt tattgtatac tagaattagg gaaagattaa ggtcgtagaa    1320
gaaatcggag gaattccgga gttatcggtg atccttttct atttcttata ctttgttatt    1380
tgctttaata gaaatatcat ttcaagtaat taagatttgt ttagtgaga                1429

<210> SEQ ID NO 112
<211> LENGTH: 798
<212> TYPE: DNA
```

<213> ORGANISM: Zea mays
<220> FEATURE:
<221> NAME/KEY: promoter
<222> LOCATION: (1)..(798)
<223> OTHER INFORMATION: ZmRbcS7A promoter

<400> SEQUENCE: 112

```
gatgactgat gacagacgtg gggaattcaa atgcaactct agcgaaagtt catatatttt      60
tcataaatag ctgaggctgg ggtaattatt tttttttgtag aaaaatagaa taggtggaat    120
ggttggggaa ggcgtaggcg ctcgtggacg acgcccgata aaagacaaga ggcggaattg    180
ccatgaattc gaggtagcta agtaaggcgc atatatatgc caaaaaattc tactgtcact    240
ttccaatttc aatgcgctgc caaacaagcc atcctggaaa ctgacttgaa ttcagcccaa    300
ttctgtagat ccaaacaggg ccggcgtcag tgcctcaggt gagagagcag cagacgatgc    360
aaagagccaa aactgcaagc agacgcagcc gaagccgaag ccgaagccca gcccaaaac     420
tgttttgtct ttgcccagaa ccgcgacgag cctaaactgc gcttcctcct atctacaagt    480
ccctggcaca tcacgcatag tccaaccatg gcgcgcaggc gataaggcga ccacgggga     540
cgcgacatgt ggtggcggac gcgatcagga tagggccagg ctggccgggc gcggccacgg    600
gatctagatg gccactcgtc ccacatccgc ttcgtcctgt cctgtactgc gtcctgcccc    660
caacgagagc cggagccggc catcccgtcg cacactctcc ccctctatat atgccgtcgg    720
tgtgggggag cctactacag gacgacccaa gcaagcaagc aagcagcgag tacatacata    780
ctaggcagcc aggcagcc                                                  798
```

<210> SEQ ID NO 113
<211> LENGTH: 459
<212> TYPE: DNA
<213> ORGANISM: Zea mays
<220> FEATURE:
<221> NAME/KEY: misc_feature
<222> LOCATION: (1)..(459)
<223> OTHER INFORMATION: GRMZM2G122793

<400> SEQUENCE: 113

```
atgacatcca ccgtcaccac aaccgttggg tgcgggggggc tccccgtccg cccgttgtcg      60
acagcgacca gaggacgccc acgcagatgc gccgtccgag cccaggccgc gggagcggat    120
gcctccaatg ataagtcagt ggaggtcatg cgcaagttct ccgagcagta cgcccgccgc    180
tccaacactt tcttctgcgc cgacaagaca gtcactgccg tcgtcatcaa gggacttgct    240
gatcacaggg atactcttgg agctcctcta tgcccttgta ggcattatga tgacaaagct    300
gcggaggtag cacaaggatt ttggaattgc ccatgcgtcc ccatgcgtga gaggaaggaa    360
tgccactgta tgcttttttct tactcccgat aatgactttg ctgggaagga tcaggttatc    420
tccttcgagg agatcaaaga ggcgacatcg aagttctaa                           459
```

<210> SEQ ID NO 114
<211> LENGTH: 152
<212> TYPE: PRT
<213> ORGANISM: Zea mays
<220> FEATURE:
<221> NAME/KEY: MISC_FEATURE
<222> LOCATION: (1)..(152)
<223> OTHER INFORMATION: GRMZM2G122793

<400> SEQUENCE: 114

```
Met Thr Ser Thr Val Thr Thr Thr Val Gly Cys Gly Gly Leu Pro Val
1               5                   10                  15
```

```
Arg Pro Leu Ser Thr Ala Thr Arg Gly Arg Pro Arg Arg Cys Ala Val
            20              25              30

Arg Ala Gln Ala Ala Gly Ala Asp Ala Ser Asn Asp Lys Ser Val Glu
        35              40              45

Val Met Arg Lys Phe Ser Glu Gln Tyr Ala Arg Arg Ser Asn Thr Phe
    50              55              60

Phe Cys Ala Asp Lys Thr Val Thr Ala Val Val Ile Lys Gly Leu Ala
65              70              75              80

Asp His Arg Asp Thr Leu Gly Ala Pro Leu Cys Pro Cys Arg His Tyr
            85              90              95

Asp Asp Lys Ala Ala Glu Val Ala Gln Gly Phe Trp Asn Cys Pro Cys
            100             105             110

Val Pro Met Arg Glu Arg Lys Glu Cys His Cys Met Leu Phe Leu Thr
            115             120             125

Pro Asp Asn Asp Phe Ala Gly Lys Asp Gln Val Ile Ser Phe Glu Glu
            130             135             140

Ile Lys Glu Ala Thr Ser Lys Phe
145             150
```

INCREASING PLANT GROWTH AND YIELD BY EXPRESSION OF AN M-TYPE THIOREDOXIN

CROSS-REFERENCE TO RELATED APPLICATIONS

This application is a national stage filing under 35 U.S.C. 371 of PCT/IB2017/053883 filed Jun. 28, 2017, which International Application was published by the International Bureau in English on Jan. 4, 2018, and claims priority from U.S. Provisional Application No. 62/356,120, filed Jun. 29, 2016 which applications are hereby incorporated by reference in their entirety in this application.

FIELD OF THE INVENTION

The invention is drawn to compositions and methods for increasing plant growth and yield through expression of a thioredoxin gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one thioredoxin gene in a plant of interest. The invention also encompasses constructs comprising a promoter that drives expression in a plant cell operably linked to a thioredoxin coding sequence. Compositions further comprise plants, plant seeds, plant organs, plant cells, and other plant parts that have increased expression of a thioredoxin sequence. The invention includes methods that can be utilized to increase expression of a thioredoxin gene in a plant. Such thioredoxin gene may be a native sequence or alternatively, may be a sequence that is heterologous to the plant of interest.

Embodiments of the invention include:
1. A method for increasing crop yield comprising transforming a plant with at least one thioredoxin protein-encoding sequence.
2. The method of embodiment 1, wherein said thioredoxin protein-encoding sequence comprises SEQ ID NO:1, or encodes a protein selected from the group consisting of SEQ ID NOs:2 and 17-100.
3. The method of embodiment 1, wherein said thioredoxin protein-encoding sequence encodes a protein with at least 80%, 90%, 95%, 96%, 97%, 98%, or 99% sequence identity to a sequence selected from the group consisting of SEQ ID NOs:2 and 17-100, and that has thioredoxin function.
4. The method of embodiment 1, wherein said thioredoxin protein-encoding sequence encodes a protein with at least 80%, 85%, 90%, 95%, 96%, 97%, 98%, or 99% sequence positives relative to a sequence selected from the group consisting of SEQ ID NOs:2 and 17-100, and that has thioredoxin function.
5. A plant having stably incorporated into its genome a promoter that drives expression in a plant operably linked to a thioredoxin protein-encoding sequence, wherein said promoter is heterologous to said thioredoxin protein-encoding sequence.
6. The plant of embodiment 5, wherein said thioredoxin protein-encoding sequence comprises SEQ ID NO:1, or encodes a protein selected from the group consisting of SEQ ID NOs:2 and 17-100.
7. The plant of embodiment 5, wherein said thioredoxin protein-encoding sequence encodes a protein with at least 80%, 85%, 90%, 95%, 96%, 97%, 98%, or 99% sequence identity to a sequence selected from the group consisting of SEQ ID NOs:2 and 17-100, and that has thioredoxin function.
8. The plant of embodiment 5, wherein said thioredoxin protein-encoding sequence encodes a protein with at least 80%, 85%, 90%, 95%, 96%, 97%, 98%, or 99% sequence positives relative to a sequence selected from the group consisting of SEQ ID NOs:2 and 17-100, and that has thioredoxin function.

9. Transformed seed of any one of the plants of embodiments 5-8.

10. The plant of any one of embodiments 5-8 wherein said plant is a monocot.

11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum.*

12. The plant of any one of embodiments 5-8 wherein said plant is a dicot.

13. The plant of embodiment 12 wherein said plant is from the genus Glycine, *Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus,* or *Eucalyptus.*

14. The plant of any one of embodiments 5-8 wherein said plant exhibits increased growth relative to a control plant.

15. The plant of any one of embodiments 5-8 wherein said plant exhibits increased biomass yield relative to a control plant.

16. The plant of any one of embodiments 5-8 wherein said plant exhibits increased seed yield relative to a control plant.

17. The method of any one of embodiments 1-4, wherein said thioredoxin protein-encoding sequence is expressed from a constitutive promoter.

18. The method of embodiment 17, wherein said constitutive promoter comprises SEQ ID NO:3.

19. The method of any one of embodiments 1-4, wherein said thioredoxin protein-encoding sequence is expressed from a bundle sheath-preferred promoter.

20. The method of embodiment 19, wherein said bundle sheath-preferred promoter is selected from the group of SEQ ID NOs:5 and 9.

21. The method of any one of embodiments 1-4, wherein said thioredoxin protein-encoding sequence is expressed from a mesophyll-preferred promoter.

22. The method of embodiment 21, wherein said mesophyll-preferred promoter is selected from the group of SEQ ID NOs:7 and 10.

23. The plant of any one of embodiments 5-8, wherein said promoter that drives expression in a plant is a constitutive promoter.

24. The plant of embodiment 23, wherein said constitutive promoter comprises SEQ ID NO:3.

25. The plant of any one of embodiments 5-8, wherein said promoter that drives expression in a plant is a bundle sheath-preferred promoter.

26. The plant of embodiment 25, wherein said bundle sheath-preferred promoter is selected from the group of SEQ ID NOs:5 and 9.

27. The plant of any one of embodiments 5-8, wherein said promoter that drives expression in a plant is a mesophyll-preferred promoter.

28. The plant of embodiment 27, wherein said mesophyll-preferred promoter is selected from the group of SEQ ID NOs:7 and 10.

29. A DNA construct comprising, in operable linkage,
   a. A promoter that is functional in a plant cell and,
   b. A nucleic acid sequence encoding a thioredoxin protein.

30. The DNA construct of embodiment 29, wherein said nucleic acid sequence encoding a thioredoxin protein comprises SEQ ID NO:1, or encodes a protein selected from the group consisting of SEQ ID NOs:2 and 17-100.

31. The DNA construct of embodiment 29 or 30, wherein said nucleic acid sequence encoding a thioredoxin protein encodes a protein with at least 80%, 85%, 90%, 95%, 96%, 97%, 98%, or 99% sequence identity to a sequence selected from the group consisting of SEQ ID NOs:2 and 17-100, and that has thioredoxin function.

32. The DNA construct of embodiment 29 or 30, wherein said nucleic acid sequence encoding a thioredoxin protein encodes a protein with at least 80%, 85%, 90%, 95%, 96%, 97%, 98%, or 99% sequence positives relative to a sequence selected from the group consisting of SEQ ID NOs:2 and 17-100, and that has thioredoxin function.

33. The DNA construct of embodiment 29 or 30, wherein said promoter that is functional in a plant cell is selected from the group of SEQ ID NOs:3, 5, 7, 9, and 10.

34. The DNA construct of any one of embodiments 29-33, wherein said promoter is heterologous to said nucleic acid sequence encoding a thioredoxin protein.

35. A method for increasing crop yield comprising modulating the expression of at least one thioredoxin protein-encoding sequence in a plant.

36. The method of embodiment 35 wherein said modulating the expression comprises increasing the expression of at least one thioredoxin protein-encoding sequence in a plant.

37. The method of embodiment 36, wherein said increasing the expression comprises increasing the activity of a native thioredoxin sequence in said plant or increasing activity of a native thioredoxin protein-encoding sequence in said plant.

38. The method of any one of embodiments 1-4, wherein said thioredoxin protein-encoding sequence encodes an m-type thioredoxin.

39. The plant of any one of embodiments 5-8, wherein said thioredoxin protein-encoding sequence encodes an m-type thioredoxin.

40. The DNA construct of any one of embodiments 29-34, wherein said thioredoxin protein is an m-type thioredoxin.

41. The method of any one of embodiments 35-37, wherein said thioredoxin protein-encoding sequence encodes an m-type thioredoxin.

42. The plant of any one of embodiments 5-8, wherein said promoter that drives expression in a plant is active in leaf tissue.

43. The DNA construct of any one of embodiments 29-34, wherein said promoter that is functional in a plant cell is active in leaf tissue.

44. The method of any one of embodiments 1-4, further comprising transforming a plant with at least one additional protein-encoding sequence.

45. The method of embodiment 44 wherein said additional protein-encoding sequence shares at least 70% identity with a sequence selected from the group of SEQ ID NOs:13, 15, 101, 104, 106, 109, and 113, or encodes a protein that shares at least 80% identity with a sequence selected from the group of SEQ ID NOs:14, 16, 102, 105, 107, 110, and 114.

46. The method of embodiment 45 wherein said additional protein-encoding sequence comprises a sequence selected from the group of SEQ ID NOs:13, 15, 101, 104, 106, 109, and 113, or encodes a protein that comprises a sequence selected from the group of SEQ ID NOs:14, 16, 102, 105, 107, 110, and 114.

47. The plant of any one of embodiments 5-8, wherein said plant has stably incorporated into its genome a second promoter that drives expression of at least one additional coding sequence, wherein said second promoter is heterologous to said additional coding sequence.

48. The plant of embodiment 47, wherein said additional coding sequence shares at least 70% identity with a sequence selected from the group of SEQ ID NOs: 13, 15, 101, 104, 106, 109, and 113, or encodes a protein that shares at least 80% identity with a sequence selected from the group of SEQ ID NOs: 14, 16, 102, 105, 107, 110, and 114.

49. The plant of embodiment 48, wherein said additional coding sequence comprises a sequence selected from the group of SEQ ID NOs: 13, 15, 101, 104, 106, 109, and 113, or encodes a protein that comprises a sequence selected from the group of SEQ ID NOs: 14, 16, 102, 105, 107, 110, and 114.

50. The DNA construct of any one of embodiments 29-34, further comprising, in operable linkage,
   a. A second promoter that is functional in a plant cell and,
   b. A nucleic acid sequence encoding an additional protein,
   wherein said second promoter is heterologous to said nucleic acid sequence encoding an additional protein.

51. The DNA construct of embodiment 50, wherein said nucleic acid sequence encoding an additional protein shares at least 70% identity with a sequence selected from the group of SEQ ID NOs: 13, 15, 101, 104, 106, 109, and 113, or encodes a protein that shares at least 80% identity with a sequence selected from the group of SEQ ID NOs: 14, 16, 102, 105, 107, 110, and 114.

52. The DNA construct of embodiment 51, wherein said nucleic acid sequence encoding an additional protein comprises a sequence selected from the group of SEQ ID NOs: 13, 15, 101, 104, 106, 109, and 113, or encodes a protein that comprises a sequence selected from the group of SEQ ID NOs: 14, 16, 102, 105, 107, 110, and 114.

DETAILED DESCRIPTION OF THE INVENTION

Compositions and methods for increasing crop biomass and yield are provided. The methods include increasing the expression of at least one thioredoxin gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found belowground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding a thioredoxin protein. In a preferred embodiment, the expression of a thioredoxin-encoding gene is upregulated relative to thioredoxin expression levels in a control plant, resulting in increased harvestable biomass in plants with increased thioredoxin expression relative to control plants. In a preferred embodiment, the thioredoxin gene whose expression is modulated encodes an m-type thioredoxin protein. Any methods for increasing the activity or expression of a thioredoxin-encoding sequence in a plant are encompassed by the present invention.

The compositions of the invention include constructs comprising the coding sequence set forth in SEQ ID NO:1 or encoding a protein selected from the group of SEQ ID NOs:2 and 17-100 or variants thereof, operably linked to a promoter that is functional in a plant cell. By "promoter" is intended to mean a regulatory region of DNA that is capable of driving expression of a sequence in a plant or plant cell. It is recognized that having identified the thioredoxin protein sequences disclosed herein, it is within the state of the art to isolate and identify additional thioredoxin protein sequences and nucleotide sequences encoding thioredoxin protein sequences, for instance through BLAST searches, PCR assays, and the like.

The coding sequences of the present invention, when assembled within a DNA construct such that a promoter is operably linked to the coding sequence of interest, enable expression and accumulation of thioredoxin protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the thioredoxin proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the thioredoxin protein-encoding nucleotide sequence. While the thioredoxin-encoding nucleotide sequence and the promoter sequence are heterologous to each other, either the thioredoxin-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain thioredoxin function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as the ability to facilitate the reduction of cysteine disulfide bonds in proteins in conjunction with ferredoxin and ferredoxin-thioredoxin reductase or with NADPH and NADP-thioredoxin reductase. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

| Classes of Amino Acids | |
|---|---|
| Amino Acid Class | Example Amino Acids |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding thioredoxin proteins, i.e. upregulating expression. Likewise, in some instances, plant growth and yield may be increased by decreasing the expression levels of one or more genes encoding thioredoxin proteins, i.e. downregulating expression. Thus, the invention encompasses the upregulation or downregulation of one or more genes encoding thioredoxin proteins. Further, the methods include the upregulation of at least one gene encoding a thioredoxin protein and the downregulation of at least one gene encoding a second thioredoxin protein in a plant of interest. By modulating the concentration and/or activity of at least one of the genes encoding a thioredoxin protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding thioredoxin proteins of the present invention can be controlled by the use of one or more promoters that are functional in a plant cell. The expression level of the thioredoxin protein-encoding gene of interest may be measured directly, for example, by assaying for the level of the photosynthetic gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. Thioredoxin function can be assessed by measuring the reduction of insulin disulfide with dithiothreitol (DTT), as described elsewhere (Li et al. (1996) *Plant J* 10:505-513).

A "subject plant or plant cell" is one in which genetic alteration, such as transformation, has been effected as to a thioredoxin protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of a thioredoxin protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of a thioredoxin protein-encoding gene of interest, antisense constructions, complementary to at least a portion of the messenger RNA (mRNA) for the sequences of a gene of interest, particularly a gene encoding a thioredoxin protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding thioredoxin proteins can be identified and used in the methods of the invention. The variant sequences will retain the biological activity of a thioredoxin protein (i.e., an ability to act as an electron donor to facilitate the reduction of cysteine disulfide bonds in conjunction with ferredoxin and ferredoxin-thioredoxin reductase or with NADPH and NADP-thioredoxin reductase). Thioredoxin proteins have been grouped into different classes, including m-type, f-type, h-type, x-type, y-type, and o-type (Buchanan and Balmer (2005) Annu Rev Plant Biol 56:187-220). Classification of thioredoxins by type is determined by the primary structure of the thioredoxin proteins (Schürmann and Jacquot (2000) Annu Rev Plant Physiol Plant Mol Biol 51:371-400). The m- and f-type thioredoxins are present in higher plant chloroplasts, and a number of researchers have shown that these m-type and f-type thioredoxins participate in the regulation of the redox state of a number of chloroplast proteins, including photosynthetic proteins. This redox regulation in turn regulates the activity of these proteins, which affects the metabolic activity in and growth of the plant. M-type thioredoxins have been linked to plant yield, as shown by Okegawa et al., who tested *Arabidopsis* lines deficient in thioredoxin m and showed that decreased expression of thioredoxin genes led to decreased growth and photosynthetic assimilation (Okegawa et al. (2015) *Plant J* 84:900-913). Experiments in which m-type thioredoxin expression was increased also showed that thioredoxin overexpression in tobacco led to impaired growth (Rey et al. (2013) *Front Plant Sci* 4:1-13). The present invention shows that, unexpectedly, certain novel expression strategies for thioredoxin overexpression can lead to increased biomass and seed yield.

The expression cassette will include in the 5'-3' direction of transcription, a transcriptional and translational initiation region, a polynucleotide encoding a thioredoxin protein of the present invention, and a transcriptional and translational termination region (i.e., termination region) functional in plants.

A number of promoters may be used in the practice of the invention. The polynucleotides encoding a thioredoxin protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding thioredoxin proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Developmentally-regulated promoters may be desirable for the expression of a polynucleotide encoding a thioredoxin protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding a thioredoxin protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding a thioredoxin protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding thioredoxin proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding a thioredoxin protein of the present invention is used to transform a plant cell or cells. The transformed plant cell or cells are regenerated to produce transformed plants. These plants transformed with a construct comprising a functional promoter driving expression of a thioredoxin protein-encoding polynucleotide of the invention demonstrated increased plant yield, i.e., increased above-ground biomass and/or increased seed yield.

Now that it has been demonstrated that upregulation of thioredoxin increases plant yield, other methods for increasing expression of an endogenous thioredoxin sequence in a plant of interest can be used. The expression of a thioredoxin gene present in a plant's genome can be altered by inserting a transcriptional enhancer upstream of the thioredoxin gene present in the plant's genome. This strategy will allow the thioredoxin gene's expression to retain its normal developmental profile, while showing elevated transcript levels. This strategy will occur through the insertion of an enhancer element upstream of a thioredoxin gene of interest using a meganuclease designed against the genomic sequence of interest. Alternatively, a Cas9 endonuclease coupled with a guide RNA (gRNA) designed against the genomic sequence of interest, or a cpf1 endonuclease coupled with a gRNA designed against the genomic sequence of interest, is used to effect the insertion of an enhancer element upstream of a thioredoxin gene of interest. Alternatively, a deactivated Cas9 endonuclease fused to a transcriptional enhancer element is targeted to a genomic location near the transcription start site for a thioredoxin gene of interest, thereby modulating the expression of said thioredoxin gene of interest (Piatek et al. (2015) *Plant Biotechnol J* 13:578-589).

Modulation of the expression of a thioredoxin protein-encoding gene may be achieved through the use of precise genome-editing technologies to modulate the expression of the endogenous sequence. In this manner, a nucleic acid sequence will be inserted proximal to a native plant sequence encoding the thioredoxin through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163: 759-771, U.S. Provisional Patent Application 62/295,325); *N. gregoryi* Argonaute-mediated DNA insertion (Gao et al. (2016) *Nat Biotechnol* doi: 10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of a thioredoxin gene.

Enhancers include any molecule capable of enhancing gene expression when inserted into the genome of a plant. Thus, an enhancer can be inserted in a region of the genome upstream or downstream of a thioredoxin sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding a thioredoxin protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of thioredoxin gene expression may also be achieved through the modification of DNA in a way that does not alter the sequence of the DNA. Such changes could include modifying the chromatin content or structure of the thioredoxin gene of interest and/or of the DNA surrounding the thioredoxin gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the thioredoxin gene of interest and/or of the DNA surrounding the thioredoxin gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the thioredoxin gene of interest may be applied in order to achieve the desired result of an altered thioredoxin gene expression profile.

Alteration of thioredoxin gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding thioredoxin may be achieved by inserting a transposable element upstream of the thioredoxin gene of interest, causing the expression of said gene to be altered.

Alteration of thioredoxin gene expression may also be achieved through expression of a transcription factor or transcription factors that regulate the expression of the thioredoxin gene of interest. It is well understood that alteration of transcription factor expression can in turn alter the expression of the target gene(s) of said transcription factor (Hiratsu et al. (2003) *Plant J* 34:733-739). Alteration of thioredoxin gene expression may be achieved by altering the expression of transcription factor(s) that are known to interact with the thioredoxin gene of interest (e.g., the CCA1 transcription factor (Barajas-López et al. (2011) 62:2039-2051).

Alteration of thioredoxin gene expression may also be achieved through the insertion of a promoter upstream of the open reading frame encoding a native thioredoxin in the plant species of interest. This will occur through the insertion of a promoter of interest upstream of a thioredoxin protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpf1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

EXPERIMENTAL

Example 1—Construction of Thioredoxin Plant Transformation Vectors

An open reading frame encoding a maize m-type thioredoxin protein was synthesized. This open reading frame comprised SEQ ID NO:1, encoding the protein sequence of SEQ ID NO:2. Appropriate restriction sites were included at the 5' and 3' ends of the coding sequence to allow this DNA to be cloned into plant transformation vectors that contained genetic elements suitable for controlling gene expression. In each plant transformation construct, the thioredoxin open reading frame was located downstream of a plant promoter and 5' untranslated region (5'UTR) and upstream of a 3'UTR. Table 2 summarizes the plant transformation constructs that were built containing a thioredoxin open reading frame.

TABLE 2

Thioredoxin plant transformation constructs

| Construct ID | Promoter + 5'UTR | ORF | 3'UTR |
|---|---|---|---|
| 130607 | 2X 35S (SEQ ID NO: 3) | thioredoxin (SEQ ID NO: 1, encoding SEQ ID NO: 2) | 35S poly A (SEQ ID NO: 4) |
| 130994 | ZmRbcS (SEQ ID NO: 5) | thioredoxin (SEQ ID NO: 1, encoding SEQ ID NO: 2) | ZmRbcS (SEQ ID NO: 6) |
| 131092 | 4xRGCGR (SEQ ID NO: 7) | thioredoxin (SEQ ID NO: 1, encoding SEQ ID NO: 2) | ZmCA (SEQ ID NO: 8) |
| 131172 | GLDC (SEQ ID NO: 9) | thioredoxin (SEQ ID NO: 1, encoding SEQ ID NO: 2) | ZmRbcS (SEQ ID NO: 6) |
| 131779 | ZmCA (SEQ ID NO: 10) | thioredoxin (SEQ ID NO: 1, encoding SEQ ID NO: 2) | ZmCA (SEQ ID NO: 8) |
| 131780 | 4xRGCGR (SEQ ID NO: 7) | thioredoxin (SEQ ID NO: 1, encoding SEQ ID NO: 2) | ZmCA (SEQ ID NO: 8) |

In addition to the single-genic thioredoxin plant transformation constructs listed in Table 2, multigenic plant transformation constructs containing a thioredoxin gene cassette and a second linked cassette were also built. Table 3 summarizes the multigenic thioredoxin plant transformation constructs.

TABLE 3

Thioredoxin multigenic plant transformation constructs

| Construct ID | Thioredoxin Cassette | | | GOI2 Cassette | | | GOI3 Cassette | | |
|---|---|---|---|---|---|---|---|---|---|
| | Promoter + 5'UTR | ORF | 3'UTR | Promoter + 5'UTR2 | ORF2 | 3'UTR2 | Promoter + 5'UTR3 | ORF3 | 3'UTR3 |
| 131261 | GLDC (SEQ ID NO:9) | GRMZM2G181258 (SEQ ID NO:1, encoding SEQ ID NO:2) | ZmRbc5 (SEQ ID NO:6) | Os01g45274 promoter (SEQ ID NO:11) | SBPase (SEQ ID NO:13, encoding SEQ ID NO:14) | Os01g45274 3'utr (SEQ ID NO:12) | | | |
| 131823 | ZmCA1-5'Mod (SEQ ID NO:10) | GRMZM2G181258 (SEQ ID NO:1, encoding SEQ ID NO:2) | ZmCA1 (SEQ ID NO:8) | ZmRbcS + 5'UTR (SEQ ID NO:5) | RbcS-ictB (SEQ ID NO:15, encoding SEQ ID NO:16) | ZmRbcS (SEQ ID NO:6) | | | |
| 131826 | ZmCA1-5'Mod (SEQ ID NO:10) | GRMZM2G181258 (SEQ ID NO:1, encoding SEQ ID NO:2) | ZmCA1 (SEQ ID NO:8) | ZmRbcS + 5'UTR (SEQ ID NO:5) | RbcS-ictB (SEQ ID NO:15, encoding SEQ ID NO:16) | ZmRbcS (SEQ ID NO:6) | Os01g45274 promoter (SEQ ID NO:11) | SBPase (SEQ ID NO:13, encoding SEQ ID NO:14) | Os01g45274 3'utr (SEQ ID NO:12) |

TABLE 3-continued

Thioredoxin multigenic plant transformation constructs

| | Thioredoxin Cassette | | | GOI2 Cassette | | | GOI3 Cassette | | |
|---|---|---|---|---|---|---|---|---|---|
| Construct ID | Promoter + 5'UTR | ORF | 3'UTR | Promoter + 5'UTR2 | ORF2 | 3'UTR2 | Promoter + 5'UTR3 | ORF3 | 3'UTR3 |
| 131834 | 4xRGCGR (SEQ ID NO:7) | GRMZM2G181258 (SEQ ID NO:1, encoding SEQ ID NO:2) | ZmCA1 (SEQ ID NO:8) | Os01g45274 promoter (SEQ ID NO:11) | GRMZM2G01910S (SEQ ID NO:101, encoding SEQ ID NO:102) | OS01g45274 3'utr (SEQ ID NO:12) | | | |
| 132192 | 4xRGCGR (SEQ ID NO:7) | GRMZM2G181258 (SEQ ID NO:1, encoding SEQ ID NO:2) | ZmCA1 (SEQ ID NO:8) | ZmRbcs (SEQ ID NO:103) | ictB (SEQ ID NO:104, encoding SEQ ID NO:105) | ZmRbcS (SEQ ID NO:6) | | | |
| 132222 | 4xRGCGR (SEQ ID NO:7) | GRMZM2G181258 (SEQ ID NO:1, encoding SEQ ID NO:2) | ZmCA1 (SEQ ID NO:8) | GLDC (SEQ ID NO:9) | GRMZM2G004528 (SEQ ID NO:106, encoding SEQ ID NO:107) | ZmRbcS (SEQ ID NO:6) | | | |
| 132234 | 4xRGCGR (SEQ ID NO:7) | GRMZM2G181258 (SEQ ID NO:1, encoding SEQ ID NO:2) | ZmCA1 (SEQ ID NO:8) | OsRbcS promoter (SEQ ID NO:108) | GRMZM2G075336 (SEQ ID NO:109, encoding SEQ ID NO:110) | OsRbcS 3'UTR (SEQ ID NO:111) | | | |
| 132308 | 4xRGCGR (SEQ ID NO:7) | GRMZM2G181258 (SEQ ID NO:1, encoding SEQ ID NO:2) | ZmCA1 (SEQ ID NO:8) | ZmRbcS7A promoter (SEQ ID NO:112) | GRMZM2G122793 (SEQ ID NO:113, encoding SEQ ID NO:114) | ZmRbcS (SEQ ID NO:6) | | | |

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of *Setaria viridis*

*A. tumefaciens* cells harboring thioredoxin plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 4 summarizes the transformation constructs used to transform *S. viridis*, along with the number of PCR-verified transgenic plants that resulted from transformation with each construct.

TABLE 4

Summary of *S. viridis* transformation with thioredoxin plant transformation vectors

| Construct | # Events |
|---|---|
| 130607 | 40 |
| 130994 | 31 |
| 131092 | 35 |
| 131172 | 23 |
| 131261 | 5 |
| 131823 | 31 |
| 131826 | 32 |
| 131834 | 26 |

Example 3—Transformation of Maize (*Zea mays*)

*A. tumefaciens* cells harboring thioredoxin plant transformation vectors are used to transform maize (*Zea mays* cv. B 104) cells suitable for regeneration on tissue culture medium. Following transformation of the maize cells with the relevant plant transformation vectors and regeneration of maize plants, PCR analyses are performed to confirm the presence of the gene(s) of interest in the maize genome.

Example 4—Transformation of Rice (*Oryza sativa*)

*A. tumefaciens* cells harboring thioredoxin plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with a thioredoxin plant transformation vector, the T0-generation plants were cultivated to maturity to produce T1-generation seeds. T1-generation *S. viridis* plants harboring the thioredoxin gene cassette of interest were grown in a greenhouse setting to assess the effects of thioredoxin gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 5 summarizes the results of the biomass and seed yield determinations made from experiments with T1-generation *S. viridis* plants harboring a thioredoxin gene cassette as a result of transformation. It should be noted that growth conditions (e.g., temperature and light conditions) likely changed among the experiments used to test the 131092, 131172, and 130607 events, and thus there were differences in growth between these experiments; comparisons were made between transgenic and null segregants grown under identical environmental conditions, with the events from a given construct grouped together in Table 5. Null segregant controls were not available for events from the 131172 construct, and thus wild-type (WT) negative controls were used. Pooled null segregants from several different transformation constructs were used as the negative control in the experiment used to characterize 130607 events. This table indicates the construct used for transformation, as described in Tables 2 and 3, followed by the T0 event number from which the T1 seed was harvested.

TABLE 5

Summary of *S. viridis* greenhouse observations with T1-generation plants

|  | DW (g) | Seed Yield (g) | DW Change (%) | Seed Change (%) |
| --- | --- | --- | --- | --- |
| 131092-25 | 2.98 ± 0.63 | 0.53 ± 0.13 | −3.20% | 0.00% |
| 131092-26 | 4.71 ± 0.25 | 0.79 ± 0.08 | 52.90% | 49.10% |
| 131092-7 | 3.01 ± 0.45 | 0.49 ± 0.08 | −2.30% | −7.50% |
| 131092-9 | 3.36 ± 0.41 | 0.59 ± 0.10 | 9.10% | 11.30% |
| 131092-null | 3.08 ± 0.50 | 0.53 ± 0.11 | n/a | n/a |
| 131172-2A | 2.87 ± 0.46 | 0.49 ± 0.13 | −29.80% | −27.90% |
| 131172-3A | 3.31 ± 0.46 | 0.57 ± 0.09 | −19.10% | −16.20% |
| 131172-4A | 3.30 ± 0.54 | 0.53 ± 0.12 | −19.30% | −22.10% |
| 131172-5A | 2.08 ± 0.68 | 0.33 ± 0.14 | −49.10% | −51.50% |
| 131172-6B | 3.35 ± 0.37 | 0.53 ± 0.08 | −18.10% | −22.10% |
| WT | 4.09 ± 0.49 | 0.68 ± 0.11 | n/a | n/a |
| 130607-11 | 2.07 ± 0.24 | 0.27 ± 0.04 | −12.70% | −28.90% |
| 130607-12a | 2.17 ± 0.22 | 0.23 ± 0.03 | −8.40% | −39.50% |
| 130607-13 | 1.62 ± 0.15 | 0.18 ± 0.04 | −31.60% | −52.60% |
| 130607-14a | 1.72 ± 0.11 | 0.16 ± 0.02 | −27.40% | −57.90% |
| 130607-7 | 1.87 ± 0.26 | 0.24 ± 0.04 | −21.10% | −36.80% |
| 130607-9a | 2.20 ± 0.22 | 0.33 ± 0.05 | −7.20% | −13.20% |
| Null | 2.37 ± 0.34 | 0.38 ± 0.05 | n/a | n/a |
| 131261-1 | 4.66 ± 0.21 | 1.38 ± 0.10 | −4.75% | 6.29% |
| 131261-2 | 4.88 ± 0.56 | 1.28 ± 0.20 | −0.44% | −1.41% |
| 131261-3 | 4.83 ± 0.25 | 1.33 ± 0.11 | −1.36% | 2.59% |
| 131261-4A | 5.05 ± 0.21 | 1.35 ± 0.06 | 3.19% | 4.29% |
| 131261-4B | 4.91 ± 0.19 | 1.24 ± 0.14 | 0.29% | −4.18% |
| 131261-Null | 4.90 ± 0.10 | 1.29 ± 0.10 | n/a | n/a |

In Table 5, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the appropriate construct. As this table shows, two of the four events tested from the 131092 construct showed higher biomass and seed yields than the null controls from this construct. The transgenic events from the 130607 and 131172 constructs showed lower biomass and seed yields than their respective negative controls. The transgenic events from the 131261 construct showed small changes in biomass and seed yield relative to controls.

Example 6—Characterization of Transgenic Maize

T0-generation maize plants transformed with the thioredoxin plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the thioredoxin gene cassette and any other relevant gene cassettes (e.g., a selectable marker gene cassette) that were included in the thioredoxin plant transformation vector. Following the maturation of the maize plants, the seed is harvested. Seeds from the plants containing the thioredoxin gene cassette are pooled, as are seeds from the null segregant plants lacking the thioredoxin gene cassette. The seeds are weighed, and seed yields are calculated for the plants containing the thioredoxin gene cassette as well as for the null segregant plants lacking the thioredoxin gene cassette. Appropriate statistical analyses are performed to determine whether plants containing a thioredoxin gene cassette produce higher yields than those plants that lack a thioredoxin gene cassette.

Alternatively, T0-generation maize plants transformed with the thioredoxin plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the thioredoxin gene cassette are pooled, as are seeds from the null segregant plants lacking the thioredoxin gene cassette. The seeds are weighed, and seed yields are calculated for the plants containing the thioredoxin gene cassette as well as for the null segregant plants lacking the thioredoxin gene cassette. Appropriate statistical analyses are performed to determine whether plants containing a thioredoxin gene cassette produce higher yields than those plants that lack a thioredoxin gene cassette.

Example 7—Characterization of Transgenic Rice

T0-generation rice plants transformed with the thioredoxin plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing a thioredoxin gene cassette produce higher yields than those plants that lack a thioredoxin gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing a thioredoxin gene cassette produce higher yields than those plants that lack a thioredoxin gene cassette.

We claim:

1. A method for increasing crop yield comprising transforming a plant with at least one m-type thioredoxin protein-encoding sequence comprising
    an m-type thioredoxin sequence encoding a protein having at least 85% identity to SEQ ID NO:2, wherein the protein is a functional m-type thioredoxin protein,
    wherein said m-type thioredoxin protein-encoding sequence is operably linked to a promoter comprising SEQ ID NO:7.

2. The method of claim 1, wherein said m-type thioredoxin protein-encoding sequence comprises SEQ ID NO:1, or encodes a protein selected from the group consisting of SEQ ID NOs:2 and 17-20.

3. A DNA construct comprising, in operable linkage,
    a) a promoter comprising SEQ ID NO:7 and,
    b) an m-type thioredoxin protein-encoding sequence that comprises SEQ ID NO:1 or
    encodes a protein selected from the group consisting of SEQ ID NOs:2 and 17-20, wherein said promoter is heterologous to said m-type thioredoxin protein-encoding sequence.

4. A plant having stably incorporated into its genome the DNA construct of claim 3.

5. A transformed seed of the plant of claim 4, wherein said seed comprises said m-type thioredoxin protein-encoding sequence.

6. The plant of claim 4 wherein said plant is a monocot.

7. The plant of claim 4 wherein said plant is a dicot.

8. The method of claim 1, wherein at least one m-type thioredoxin protein-encoding sequence comprises a nucleic acid sequence having at least 95% sequence identity to SEQ ID NO:1 and encoding a functional m-type thioredoxin protein.

9. A DNA construct comprising, in operable linkage,
    a) a promoter comprising SEQ ID NO:7 and,
    b) an m-type thioredoxin protein-encoding sequence that encodes a protein
    comprising an amino acid sequence having at least 85% sequence identity to SEQ ID
    NO:2, wherein the protein is a functional m-type thioredoxin protein, and wherein said promoter is heterologous to said m-type thioredoxin protein-encoding sequence.

10. The DNA construct of claim 9, wherein said m-type thioredoxin protein-encoding sequence comprises a nucleic acid sequence having at least 95% sequence identity to SEQ ID NO: 1 and encodes a functional m-type thioredoxin protein.

11. The DNA construct of claim 9, wherein said m-type thioredoxin protein-encoding sequence comprises the nucleic acid sequence of SEQ ID NO: 1.

* * * * *